(12) United States Patent
Tarlton

(10) Patent No.: US 11,564,440 B1
(45) Date of Patent: Jan. 31, 2023

(54) SYSTEM AND METHODS FOR ADJUSTING VARIABLE GEOMETRY, HEIGHT, WEIGHT DISTRIBUTION DYNAMICS IN ORTHOTIC DEVICES AND EQUIPMENT

(71) Applicant: ALLIANCE DESIGN AND DEVELOPMENT GROUP, INC., Matawan, NJ (US)

(72) Inventor: Peter B. Tarlton, Rockingham, NH (US)

(73) Assignee: Alliance Design and Development Group, Matawan, NJ (US)

( * ) Notice: Subject to any disclaimer, the term of this patent is extended or adjusted under 35 U.S.C. 154(b) by 114 days.

(21) Appl. No.: 17/171,975

(22) Filed: Feb. 9, 2021

Related U.S. Application Data

(63) Continuation-in-part of application No. 16/254,261, filed on Jan. 22, 2019, now Pat. No. 10,959,484,
(Continued)

(51) Int. Cl.
*A43B 7/24* (2006.01)
*A63B 21/02* (2006.01)
(Continued)

(52) U.S. Cl.
CPC .............. *A43B 7/24* (2013.01); *A01D 7/00* (2013.01); *A01D 7/06* (2013.01); *A01K 87/00* (2013.01); *A43B 3/246* (2013.01); *A43B 3/34* (2022.01); *A43B 3/38* (2022.01); *A43B 7/141* (2013.01); *A43B 7/142* (2013.01); *A43B 7/143* (2013.01); *A43B 7/1445* (2013.01); *A43B 7/1464* (2022.01); *A43B 7/1466* (2022.01); *A43B 17/02* (2013.01); *A43B 17/04* (2013.01); *A43B 17/14* (2013.01); *A61F 5/0102* (2013.01); *A61F 5/0111* (2013.01); *A61F 5/0123* (2013.01); *A63B 5/06* (2013.01); *A63B 21/0004* (2013.01); *A63B 21/00069* (2013.01); *A63B 21/00072* (2013.01); *A63B 21/026* (2013.01); *A63B 21/0442* (2013.01); *A63B 21/4023* (2015.10); *A63B 21/4029* (2015.10); *A63B 21/4035* (2015.10); *A63B 21/4037* (2015.10); *A63B 21/4043* (2015.10); *A63B 22/0056* (2013.01); *A63B 22/02* (2013.01); *A63B 22/0605* (2013.01); *A63B 22/0664* (2013.01);
(Continued)

(58) Field of Classification Search
CPC ... A43B 7/1465; A43B 7/1464; A43B 7/1467; A43B 7/1469; A43B 7/24; A43B 7/1466; A43B 7/142; A43B 7/143
USPC ................... 36/150, 155–161, 165
See application file for complete search history.

(56) References Cited

U.S. PATENT DOCUMENTS

| | | |
|---|---|---|
| 1,558,192 A | 10/1925 | Lindgren |
| 2,295,364 A | 9/1942 | Skorepa |

(Continued)

*Primary Examiner* — Ted Kavanaugh
(74) *Attorney, Agent, or Firm* — Law Office of Carl Giordano, PC

(57) ABSTRACT

An active suspension orthotic support system is disclosed. The suspension orthotic support system comprises at least one variable resistance beam extending from a heel section to a mid-arch section of the footwear, wherein rotation of the variable resistance beam from a first position to a second position causes a resistance provided by the variable resistance beam to vary between a minimum resistance to a maximum resistance.

19 Claims, 48 Drawing Sheets

Related U.S. Application Data which is a continuation-in-part of application No. 15/425,772, filed on Feb. 6, 2017, now Pat. No. 10,188,173, which is a continuation of application No. 14/543,870, filed on Nov. 17, 2014, now Pat. No. 9,603,416, which is a continuation-in-part of application No. 13/622,331, filed on Sep. 18, 2012, now abandoned.

(60) Provisional application No. 62/620,951, filed on Jan. 23, 2018, provisional application No. 61/905,688, filed on Nov. 18, 2013, provisional application No. 61/585,315, filed on Jan. 11, 2012.

(51) Int. Cl.

| | | |
|---|---|---|
| *A63B 21/04* | (2006.01) | |
| *A63B 22/00* | (2006.01) | |
| *A63B 22/02* | (2006.01) | |
| *A63B 22/06* | (2006.01) | |
| *A63B 23/12* | (2006.01) | |
| *A63B 49/02* | (2015.01) | |
| *A63B 53/10* | (2015.01) | |
| *A63B 21/00* | (2006.01) | |
| *A63B 59/70* | (2015.01) | |
| *A63B 59/20* | (2015.01) | |
| *A63B 59/50* | (2015.01) | |
| *A61F 5/01* | (2006.01) | |
| *A63C 5/07* | (2006.01) | |
| *A63B 60/50* | (2015.01) | |
| *A01D 7/06* | (2006.01) | |
| *A43B 7/143* | (2022.01) | |
| *A01D 7/00* | (2006.01) | |
| *A43B 3/24* | (2006.01) | |
| *A43B 7/1405* | (2022.01) | |
| *A43B 7/1445* | (2022.01) | |
| *A43B 17/02* | (2006.01) | |
| *A43B 17/04* | (2006.01) | |
| *A43B 17/14* | (2006.01) | |
| *A63B 5/06* | (2006.01) | |
| *A63B 23/035* | (2006.01) | |
| *A63B 24/00* | (2006.01) | |
| *A63B 71/06* | (2006.01) | |
| *A63C 5/04* | (2006.01) | |
| *A43B 7/142* | (2022.01) | |
| *A01K 87/00* | (2006.01) | |
| *A43B 3/34* | (2022.01) | |
| *A43B 3/38* | (2022.01) | |
| *A43B 7/1464* | (2022.01) | |
| *A43B 7/1466* | (2022.01) | |
| *A63B 71/02* | (2006.01) | |
| *A63B 102/24* | (2015.01) | |
| *A63B 102/18* | (2015.01) | |
| *A63B 102/02* | (2015.01) | |
| *A63B 23/04* | (2006.01) | |
| *A63B 69/18* | (2006.01) | |
| *A63B 69/00* | (2006.01) | |
| *A63B 102/22* | (2015.01) | |
| *A63B 21/16* | (2006.01) | |
| *A63B 69/06* | (2006.01) | |
| *A63B 69/36* | (2006.01) | |
| *A61B 5/00* | (2006.01) | |
| *A63B 60/42* | (2015.01) | |
| *A63B 69/16* | (2006.01) | |
| *A63B 22/04* | (2006.01) | |

(52) U.S. Cl.
   CPC .... *A63B 23/03533* (2013.01); *A63B 23/1209* (2013.01); *A63B 24/0062* (2013.01); *A63B 49/02* (2013.01); *A63B 53/10* (2013.01); *A63B 59/20* (2015.10); *A63B 59/50* (2015.10); *A63B 59/70* (2015.10); *A63B 60/50* (2015.10); *A63B 71/0622* (2013.01); *A63C 5/04* (2013.01); *A63C 5/07* (2013.01); *A61B 5/4528* (2013.01); *A61B 5/6812* (2013.01); *A61B 2505/09* (2013.01); *A61B 2562/0219* (2013.01); *A61B 2562/0261* (2013.01); *A63B 21/16* (2013.01); *A63B 21/169* (2015.10); *A63B 22/0012* (2013.01); *A63B 22/04* (2013.01); *A63B 23/03508* (2013.01); *A63B 23/03525* (2013.01); *A63B 23/03541* (2013.01); *A63B 23/0405* (2013.01); *A63B 60/42* (2015.10); *A63B 69/0093* (2013.01); *A63B 69/06* (2013.01); *A63B 69/16* (2013.01); *A63B 69/18* (2013.01); *A63B 69/36* (2013.01); *A63B 71/023* (2013.01); *A63B 2071/027* (2013.01); *A63B 2071/0694* (2013.01); *A63B 2102/02* (2015.10); *A63B 2102/18* (2015.10); *A63B 2102/22* (2015.10); *A63B 2102/24* (2015.10); *A63B 2209/02* (2013.01); *A63B 2210/50* (2013.01); *A63B 2220/24* (2013.01); *A63B 2220/40* (2013.01); *A63B 2220/52* (2013.01); *A63B 2220/53* (2013.01); *A63B 2220/56* (2013.01); *A63B 2225/09* (2013.01); *A63B 2225/093* (2013.01); *A63B 2225/20* (2013.01); *A63B 2225/50* (2013.01); *A63B 2225/54* (2013.01); *A63C 2203/20* (2013.01)

(56) References Cited

U.S. PATENT DOCUMENTS

| | | | |
|---|---|---|---|
| 3,729,842 A | 5/1973 | Stelzer | |
| 3,794,037 A | 2/1974 | Matteson | |
| 6,345,455 B1 | 2/2002 | Greer, Jr. | |
| 6,393,736 B1 * | 5/2002 | Greer, Jr. | A61F 5/14 36/161 |
| 9,603,416 B1 * | 3/2017 | Walsh | A63B 22/02 |
| 10,188,173 B1 * | 1/2019 | Walsh | A43B 3/246 |
| 10,959,484 B1 * | 3/2021 | Tarlton | A43B 17/04 |
| 2004/0064974 A1 | 4/2004 | Schuster | |
| 2004/0148799 A1 | 8/2004 | Lussier | |
| 2005/0039351 A1 * | 2/2005 | McCracken | A61F 5/14 36/156 |
| 2010/0275460 A1 | 11/2010 | Ha | |
| 2013/0014407 A1 | 1/2013 | Savage | |
| 2013/0178344 A1 | 7/2013 | Walsh | |
| 2013/0283646 A1 | 10/2013 | Seiner | |
| 2015/0057587 A1 | 2/2015 | Walsh | |

* cited by examiner

100

Type I

Fulcrum Resistance = Hand Positions = A, B, C, D, E, Indicia

FIG. 1B (a)
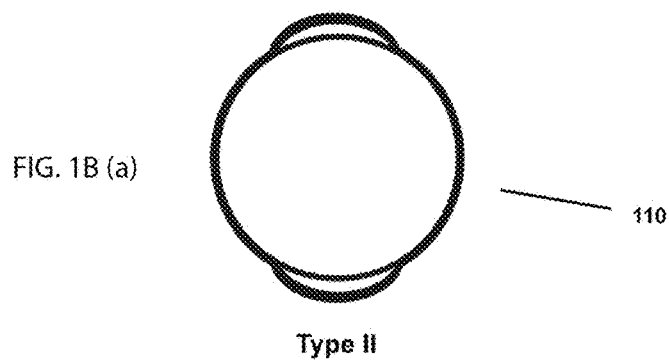
Type II
FIG. 1B (b)
FIG. 1B (c)
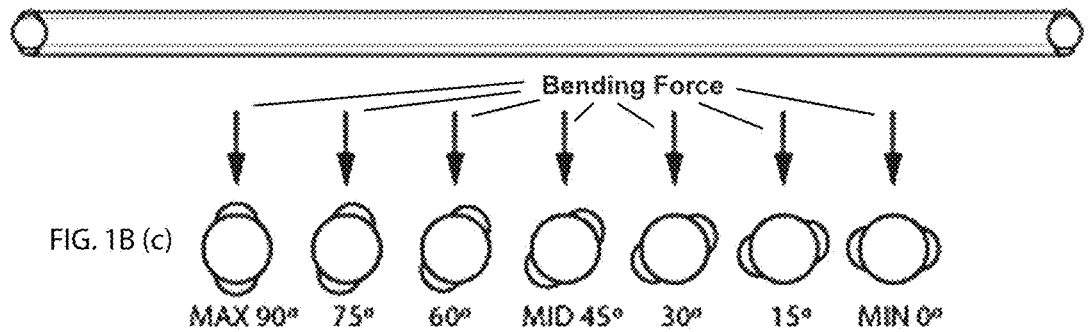
Bending Force
MAX 90°  75°  60°  MID 45°  30°  15°  MIN 0°
FIG. 1B (d)
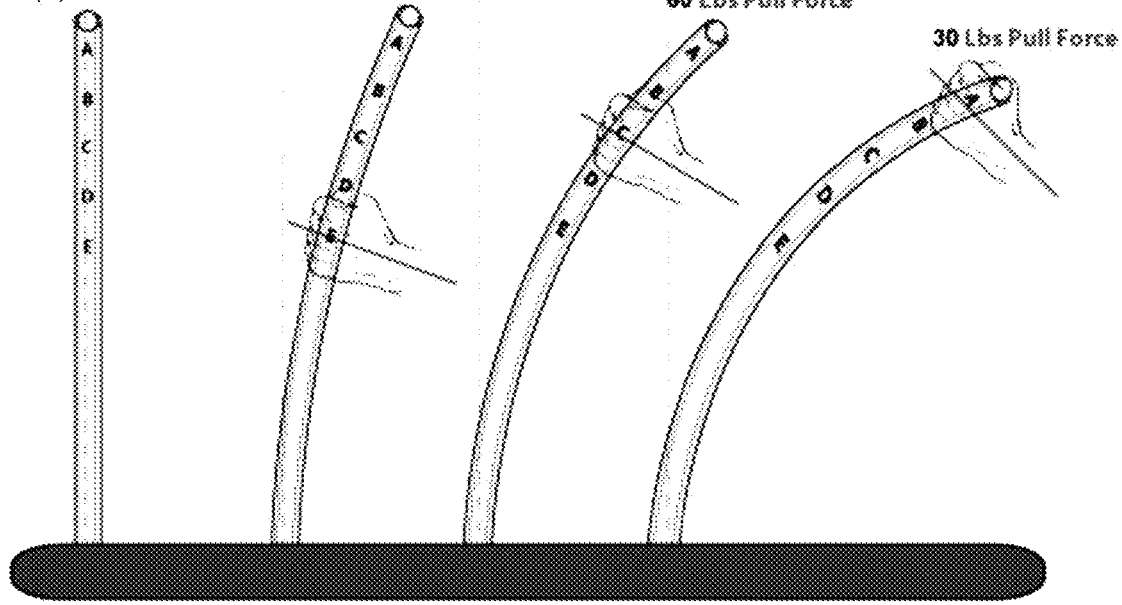
90 Lbs Pull Force   60 Lbs Pull Force   30 Lbs Pull Force

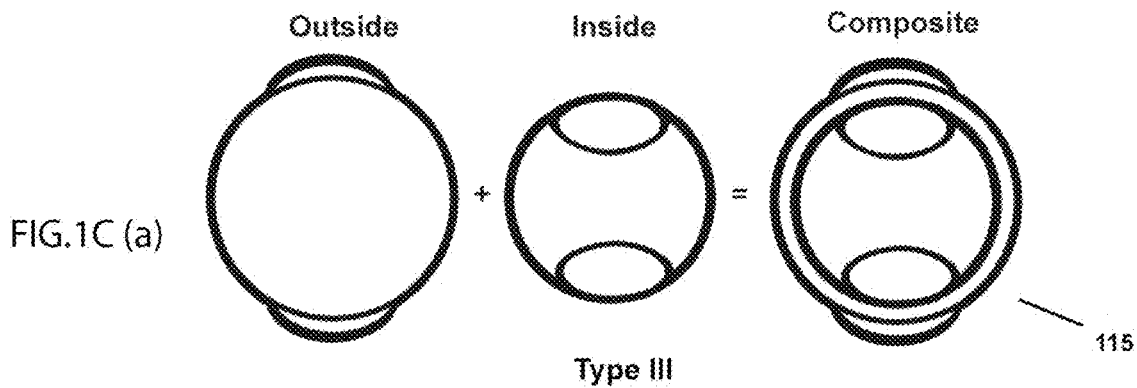
FIG.1C (a)
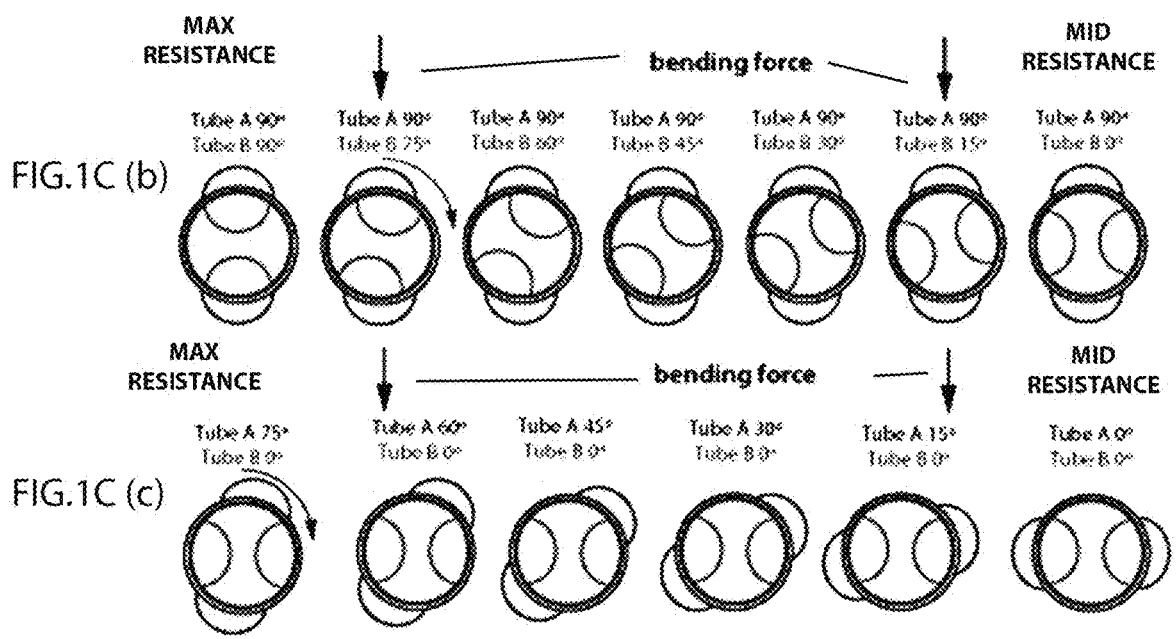
FIG.1C (b)
FIG.1C (c)
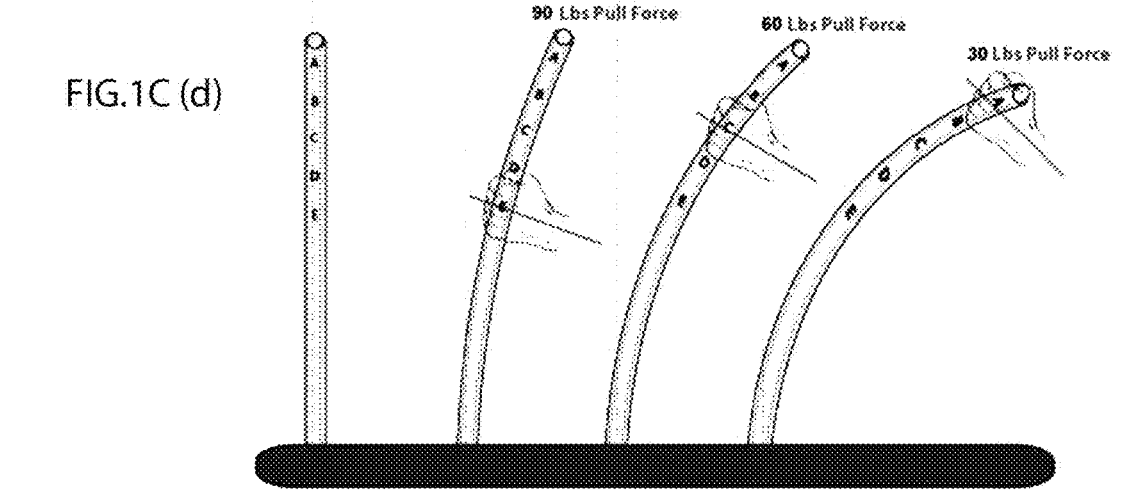
FIG.1C (d)

Type V

Type VI

MAX Resistance — MIN Resistance

Cylindrical Spine Reinforced Beam

Conical Spine Reinforced Beam

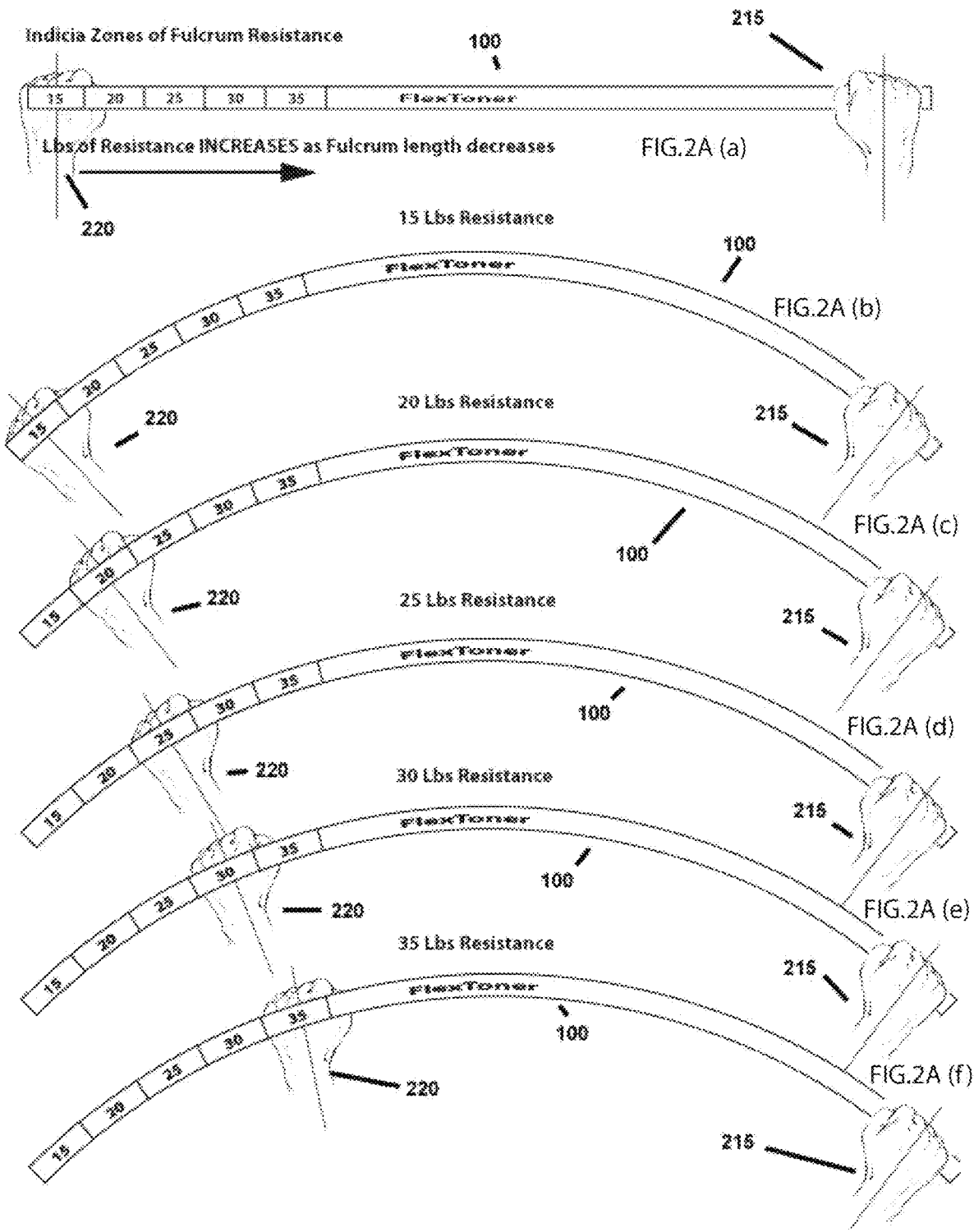

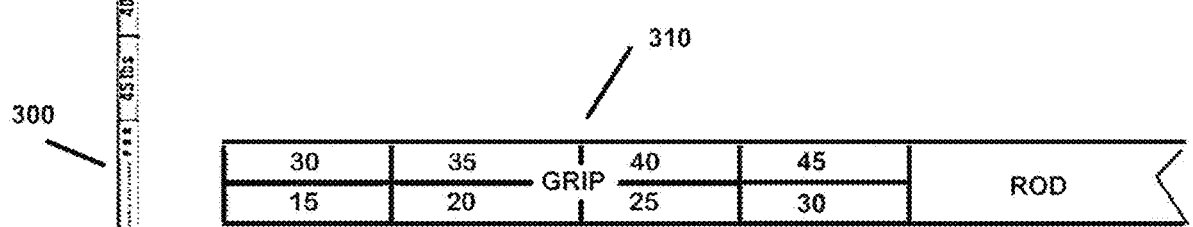
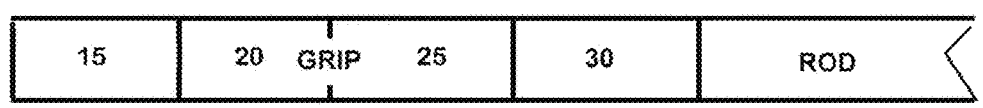
FIG.3 (a)
FIG.3 (b)
FIG.3 (c)

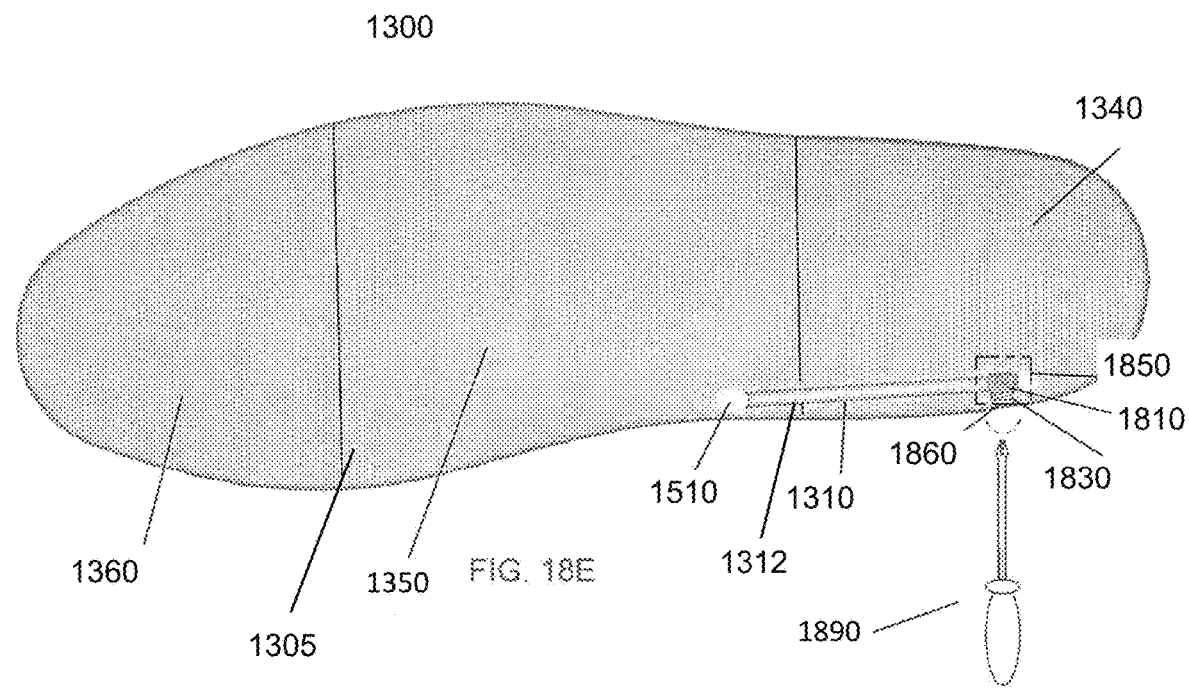
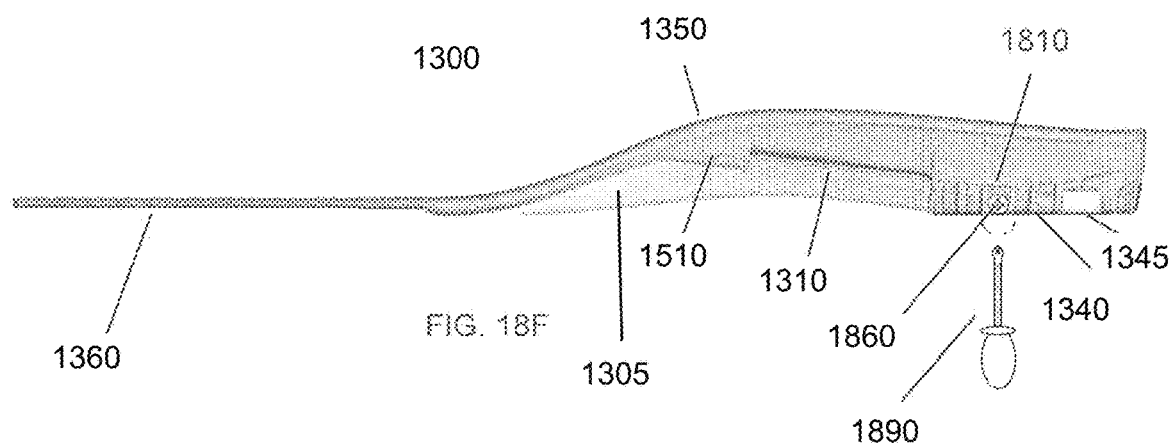

MALE HELIX

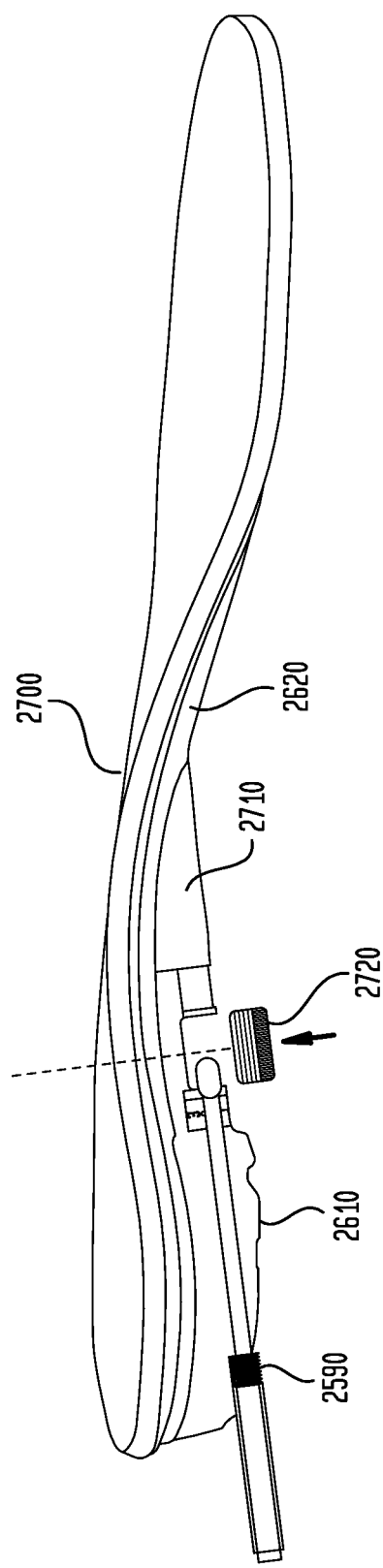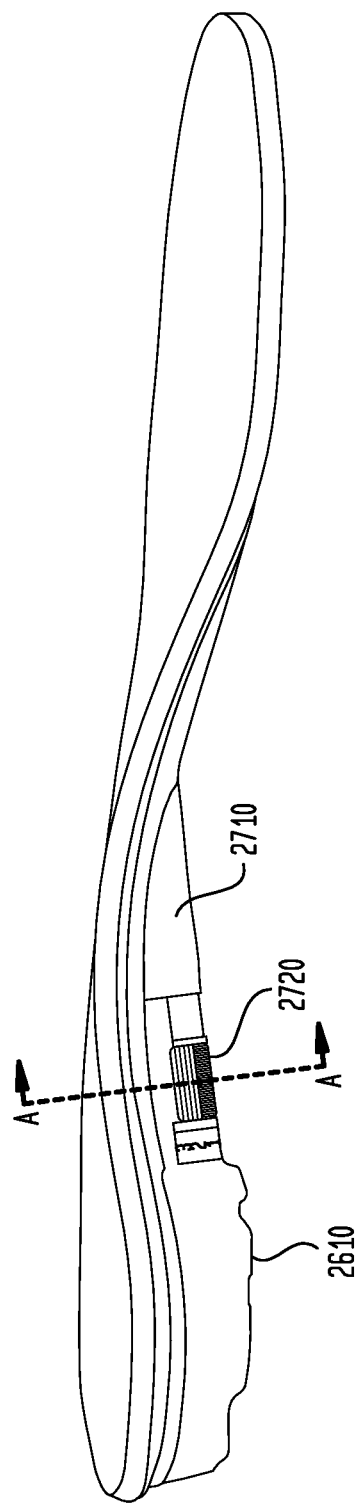

SYSTEM AND METHODS FOR ADJUSTING VARIABLE GEOMETRY, HEIGHT, WEIGHT DISTRIBUTION DYNAMICS IN ORTHOTIC DEVICES AND EQUIPMENT

CLAIM OF PRIORITY

This application claims, pursuant to 35 USC 120, as a Continuation in Part Application, priority to and the benefit of the earlier filing date of that patent application filed on Jan. 22, 2019 and afforded Ser. No. 16/254,261 (now U.S. Pat. No. 10,959,484) which claimed pursuant to 35 USC 119, priority to and the benefit of the earlier filing date of provisional patent application Ser. No. 62/620,951, filed on Jan. 23, 2018 and further claimed, pursuant to 35 USC 120, as a Continuation-in-Part application, priority to that patent application filed on Feb. 26, 2017 and afforded Ser. No. 15/425,772 (U.S. Ser. No. 10/188,173), which claimed pursuant to 35 USC 120, as a Continuation Application, priority to that patent application, filed on Nov. 17, 2014 and afforded Ser. No. 14/543,870 (U.S. Pat. No. 9,603,416), which claimed, pursuant to 35 USC 119, priority to and the benefit of the earlier filing date of that provisional patent application filed on Nov. 18, 2013 and afforded Ser. No. 61/905,688 and further claimed, pursuant to 35 USC 120, as a continuation in part, priority to that patent application filed on Sep. 18, 2012 and afforded Ser. No. 13/622,331, (now Abandoned) which claimed, pursuant to 35 USC 119, the benefit of the earlier filing date of that provisional patent application filed on Jan. 11, 2012 and afforded Ser. No. 61/585,315, the entire contents of all of which are incorporated by reference, herein.

RELATED APPLICATION

This application is related to that patent application entitled "System and Methods for Adjusting Variable Geometry, Height, Weight Distribution Dynamics in Footwear Devices and Equipment," filed on Nov. 17, 2014 and afforded Ser. No. 14/543,883, the contents of which are incorporated by reference herein.

FIELD OF THE INVENTION

The invention relates to the field of devices, apparatus and equipment whose degree of stiffness and flexibility may be varied or dynamically controlled. And more particularly to an orthotic shoe insert for providing a stiffness that may be adjusted.

BACKGROUND

There is a need for varying and adjusting the flexibility and stiffness of associated devices, apparatus and equipment to customize to a user's unique needs, and to the requirements of a particular task or desired outcome.

For example, in recent years, as it relates to the category of sports and fitness equipment, manufacturers and marketers have increasingly turned to different kinds of methods to enhance the customization and performance of sporting and fitness equipment. In some cases, entire lines of sporting equipment have been developed whose stiffness or flexibility characteristics are different from each other and are designed to be matched to the user's unique needs. Such differences, however, may be enough to give the individual equipment user an edge over the competition in that the equipment can be more personally customized, matched to a desired goal, and, therefore, enhance performance.

Until now, the user may choose a particular piece of sporting or fitness equipment having a desired stiffness or flexibility characteristic and, during play, switch to a different piece of sporting equipment that is slightly more flexible or stiffer to suit changing playing conditions or to help compensate for weariness or fatigue or some other anomaly that prevents optimum performance. Such switching, of course, is subject to the availability of different pieces of sporting or fitness equipment from which to choose, at the precise moment the change or adjustment is needed. In many cases, the availability is limited due to cost and over all impracticability.

Additionally, subtle but important changes in the stiffness or flexibility characteristics of sporting or fitness equipment may not be available between different pieces of sporting equipment, because the characteristics may be set by the manufacturer from the choice of materials, design, etc., and to change the characteristics would be impossible, as such customization isn't offered to the user. Further, the user must have the different pieces of sporting equipment nearby during play or they are essentially in practice unavailable to the user.

Thus, it can be seen how the lack of adjustability in stiffness and flexibility may adversely affect optimum performance of a device, apparatus, and equipment.

Turning to additional types of devices, apparatus and equipment, it can be seen how the lack of a practical means of adjustability in stiffness and flexibility may adversely affect performance.

Medical Devices, Apparatus, and Equipment

Medical devices, apparatus and equipment, such as braces that are used for supporting injured limbs, require the flexibility of the device to be adjusted based on the degree of the injury, type of surgery, and the progress of the healing of the injured party. Further, there is a need for on-going protection even after recovery. Yet the degree of adjustability of braces is limited, and, in most cases, fixed. Adjustability of the flexibility of the brace the brace to the specific needs and requirements of the user, may enhance recovery and protection from further injury.

Fitness Devices, Apparatus, and Equipment

Fitness equipment, apparatus and devices require the creation of different amounts of resistance to perform the exercise. For example, with free-weight training the user must change the weight levels to progressively increase the resistance that the user experiences. This often involves the continued and time consuming adjustment of equipment through an exercise cycle and makes changes impractical at best, and at the least a hassle.

Numerous heavy metal plates, large oily machines, weights, rubber bands, and singular resistance rods are the many known forms of fitness training. When the user changes resistance/weight or machine during an exercise set, it is time consuming and interrupts the user's conditioning.

Running Shoes, Training Shoes, Basketball Shoes

The transmission of the shoe wearer's strength (power) from their legs into the ground is directly affected by the sole stiffness of the shoe. Runners may gain more leverage and, thus, more speed by using a stiffer sole. Basketball players may also affect the height of their jumps through the leverage transmitted by the sole of their shoes. If the sole is too stiff, however, the toe-heel flex of the foot is hindered. Thus, athletic shoes are tailored, by the manufacturer, to the particular sport to which the shoe is to be used. In some case, it may be possible for the user have the ability to tailor the sole stiffness to his/her individual weight, strength, height, running style, and ground conditions. However, this process is performed by the manufacturer and is beyond the ability of the average user.

Golf

Golf clubs may be formed of graphite, wood, titanium, glass fiber or various types of composites or metal alloys. Each material varies to some degree with respect to stiffness and flexibility. However, golfers generally carry onto the golf course only a predetermined number of golf clubs. Varying the stiffness or flexibility of the golf club is not possible, unless the golfer brings another set of clubs. Nevertheless, it is impractical to carry a large number of golf clubs onto the course, wherein each club having a slight nuance of difference in flexibility and stiffness than another. Golf players prefer taking onto the course a set of clubs that are suited to the player's specific swing type, strength and ability.

Hockey

Hockey (hockey includes, but is not limited to, ice hockey, street hockey, roller hockey, held hockey and floor hockey) players may require that the flexure of the hockey stick be changed to better assist in the wrist shot or slap shot needed at that particular junction of a game or which the player was better at making.

Younger players may require more flex in the hockey stick due to lack of strength; such flex may mean the difference between the younger player being able to lift the puck or not when making a shot since a stiffer flex in the stick may not allow the player to achieve such lift. In addition, as the younger players ages and increases in strength, the player may desire a stiffer hockey stick, which in accordance with conventional means the hockey player would need to purchase additional hockey stick shafts with the desired stiffness and flexibility characteristics. Indeed, to cover a full range of nuances of differing stiffness and flexibility characteristics, hockey players would have available many different types of hockey sticks. Even so, the hockey player may merely want to make a slight adjustment to the stiffness or flexibility of a hockey stick to improve the nuances of the play; which is not possible with conventional technology Tennis Tennis players also may want some stiffness and/or adjustability in their tennis rackets and to resist unwanted torsional effects caused by the ball striking the strings during play. The torsional effects may be more pronounced in the case where the ball strikes near the rim of the racket rather than the center of the strings.

Lacrosse

Lacrosse players use their lacrosse sticks to scoop up a lacrosse ball and pass the ball to other players or toward the goal. The stiffness or flexibility of the lacrosse stick may affect performance during the game.

Other Racket Sports

Other types of racket sports also suffer from the drawback of being unable to vary the stiffness and/or flexibility of the racket during the course of play to suit the needs of the player at that time, whether those needs arise from weariness, desired held positions, or training for improvement. Such racket sports include racquetball, paddleball, squash, badminton, and court tennis.

For conventional rackets, the stiffness and flexibility is set by the manufacturer and invariable. If the player tires of such characteristics being fixed or otherwise wants to vary the stiffness and flexibility, the only practical recourse is to switch to a different racket whose stiffness and flexibility characteristics better suit the needs of the player at that time.

Skiing, Snowboarding, Snow Skating, Ski-Boarding

Skis are made from a multitude of different types of materials and dimensions, the strength and flexibility of each type differing to a certain extent. Skis include those for downhill, ice skiing, cross-country skiing and water-skiing. For soft snow conditions, the rider may want to have more flexibility so as to allow the board to float. For icier conditions, the rider may want to stiffen the highback to provide greater leverage and power, which results in greater edge control.

Bicycle Shoes

Bicycle specific shoes are rigid and may or may not be attached to bicycle pedals usually through a binding or clip mechanism that prohibits the shoe from slipping of the pedal. The shoe is positioned on the pedal so the ball of the foot is directly over the pedal. The rider's foot flexes as the pedal moves. However, the bicycle shoe is designed for pedaling and walking in these shoes is uncomfortable.

Fishing Rods

Fishing rods are flexed for casting out a line. The whip effect from the casting is affected by the stiffness or flexibility of the rod. Depending upon the fishing conditions and the individual tastes of the user, the user may prefer the rod to be either more flexible or stiffer to optimize the whip effect of the cast and to deal with wind, current, types of fish, and the like. Thus, the user must select the type of flexibility or stiffness when purchasing the fishing rod.

Fins

Diving and swimming fins provide different degrees of stiffness that are fixed, and unchangeable. However, the need to have more flex or less flex and, thus, control fin bend is dependent on the changing conditions. Optimum performance that matches the conditions may be possible with dynamically adjustable fin spine(s). It would also be advantages in that the swimmer/diver would not be unnecessarily fatigued if they had proper matching flex to the conditions.

Sailboating and Sailboarding

Masts of sailboats and sailboards support sails. In many cases the users must adjust the amount of sail that is hanging from the mast according to the weather conditions to prevent damaging the mast caused by stress on the mast.

Canoeing, Rowboating and Kayaking

Paddles for canoes, row boats, and kayaks are subjected to forces as they are stroked through water. The flexibility or stiffness of the paddles, while different depending upon its design and materials, is fixed by the manufacturer. Thus, a rower who desired to change such characteristics would need to switch to a different type of paddle. Carrying a multitude of different types of paddles for use with a canoe, row boat or kayak, however, is generally impractical for the typical rower from the standpoint of cost, bulk and storage.

Lawn Rake

There are times when the flex of a rake's tines are either too flexible or too stiff for the task at hand, be it for raking gardens, light leaf, matted thatch, wet grass, debris. Often the user has to purchase a second rake to accommodate these additional needs.

Orthotics

Orthotics for providing corrective positioning of the foot while walking, running or participating in sports is generally custom fitted for the user. This typically involves the characteristics of the user being measured by a doctor to determine the needed corrective configuration. These custom fits are typically a static solution. Orthotics may then be fabricated based on the determined corrective configuration.

Corrective orthotics are relatively expensive to purchase, are often not included for health insurance reimbursement and are time consuming in preparing. Most important, the final product is always static and non-dynamic. There also remains the issue of patient break-in, which can be uncomfortable and even painful as the foot is manipulated to the demands of the orthotic because of the customized orthotics are non-dynamic and static in shape.

Conventional non-prescriptive orthotic offerings consist mainly of cushioned insoles, which have limited palliative benefits that are short-lived but are not biomechanically corrective. There are fewer products that attempt to provide the wearer non-dynamic correction to biomechanical anomalies without going to see a doctor.

Thus, with corrective orthotics, a user may, in time, experience less pain from bio-mechanical issues when walking, running or participating in sports. They also attempt to limit the potential for long term, chronic maladies of the feet, ankles, knees, hips, and back.

In addition, users that do not require corrective orthotics may use a cushioning insole in order to provide relief or prevent pain when participating in exercises that apply significant pressure on the foot.

Cushioning insoles are generally composed of a gel-type material that distributes the user's weight over the surface of the foot. However, the cushioning insole is general in size according to the user's shoe size, and is not bio-mechanically corrective.

However, the current state of customized orthotics is one that is expensive and/or not dynamically adapted to changing conditions that the user may experience while walking or running.

Hence, there is a need in the industry of an orthotic system that provides the user with the ability to customize or adapt their orthotics in order to provide not only a comfortable fit during different activities but one that is bio-mechanically dynamic and adjustable by the user's unique structural demands.

SUMMARY OF THE INVENTION

The invention relates to a variable resistance beam or rod that may dynamically control the stiffness and flexibility of devices, apparatus, and equipment. The resilient rods, beams or shafts of solid, semi-solid or hollow construction produce resistance and variable resistances when orientated in a direction of x, y, z plane or combination of planes in 360 degrees of rotation or bending movement.

The variable resistance rod (VRB) technology may be incorporated into different equipment (sports & fitness, lawn, medical, etc.) that require different degrees and direction of stiffness and flexibility, wherein the different degrees of stiffness and flexibility may be controlled in the field in real time by means of a selector, a worm gear, or other mechanical methods to affect a rotated orientation of the variable resistance rods, or by simple hand placement in relation to the fulcrum indicated by an indicia of color, number, symbol or other means.

One aspect of the invention resides in a resilient or resistance rod acting to create variable resistance that incorporates a selectable or adjustable flex resistance by means of hand position and placement.

One aspect of the invention resides in a resilient rod, beam or shaft, including at least one spine, extending substantially the length of the rod, beam or shaft, that provides for variable degrees of flexibility of the rod, shaft or beam depending upon the orientation of the spine with regard to a direction of flex One aspect of the invention resides in equipment that adjusts to provide variations in stiffness and flexibility. The equipment may have a rod, beam or shaft with an elongated cavity or rod, an elongated flexure resistance spine, one, two or more locking elements that secure the rod, shaft or beam against rotation at spaced apart locations within the cavity. The rod, shaft or beam is stiffer and less flexible in one direction than in another.

Another aspect of the invention resides in sports equipment that provides variations in stiffness and flexibility. The sports equipment may have an elongated cavity, and a means imparting stiffness and flexibility variations within the cavity so the sports equipment becomes stiffer, and less flexible, in one direction than in another, and one or more locking elements that secure the means against rotation in spaced apart locations within the cavity.

A further aspect of the invention resides in a method of varying stiffness and flexibility, comprising providing equipment (e.g., sports & fitness, medical, footwear & sneakers) having an elongated cavity; imparting stiffness and flexibility variations within the cavity so that the equipment becomes stiffer and less flexible, in one direction than in a different direction, and securing against rotation at least one location within the cavity while imparting stiffness and flexibility variations.

An additional aspect of the invention resides in a resilient shaft or beam acting alone to create variable resistance that incorporates a selectable or adjustable flex resistance by means of varying hand position and placement on the resilient rod in relationship to the fulcrum of the bended rod.

An advantage of the present invention is the ability to provide constant and consistent flex adjustment. This advantage arises from the adjustment being locked in at the ends of the shaft and, depending upon the application, at one or more additional locations through the length of the shaft.

A resilient rod acting alone is also embodied to create resistance that incorporates adjustable flex or resistance by means of hand position and/or specific rotation for means of exercise employing progressive dynamic resistance, which relates to the advantages in exercise of varying degree weight and resistance through a particular cycle.

The present invention embodies flexible materials and devices that form geometries that conformally map or dynamically contour to foot structures in proportion (i.e., ergonomically conform, deform, and/or change shape) to a mechanical setting of a Variable Resistance Beam (VRB) resistance or suspension range settings in balanced proportion to downward foot loading.

In accordance with the principles of the invention, VRBs act as adjustable resistance cantilevers to provide a selectable range of dynamic and reactive suspension to the foot, ankle and lower extremity to bio-mechanically support bone, connective and musculature structures of the foot.

In accordance with the principles of the invention one or more VRBs are applied to orthotic structures to support the foot, for example in the arch. The invention generally delineates one or more VRBs per zone to bio-mechanically affect, support, correct and/or enhance any imbalance of the lower extremity or foot.

In accordance with the principles of the invention, one or more VRBs or zones can be employed to correct and support the bio-mechanical needs of a wearer, a patient, an athlete and/or soldier. Typically one or more VRBs are used to dynamically support the mid arch of the foot and/or in conjunction with up to 4 or more VRBs or zones are employed to positively bio-mechanically correct imbalances or enhance athletic performance of the front right/left and rear right/left sections of the foot.

In accordance with the principles of the invention, a flexible orthotic shell and/or mid arch material (e.g., polymers, copolymer blends, polypropylene, polyethylene, toprelle molded EVA, durometer ranged foams, et al.) with adaptable geometry may be connected to a corresponding VRB to impart selective, reactive and corrective real-time, vertical bio-mechanical support, wherein the VRB may impart increasing or decreasing vertical height to meet the individual's ergonomic arch shape and bio-mechanical arch support requirements.

In accordance with the principles of the invention, the unique biomechanics feature of selectable dynamic suspension coupled to produce a conformal adapting orthotic shell geometry to support the foot in direct proportion to foot loading is called self or auto leveling.

BRIEF DESCRIPTION OF THE DRAWINGS

For a better understanding of exemplary embodiments and to show how the same may be carried into effect, reference is made to the accompanying drawings. It is stressed that the particulars shown are by way of example only for purposes of illustrative discussion of the preferred embodiments of the present disclosure, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 1(a) represents a Type I I-Beam configuration that is substantially circular;

FIG. 1(b) represents a Type II I-Beam configuration that includes a spline;

FIG. 1(c) represents a Type III Dual I-Beam configuration that includes an inner and outer spline;

FIG. 1(d) represents a Type IV Conical beam configuration having cut-out section;

FIG. 1(e) represents a Type V Ellipsoidal beam configuration having a major and minor axis;

FIG. 1(f) represents a Type VI Internal 'I-beam' configuration having an internal spline; and FIG. 1(g) represents a Type VII Rectangular beam configuration.

FIGS. 1A(a)-(c) thru FIGS. 1G(a)-(d) illustrate examples of the resilient rods in accordance with aspects of the embodiment of the invention as shown in FIG. 1(a) thru FIG. 1(g) regarding cross-section, resistance and bending force applied to different hand positions.

FIG. 2A(a)-FIG. 2A(f) Illustrates a comparison of a symmetric or basically round and an asymmetric or elongated cross sectional rod held at two positions.

FIG. 3(a)-FIG. 3(c) illustrates a rod with an outside diameter with marked sets of indicia that specify the range of flexural resistances proportionate to the tensile strength of the beam material and fulcrum length per hand position[s] for symmetric or basically round (1 set) and (2 set) asymmetric or elongated cross sections.

FIG. 18A-FIG. 18F illustrate a second exemplary embodiment of an adjustment mechanism for controlling rotation of a VRB configuration in accordance with the principles of the invention.

FIG. 22A-FIG. 22F illustrate edge views of exemplary configurations of a variable resistance beam in accordance with the principles of the invention, wherein FIG. 22A represents a Type II I-Beam configuration;

FIG. 22B represents a Type III Dual I-Beam configuration;

FIG. 22C represents a Type IV Conical beam configuration;

FIG. 22D represents a Type V Ellipsoidal beam configuration;

FIG. 22E represents a Type VI Internal 'I-beam' configuration; and

FIG. 22F represents a Type VII Rectangular beam configuration.

FIGS. 23A-23E illustrate exemplary indentations within a VRB end, wherein

FIG. 23A represents a triangular indentation;

FIG. 23B represents a square or rectangular indentation;

FIG. 23C represents a pentagonal indentation;

FIG. 23D represents a hexagonal indentation; and

FIG. 23E represents an extended semi-circular (a "D") indentation.

FIGS. 27A and 27B illustrate side views of a second exemplary orthotic platform in accordance with the principles of the invention.

Figure 1A:
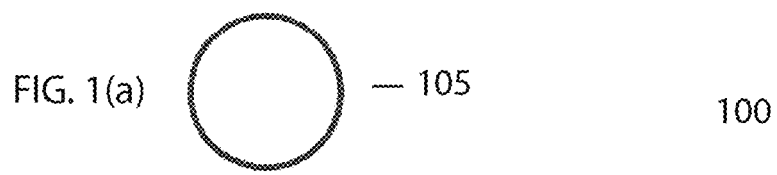
FIG. 1(a)-FIG. 1(g) represents exemplary views and cross sections of resilient rods, beams or shafts of solid, semi-solid or hollow construction in accordance with a first aspect of the invention that produce resistance and variable resistances when orientated in a direction of x, y, z plane or combination of planes in 360 degrees of rotation or bending movement.

It is to be understood that the figures and descriptions of the present invention described herein have been simplified to illustrate the elements that are relevant for a clear understanding of the present invention, while eliminating, for purposes of clarity only, many other elements. However, because these eliminated elements are well-known in the art, and because they do not facilitate a better understanding of the present invention, a discussion of such elements or the depiction of such elements is not provided herein. The disclosure herein is directed also to variations and modifications known to those skilled in the art.

DETAILED DESCRIPTION OF THE INVENTION

The object of the present invention is to adjust the flexibility and thereby the resistance of a rod by hand positioning in relationship to the fulcrum of rod; or by bending a rod and spine within the shaft; or by bending a single solid rod; or both the bending of an outer beam and an inner beam in another example. This affects the longitudinal flex and the kick or hinge point of flexure where maximum flexure bending forces arise, depending on the hand position or anchor point in relationship to the fulcrum.

A shaft includes any tube-like structure by itself, attached to the outside of another surface or incorporated within a structure. Examples of a tube-like shaft by itself include hockey sticks, golf clubs, lacrosse sticks, pole vaulting poles, fishing rods, sailboard/sailboard masts, canoe/kayak paddles or oars, baseball bats, archery bows, tennis racquets and exercise machine tensioning rods. Examples of products to which a tube-like shaft might be attached externally include skis, snowboard bindings and bicycle frames.

A beam or rod includes any solid, semi-solid or hollow elongated structure or rod, wherein the rigidity of the beam or rod is dependent at least upon the thickness of the material constructing the beam and the type of material. In the case of hollow beams or rods, the rigidity of the beam is also dependent upon the thickness of the wall forming the beam or rods and the material constructing the wall.

A spine includes any longitudinal structure whose flexure is different in one plane than another, in any increment of 0 to 90 degrees. This can be achieved using many materials. Examples of design shapes that have this property include, but are not limited to, I-beams, ovals, stars, triangles, rectangles, stacked circles, ellipses, etc. The spine may be solid or hollow in construction and utilize combinations of different materials and material thicknesses to achieve the preferred flexibility profile and characteristics.

FIG. 1 represents exemplary views and cross sections of resilient rods, beams or shafts of solid, semi-solid or hollow construction in accordance with embodiment a first aspect of the invention that produce resistance and variable resistances when orientated in a direction of x, y, z plane or combination of planes in 360 degrees of rotation or bending movement.

FIG. 1 illustrates exemplary embodiments of the invention claimed, wherein;

Type I (FIG. 1(a)): Non-I-Beam: includes a circular cross-section having no outside or internal diameter geometry that would create an i-beam effect: Unlike a single static rod that is intended to produce a single measurement of static resistance, fulcrum adjustable resistance is relative and proportional to hand position as indicated by an indicia zone indicated by graphics, ergonomic ridges, structures, textures and or zones of color.

Figure 1B:
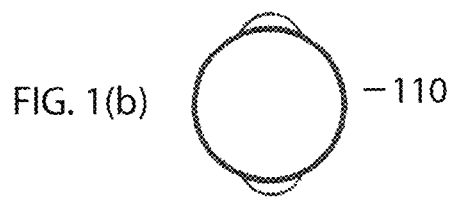

Type II (FIG. 1(b)): I-Beam includes one of: static outside and/or internal diameter geometry or combination, thereof: I-Beam cross section geometry produces proportional adjustable resistance to rotated orientation: Geometric relationship to resistance.

Figure 1C:
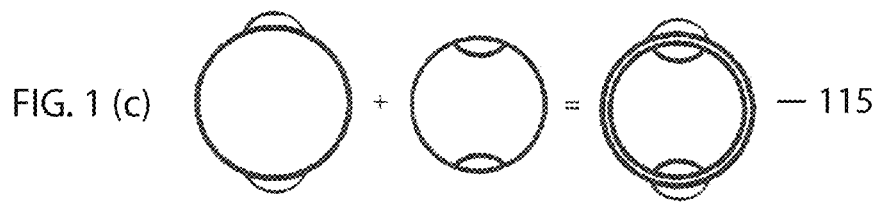

Type III (FIG. 1(c)): Dual I-Beam: includes rotating inner and outer I-Beam tubes with inner and/or outer geometry or combination thereof to create variable I-beam resistance.

Dual I-Beam cross section geometry rotation produces proportional adjustable resistance to the rotated orientation: geometric relationship to resistance.

Figure 1D:
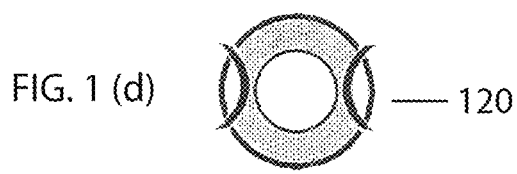

Type IV (FIG. 1(d)): Conical beam with hollow, additive or subtractive wall geometry: Conical Beam cross section geometry produces proportional adjustable resistance to rotated orientation: Geometric relationship to resistance.

Figure 1E:
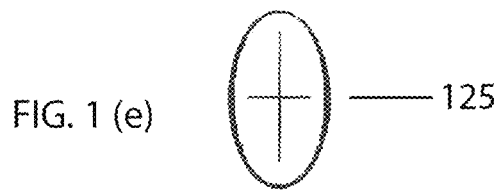

Type V (FIG. 1(e)): Ellipsoidal beam: solid, semi-solid or hollow beam with or without outside and/or internal diameter geometry or combination, thereof along its major axis generating additional I-beam mechanics and/or subtractive, e.g., conical hollow, geometry along its minor axis. Ellipsoidal beam with a major axis that is wider than the minor axis with or without internal or external geometry along the major axis.

Figure 1F:
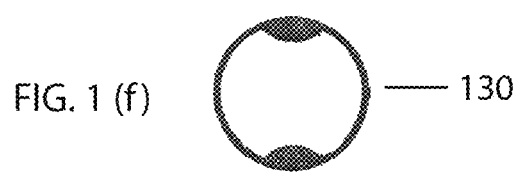

Type VI (FIG. 1(f)): Internal Spine 'I-beam' with one or more spines within a hollow cylindrical or conical shaft.

Figure 1G:
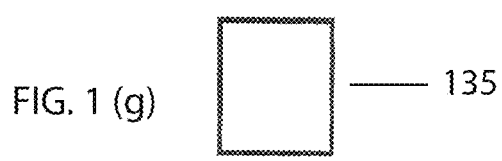
Figure 1A:
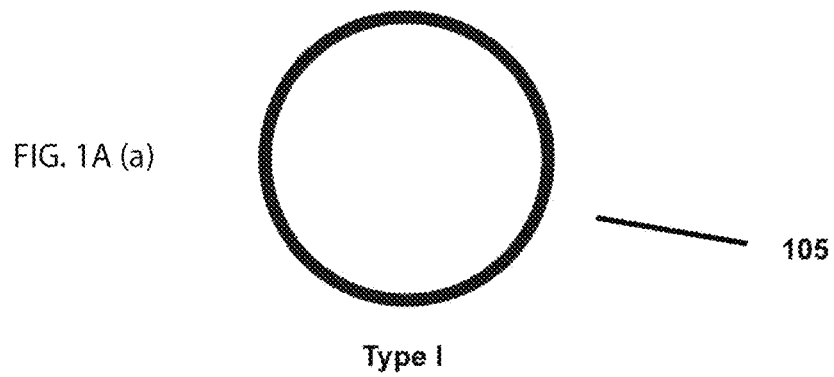
Figure 1A:
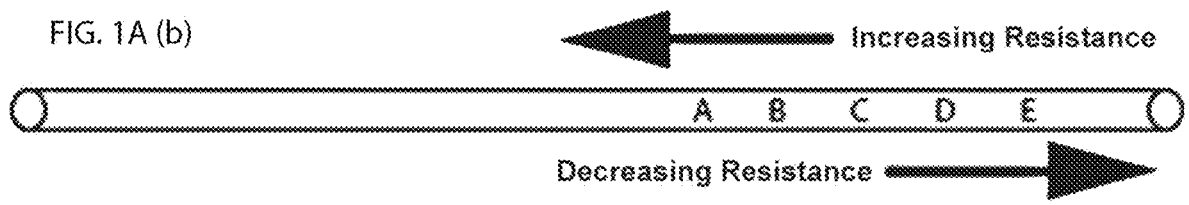
Figure 1A:
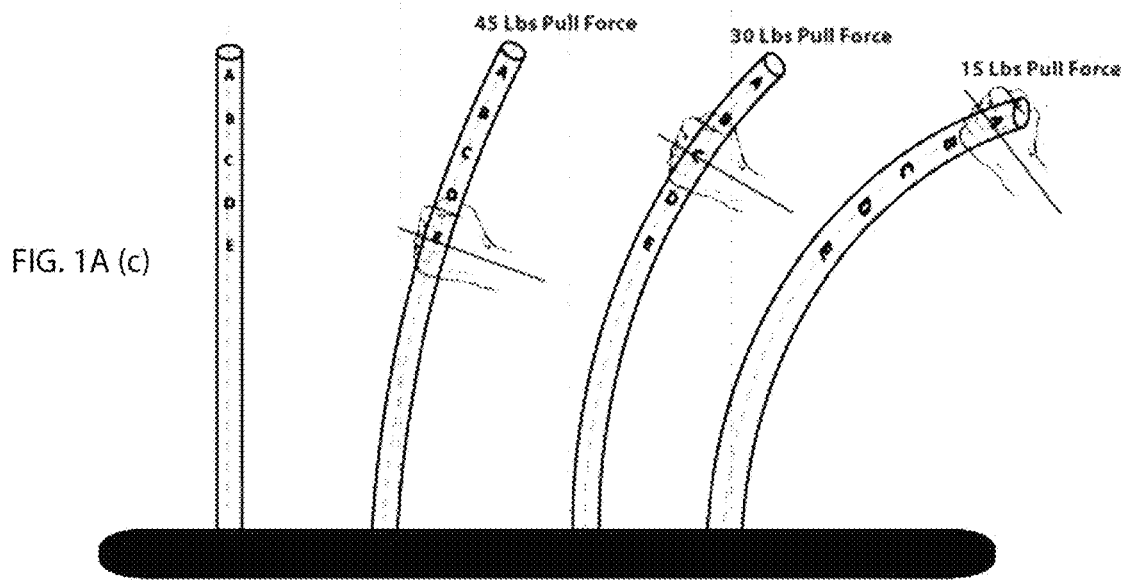
Figure 1D:
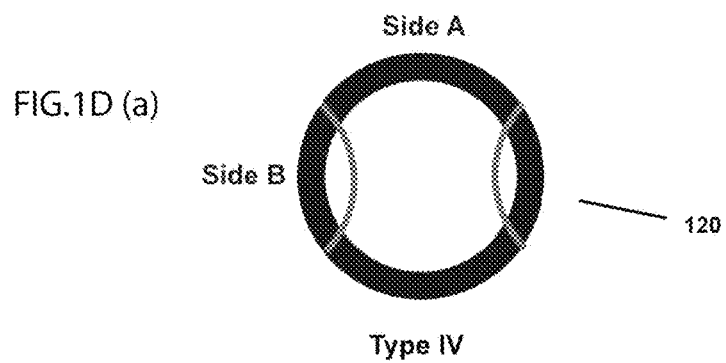
Figure 1D:
Figure 1D:
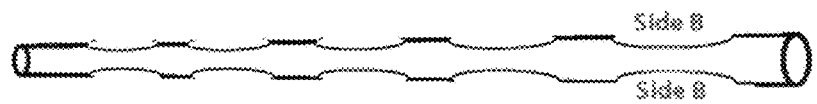
Figure 1D:
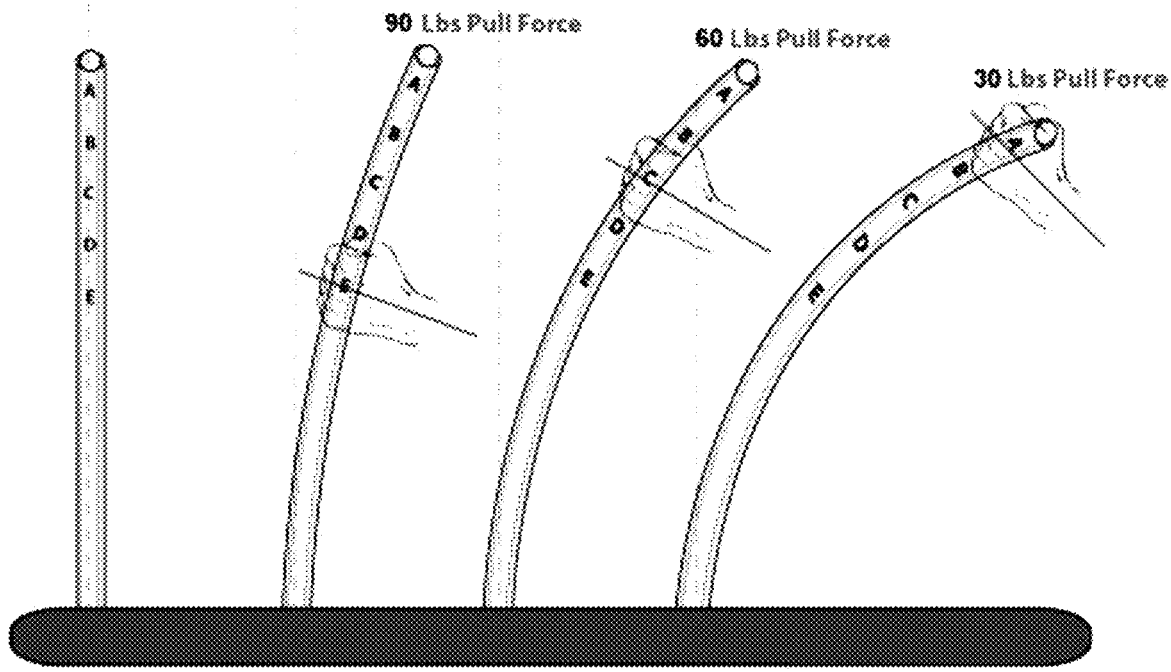
Figure 1E:
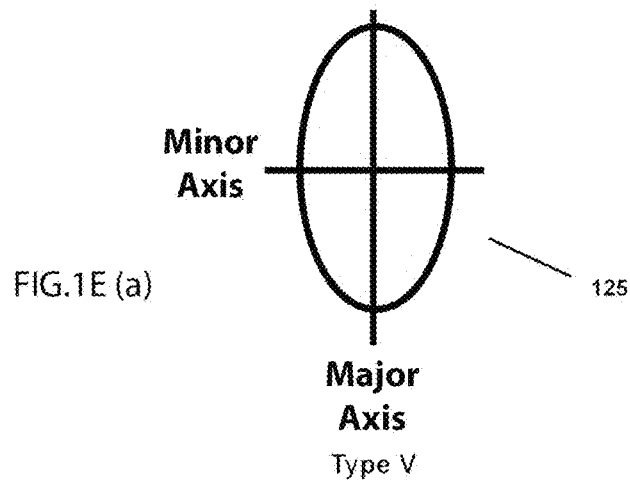
Figure 1E:
Figure 1E:
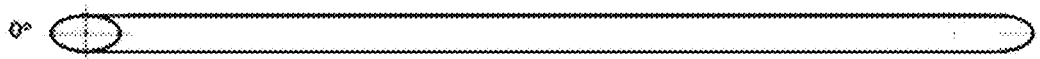
Figure 1E:
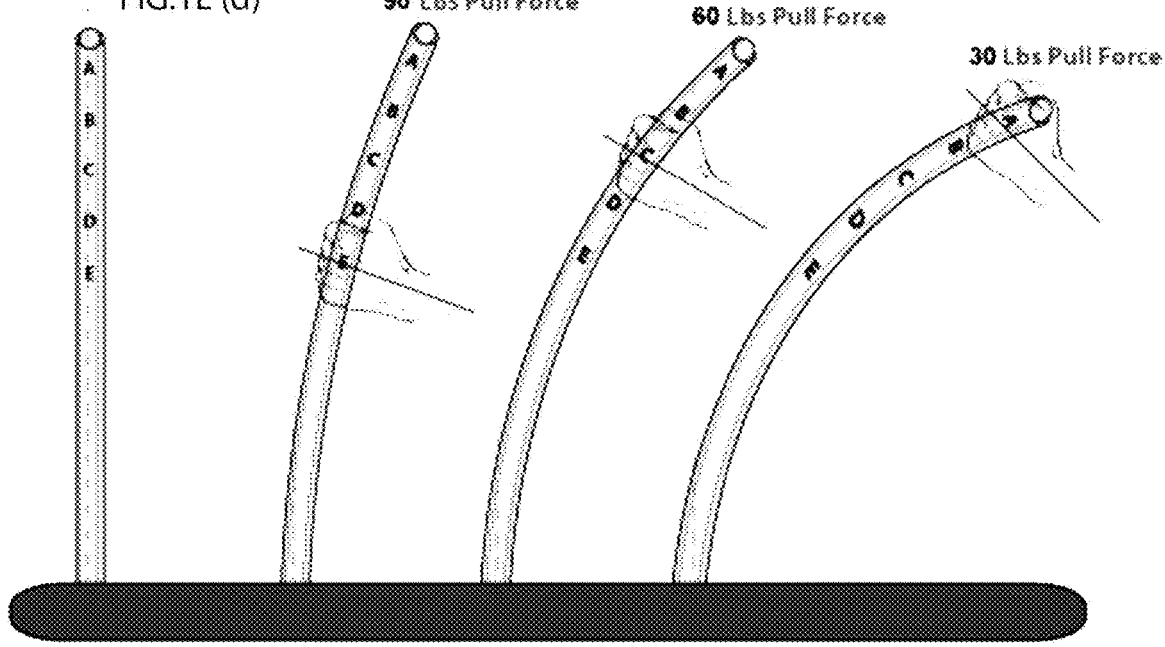
Figure 1F:
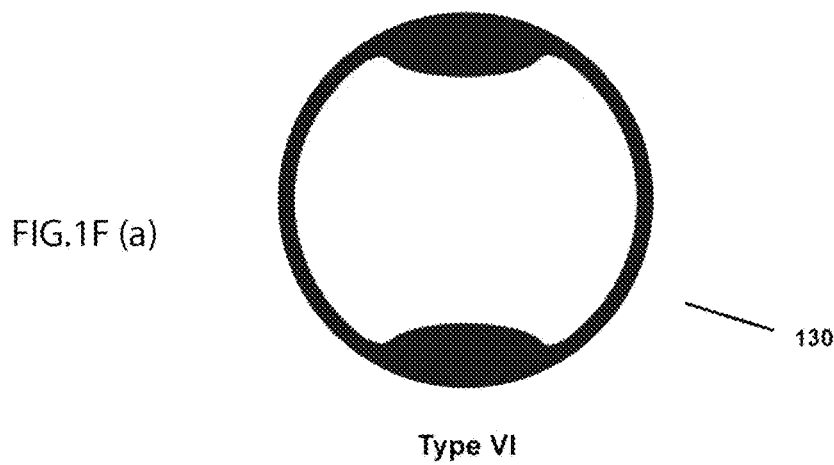
Figure 1F:
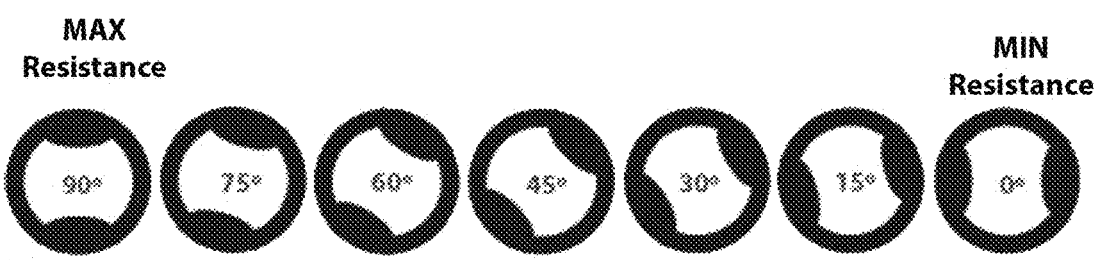
Figure 1F:
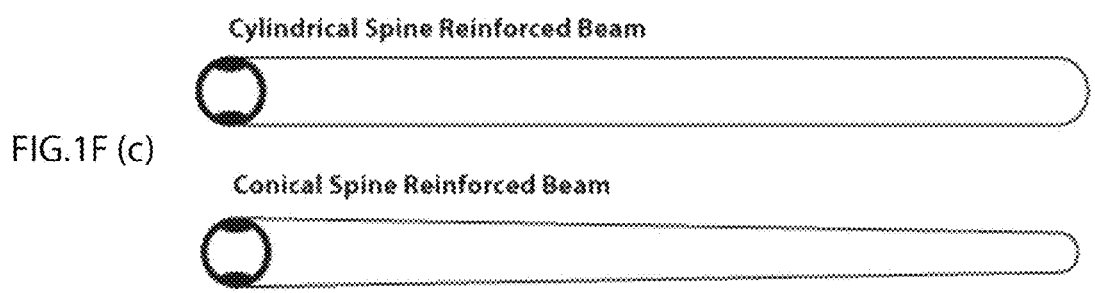
Figure 1F:
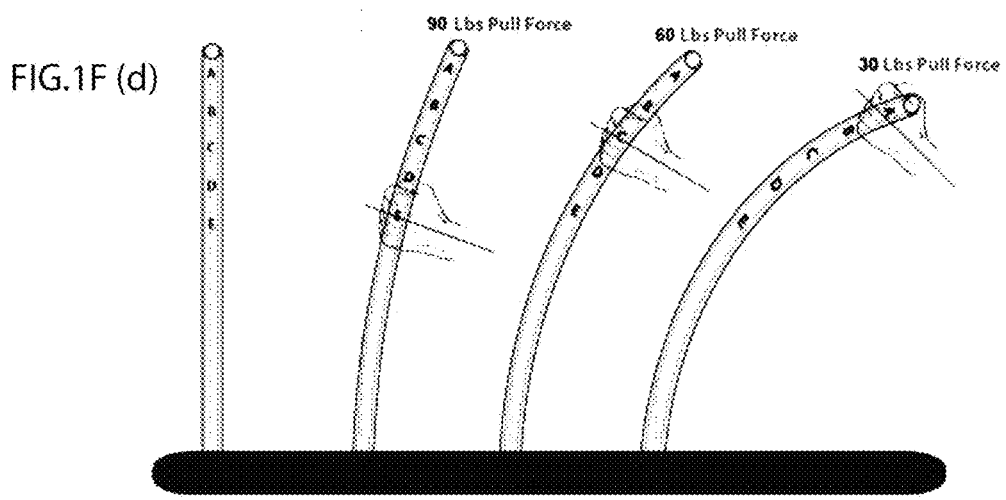
Figure 1G:
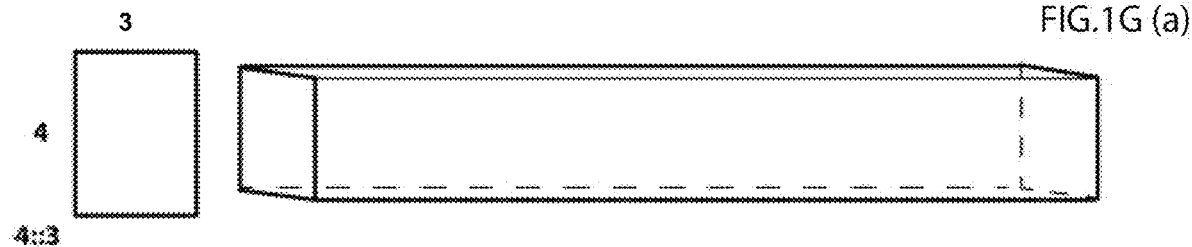
Figure 1G:
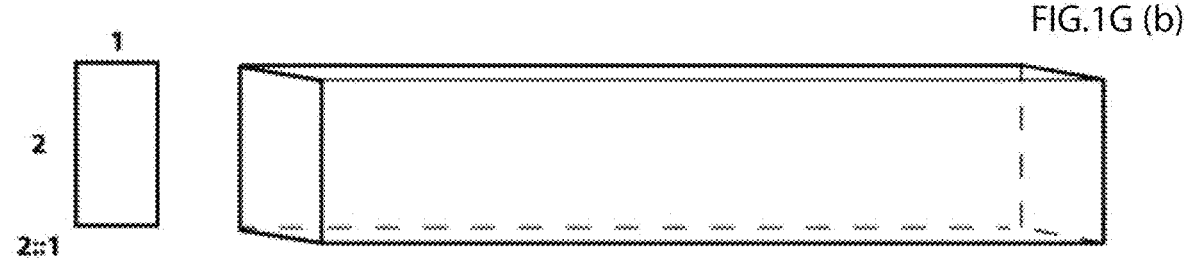
Figure 1G:
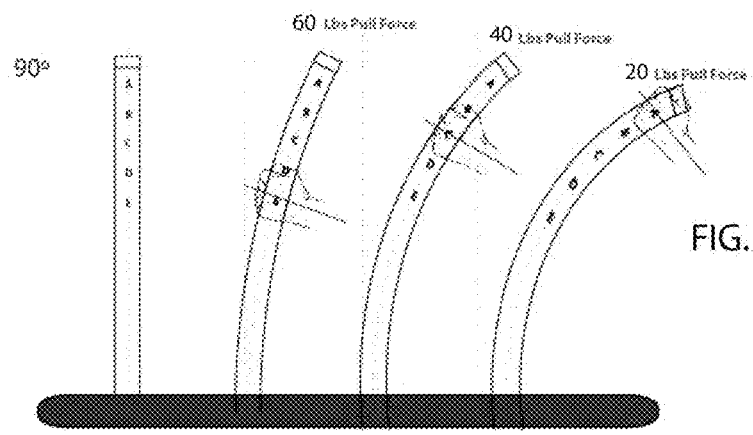
Figure 1G:
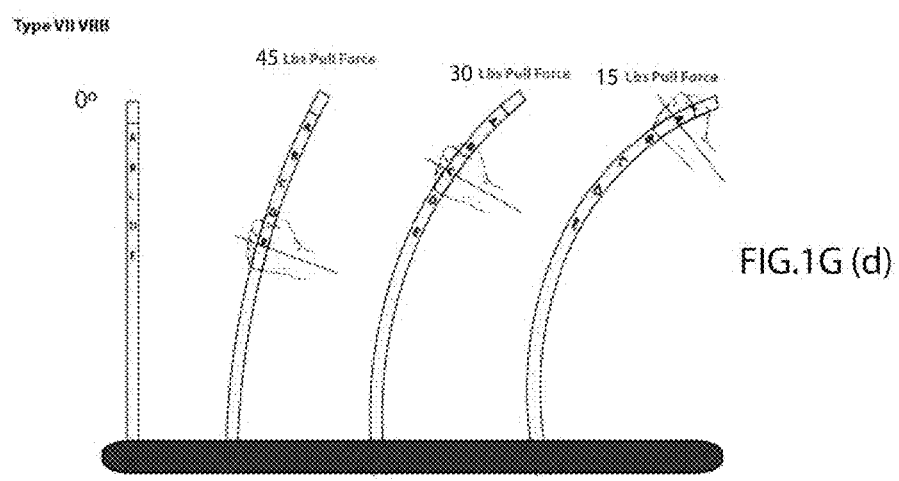

Type VII (FIG. 1(g)): Rectangular beam with two sides wider than the remaining two sides.

More detail description of the different embodiments of the invention are further illustrated in FIGS. 1A(a)-(c)-FIGS. 1G(a)-(c).

FIGS. 1A(a)-(c) illustrate an exemplary embodiment of a type I VRB (variable resistance beam) 100 having a circular cross-sectional area 105. Also illustrated is a series of beams 100 having cross-sectional area 105 that demonstrate the various fulcrum changes through changing hand placement. Each new hand position provides a different resistance such that the resistance increases as a fulcrum length, from a fixed or attached point, decreases, and in the inverse, how resistance decreases as the fulcrum length increases.

FIGS. 1B(a)-(c) illustrate an exemplary embodiment of a type II VRB 100 having a circular cross-sectional area 110 including at least one outer geometric spline 112. Also illustrated is a series of beams 110 with outer geometric spines, demonstrating the various fulcrum changes through hand placement. Each new hand position provides a different resistance. Further illustrated is how the resistance increases as fulcrum length decreases, with respect to a fixed attachment point, and how resistance decreases as the fulcrum length increases.

Also illustrated is a change in the resistance of the VRB 100 having a circular cross-sectional area 110 as the orientation of the outer splines is rotated with respect to a bending force. In this illustrated example, the resistance to the bending force is maximum when the orientation of the outer splines is parallel to the bending force and minimum when the orientation of the outer splines is perpendicular to the bending force.

FIGS. 1C(a)-(c) illustrate an exemplary embodiment of a type III VRB 100 having a cross-sectional area 115 including a combination of an outer shaft having external splines and an inner shaft having internal splines. That is, type III VRB 100 represents a hollow 2-cam cross section. Also illustrated is a series of beams with internal rods or shaft, that have geometric spines, demonstrating the various fulcrum changes through hand placement. Each new hand position provides a different resistance. Further illustrated is how the resistance increases as fulcrum length decreases with respect to a fixed attachment point, and how resistance decreases as the fulcrum length increases. With respect to the fixed attachment point. Also illustrated is a change in the resistance of the type III VRB 100 as the orientation of the inner splines is rotated with respect to a bending force. In this illustrated example, the resistance to the bending force is maximum when the orientation of the inner splines is parallel to the bending force and minimum when the orientation of the inner splines is perpendicular to the bending force.

FIGS. 1D(a)-(c) illustrate an exemplary embodiment of a type IV VRB 100 wherein at least one elliptical section is removed from the cross section 120. In this illustrative example, the reference Side B represents an area within the type IV VRB 100 that is removed from the VRB. FIG. 1D(a)-FIG. 1D(c) further illustrates side views of type IV VRB 100 illustrating the removal of area referred to as Side B from the type IV VRB 100. Also illustrated is a type IV VRB 100, that has elliptical scallop cuts along the inner rod or shaft, demonstrating the various fulcrum changes through hand placement. Each new hand position provides a different resistance, wherein the resistance increases as a fulcrum length decreases, and decreases as the fulcrum length increases.

FIGS. 1E(a)-(c) illustrate an exemplary embodiment of a type V VRB 100 having a cross-sectional area 125 comprising a major axis longer than a minor axis. That is type V VRB 100 illustrates ellipsoidal beams (hollow or solid) with a major axis longer than a minor axis. Also shown is a series of type V VRB 100 demonstrating the various fulcrum changes through hand placement. Each new hand position provides a different resistance. Further illustrated is how the resistance increases as fulcrum length decreases, and how resistance decreases as the fulcrum length increases.

FIGS. 1F(a)-(c) illustrate an exemplary embodiment of a type VI VRB 100 having a cross-sectional area 130 comprising a spine reinforced tubular or conical rod. Also illustrated is a series of type VI VRBs 100 demonstrating the various fulcrum changes through hand placement. Each new hand position provides a different resistance. Further illustrated is how the resistance increases as fulcrum length decreases, and in the inverse, how resistance decreases as the fulcrum length increases.

Also illustrated is a change in the resistance of the type VI VRBs 100 as the orientation of the inner splines is rotated with respect to a bending force. In this illustrated example, the resistance to the bending force is maximum when the orientation of the inner splines is parallel to the bending force and minimum when the orientation of the inner splines is perpendicular to the bending force.

FIGS. 1F(a)-(c) further illustrate that the type VI VRBs 100 may also be of a cylindrical or a conical shape.

FIG. 1G(a)-FIG. (d) illustrate an exemplary embodiment of a type VII VRB 100 beams having a rectangular cross-section 135. As shown the rectangular cross-section may be sized in different ratios (e.g., 4:3, 2:1) to provide different resistance to bending force. For example, in a case of a 2:1 ratio cross sectional area, the resistance to a bending force applied to the greater side is twice as great at that of the lesser side. The rectangular type VII VRB 100 may be solid or hollow as desired.

Additionally, the resistance rods (VRBs) may include a plurality of graduated indicia that indicate bending resistance by measurement of a fulcrum distance from an anchored position to a hand position[s], as shown.

Thus, in one aspect of the invention, rods with symmetrical cross sections vary their bending resistance by shortening and lengthening the arc length, from fulcrum to anchor point by hand position per indicia.

In another aspect of the invention, rods with asymmetrical cross sections may increase or decrease their bending resistance by rotation of the elongated orientation with respect to a bending force, while maintaining the same hand position or fulcrum length.

Figure 2:
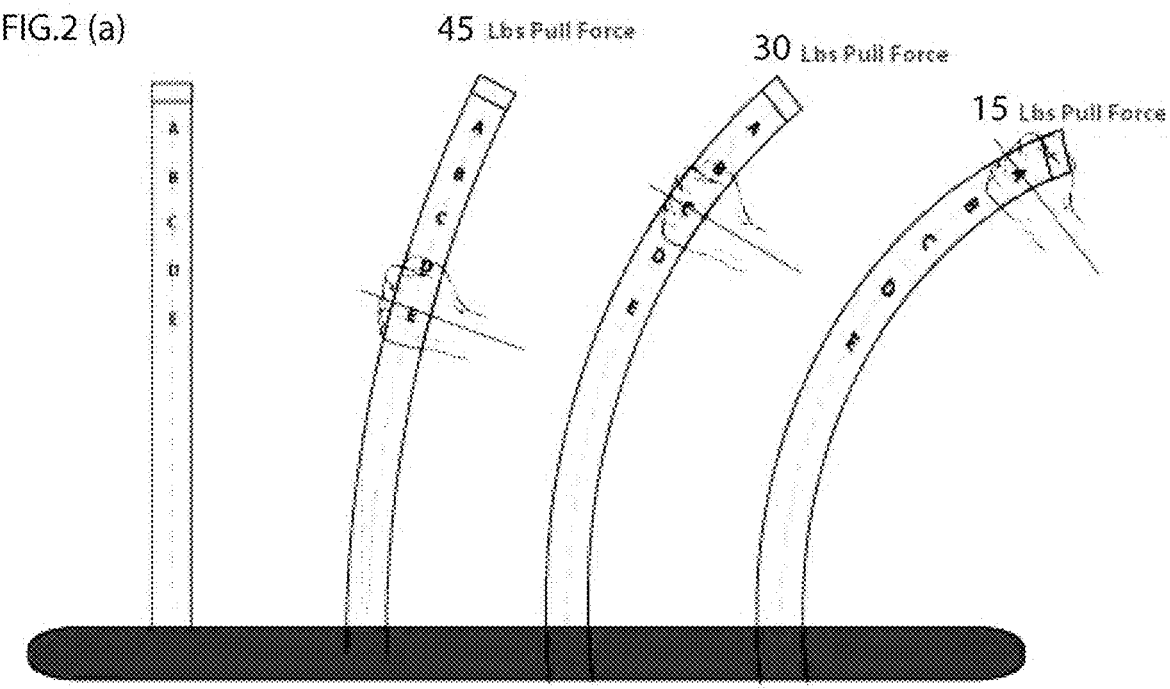
FIG. 2(a) and FIG. 2(b) illustrate a comparison of a symmetric or basically round and an asymmetric or elongated cross sectional resistances generated by each type of rod with the same hand position indicia.
Figure 2:
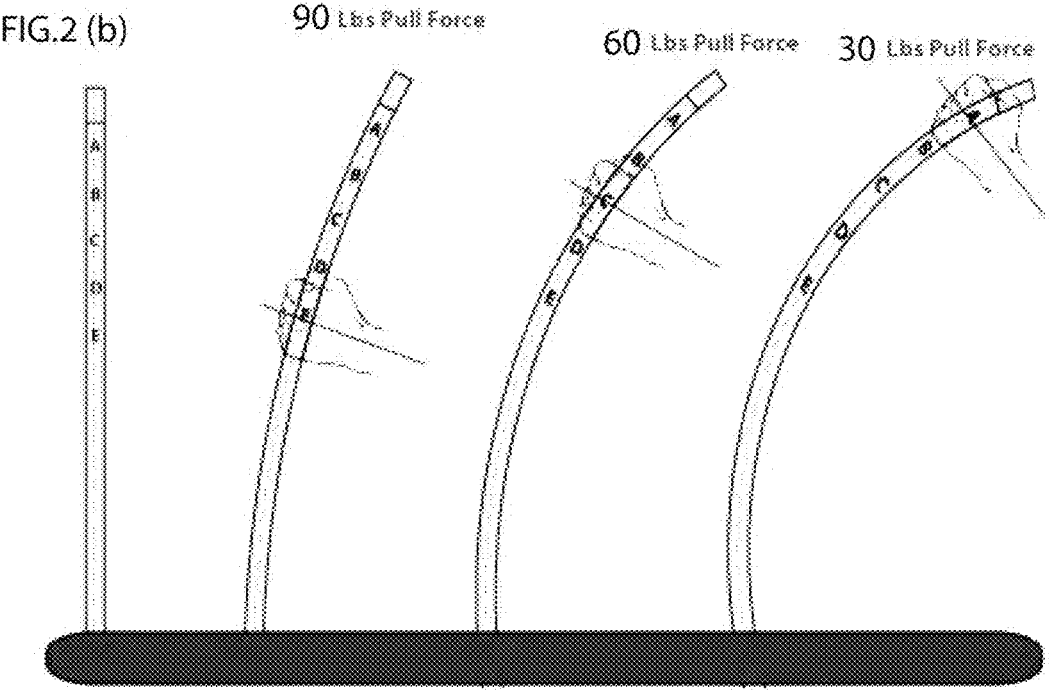

FIG. 2(a) and FIG. 2(b) illustrate the various fulcrum changes through hand placement. Each new hand position provides different resistances. VRB 205 illustrates the variables resistances from a cylindrical beam, rod or bar. VRB 210 illustrates the variable resistances from a type II VRB 100 beam, with added geometric spines, indicating, in this instance, the two-three times increase in pull resistance per identical hand positions along X/Y planes.

Figure 4:
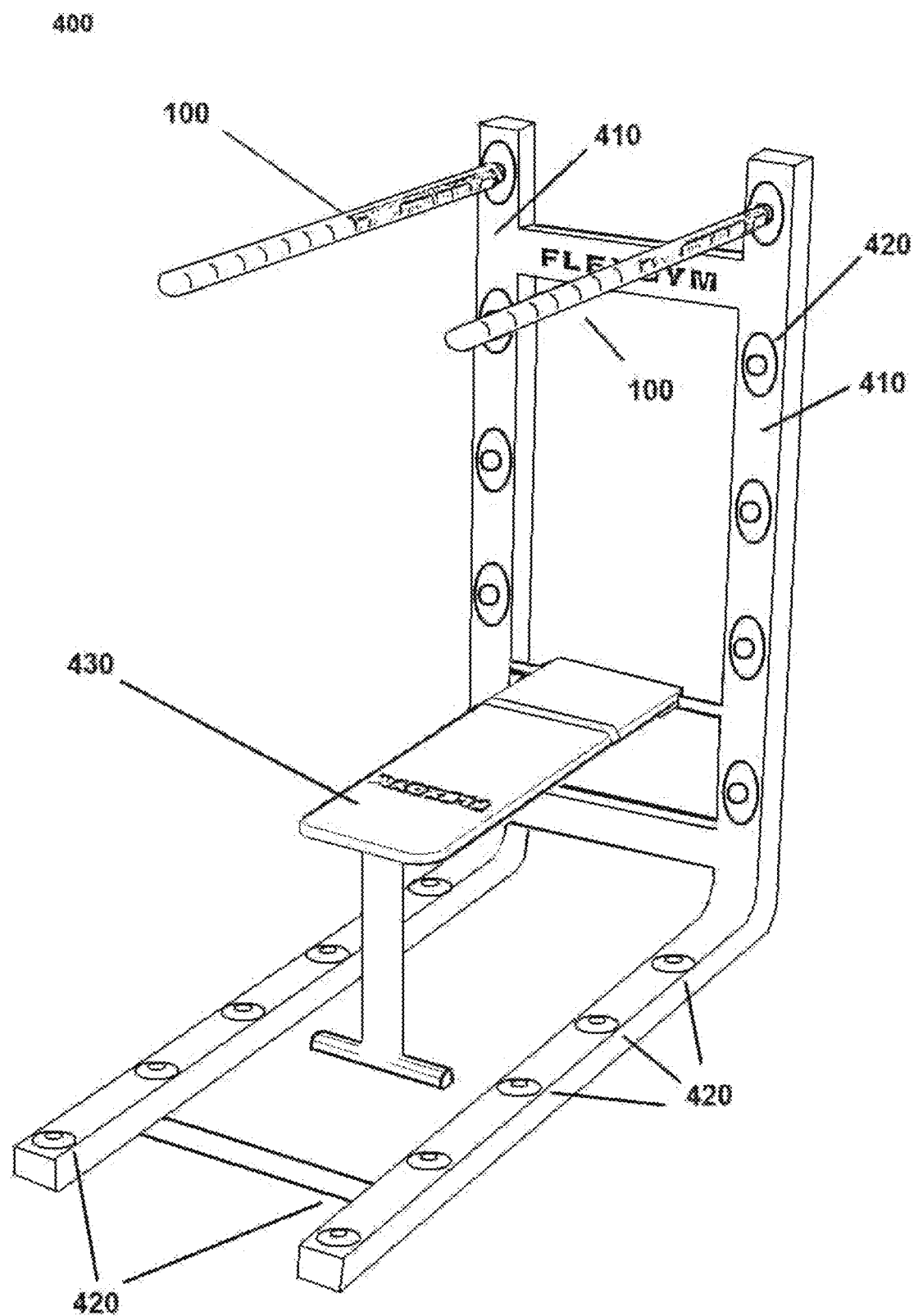
FIG. 4 illustrates an exemplary exercise system configuration in accordance with the principles of the invention that incorporate a plurality of rod holders or anchors affixed along a track or tracks that are designed for the rods to be inserted into and held in place during exercise. The rod holders are designed to increase exercise efficiency by ergonomic utility or facilitate a quick change over of rods that have a higher or lower resistance range.

Table 1 illustrates exemplary resistance levels for different configurations of the VRBs shown in FIG. 1(a) and FIG. 4 for a known material. In this case, resistance levels of VRB of 54 inch length, including 6 grip sections, each grip section being 3 inches for 9/16, 5/8 and 3/4 inch nominal VRBs are determined.

As shown in Table 1, the resistance level increases with the addition of a geometric spine in this example. In addition, by shortening or lengthening the arc length/fulcrum during bending of the beam the resistance may be decreased or increased.

TABLE 1

| Distance from fulcrum | 9/16 inch thick bar | | 5/8 inch thick bar | | 3/4 inch thick bar |
| --- | --- | --- | --- | --- | --- |
| | No Spine | With Spine Min/Max Res | No Spine | With Spine Min/Max Res | No Spine |
| 51 | 7 | 8/15 | 10 | 11/21 | 22 |
| 48 | 8 | 8/16 | 11 | 12/23 | 24 |
| 45 | 9 | 9/18 | 13 | 14/25 | 26 |
| 42 | 10 | 10/20 | 14 | 15/28 | 29 |
| 30 | 11 | 11/22 | 16 | 17/32 | 33 |
| 36 | 12 | 13/26 | 18 | 20/37 | 38 |

Also shown, the resistance level increases as the material thickness increases. In addition, the resistance level increases from a minimum to a maximum value as the orientation of the spine with respect to the direction of the flex increases.

Hence, the resistance level that may be achieved at each hand level depends on the thickness of the VRB and the material composing the VRB. Although not shown it would be recognized that the resistance level may further be based on whether the VRB is hollow. With a hollow VRB, the resistance of the VRB depends on a thickness FIG. 2A(a)-FIG. 2A(f) Illustrates a comparison of a symmetric or basically round and an asymmetric or elongated cross sectional VRB 100 rod held at two positions.

As the fulcrum length or distance between the fixed hand position 215 and the moving hand position 220 increases, the resistance decreases. As the distance between the anchored hand position and the moving hand position decreases, resistance increases.

FIG. 3(a)-FIG. 3(c) illustrate a VRB 100 with an outside diameter with marked sets of indicia that specify the range of flexural resistances proportionate to the tensile strength of the beam material and fulcrum length per hand position[s] for symmetric or basically round (1 set) and (2 set) asymmetric or elongated cross sections.

FIG. 3(a)-FIG. 3(c) illustrate a side view 300 of an exemplary embodiment of a VRB 100 in accordance with the principles of the invention. In this illustrative embodiment, a symmetric VRB 100 may include a plurality of hand positions 315, which indicate one set of resistance ranges in relationship to the fulcrum point. An asymmetric VRB 100, it may include a plurality of hand positions 310, which indicate two sets or multiple levels of resistance ranges in relationship to the fulcrum point and rotated orientation.

FIG. 4 illustrates a view of an exemplary embodiment 400 of an equipment incorporating a VRB 100 in accordance with the principles of the invention. In this illustrative embodiment, a VRB 100 can be inserted into a plurality of insertion points or rod holders 420. The exercise equipment includes a plurality of tracks 410, a plurality of rod holders 420, a bench 430 that may be positioned substantially perpendicular to the plurality of tracks 410 or at an incline angle with respect to the plurality of tracks.

The tracks may be mechanically fixed in vertical or horizontal planes or any combination to maximize rod bend, defined as mechanical work or exercise matched to human proportion or otherwise described as the ergonomic interface.

Figure 5:
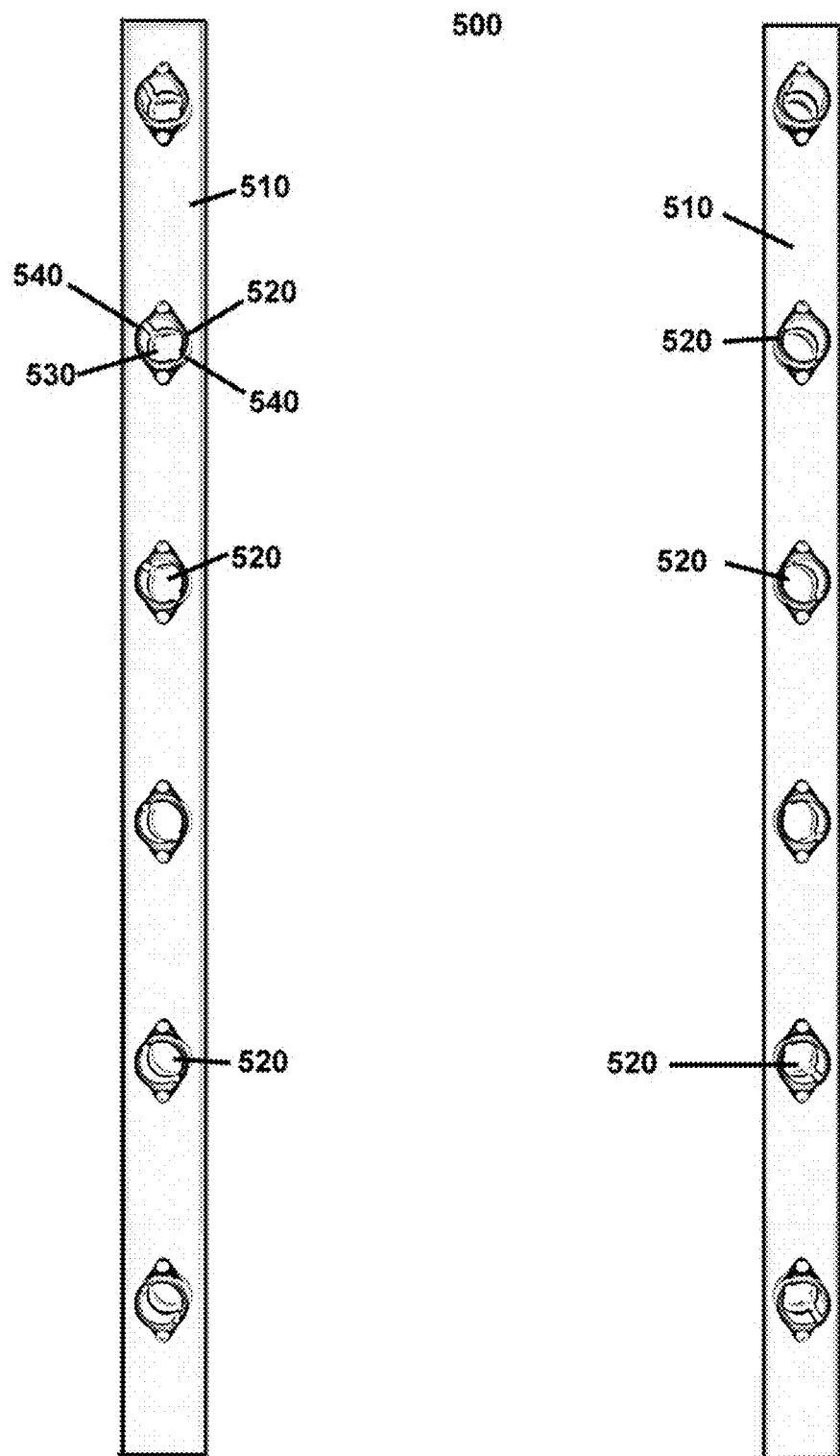
FIG. 5 illustrates an exemplary exercise system configuration of linear rigid tracks affixed with a plurality rod holders designed for the rods to be inserted into and held in place during exercise.

FIG. 5 illustrates a view of an exemplary embodiment of an equipment 500 in accordance with the principles of the invention. In this illustrative embodiment, a VRB 100 can be inserted into a plurality of insertion points. The equipment 510 includes at least one track, which can be wall or floor mounted. Each of the at least one tracks includes rod holders 520. In addition, the walls 530 of the rod holder may be perpendicular or conical with respect to the track 510. Rod holders 520 may further include a stabilizing foot 540 in contact with track 510.

The anchored resistance rod (VRB) generates increased or decreased resistance by anchoring the rod at its base and therefore the user can control the degree of rod bend.

This allows the rod to be used as a dynamic resistance beam for useful exercise. The beam resistance is dependent upon the degree of bend and hand position.

Figure 6:
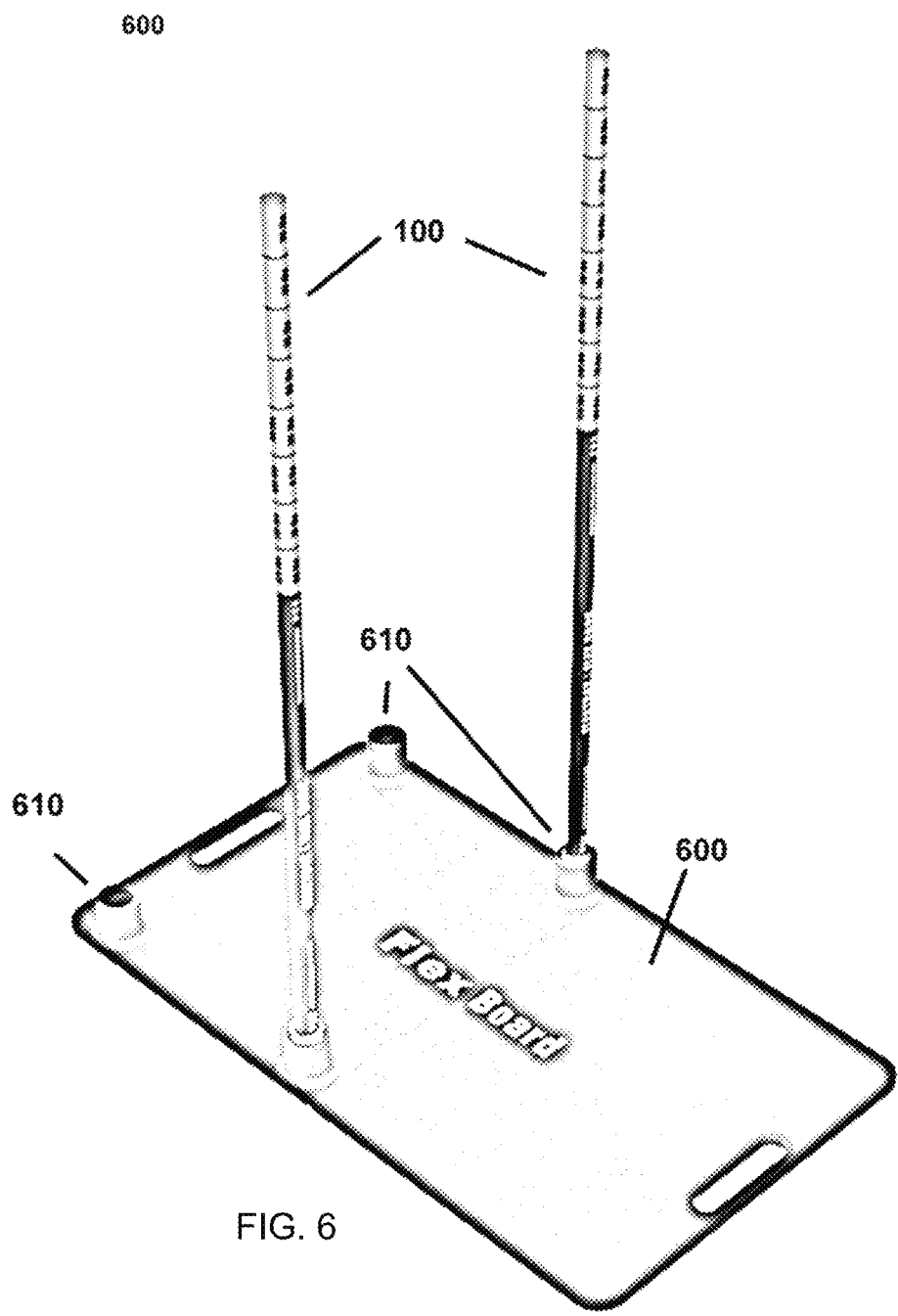
FIG. 6 illustrates an exemplary and portable exercise system configuration in accordance with the principles of the invention comprised of a folding flat workout surface, with a plurality of perpendicular rod holders designed for the rods to be inserted into and held in place during standing exercises.

FIG. 6 illustrates a view of an exemplary equipment 600 in accordance with the principles of the invention. In this illustrative embodiment, a VRB 100 can be inserted into selected ones of a plurality of insertion points 610. In this exemplary embodiment, a plurality of perpendicular rod holders or insertion points 610, similar to those described with regard to FIG. 5, may be incorporated onto a handheld transportable folding workout platform 600.

Figure 7:
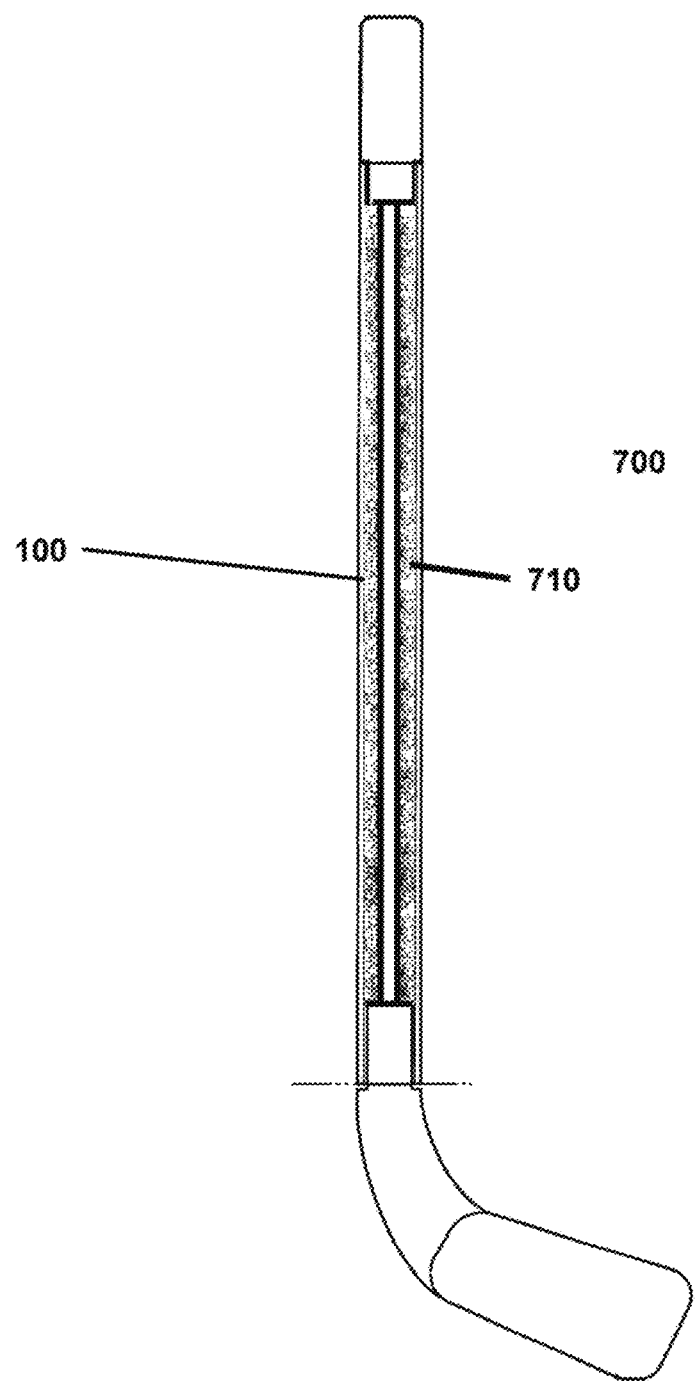
FIG. 7 illustrates an exemplary sports equipment configuration for a resistance beam centrally located within a solid wooden or hollow aluminum or graphite shaft of a hockey stick in accordance with the principles of the invention.

FIG. 7 illustrates a view of an exemplary equipment 700 in accordance with the principles of the invention. In this illustrative embodiment, a VRB 100 held in place by foam or other lightweight material 710 within a hollow shaft 720. The position and/or orientation of the VRB 100 within the hollow shaft 720 may determine the stiffness and/or flexibility of the hollow shaft. That is, in the case, a type I VRB 100 is incorporated into the hollow shaft 720, the length of the type I VRB 100 may determine the stiffness of the hollow shaft. On the other hand, if a type II VRB 100 is incorporated into the hollow shaft, then the orientation of the splines to a proposed bending force determines the stiffness and/or flexibility of the hollow shaft 720.

The resistance beam upon manual customized selected rotation imparts greater flexibility or rigidity to the hockey stick by the user, to customize the equipment's response to the user's athletic ability.

Additionally, another method of imparting greater flexibility or rigidity is to raise or lower the resistance beam within the shaft to change the fulcrum or kick point of the stick.

Figure 8:
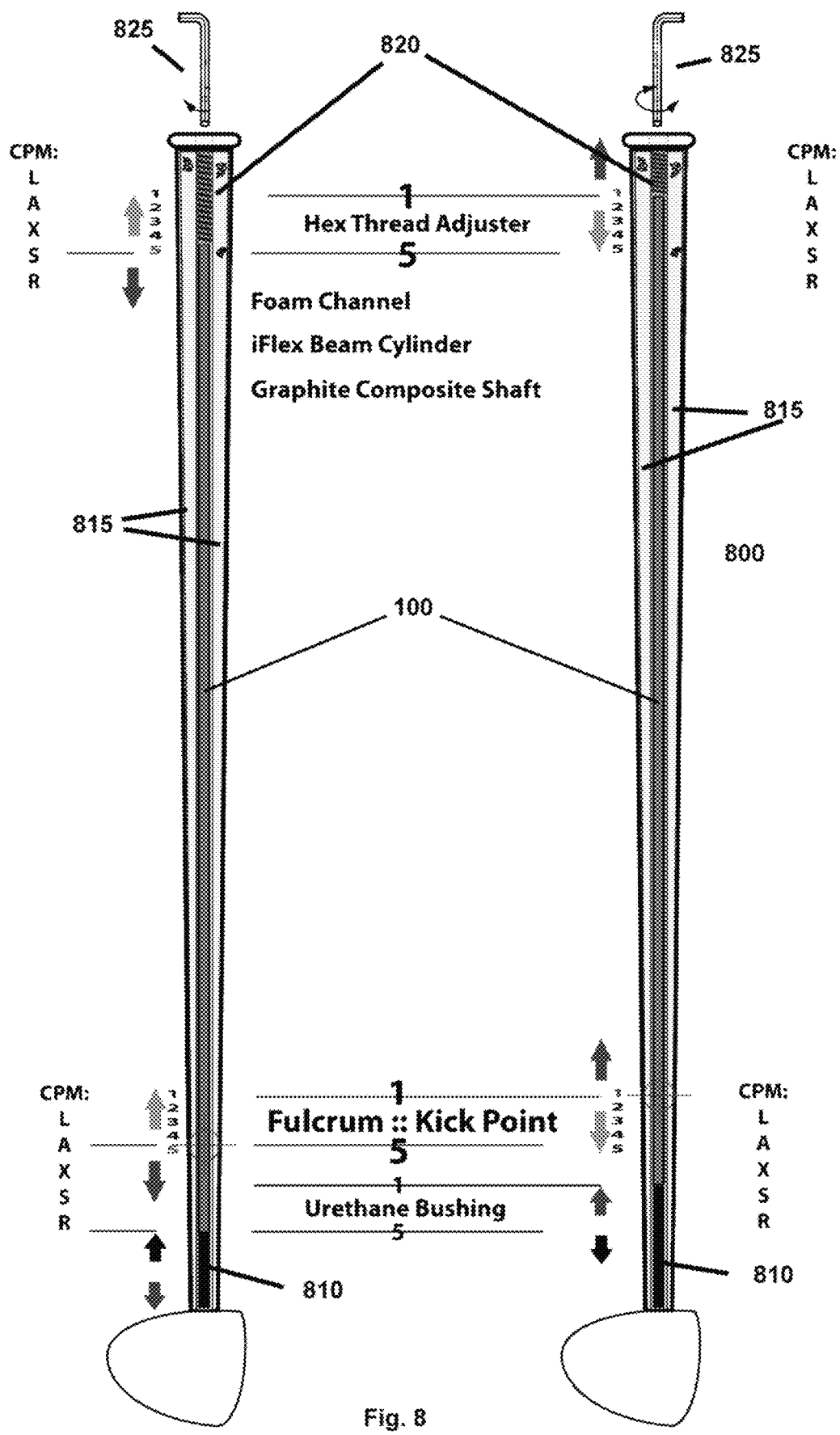
FIG. 8 illustrates an exemplary beam mechanically positioned centrally within a golf shaft configuration in accordance with the principles of the invention.

FIG. 8 illustrates a view of an exemplary embodiment of an equipment 800 in accordance with the principles of the invention. In this illustrative embodiment, an internal VRB 100 is held in position within a hollow shaft by a lightweight material 815, as described with regard to FIG. 7. In addition, one end of the VRB 100 is positioned on a bushing 810 comprising a flexible material such that it may compress or expand as pressure is applied to the bushing 810. In one aspect of the invention, the bushing may be made of an elastometric material such as a polymer, foam, urethane, rubber, or so the similar material that may be compressed and returned to an original state when the compressive force is removed. At a second end, the VRB 100 is attached to a means 820 for raising or lowering the VRB within the hollow shaft. The means 820 may be a worm gear type mechanism that raises or lowers the VRB 100, to create a variable shaft flex. The VRB 100 may be lowered by compressing the bushing material 810 and raised by removing the compression pressure from the bushing material 810. Although the means for positioning the VRB 100 is shown as a worm gear that may be turned by an Allen key, it would be recognized that other types of rotating means may be incorporated without altering the scope of the invention. For example, the means for adjustment to alter the position of the VRB 100 may be a screw thread position along the outside of the hollow shaft and the turning of a cap on the top of the hollow shaft may lower or raise the VRB 100.

In the illustrated embodiment of the invention shown herein, a VRB 100 rod is centrally raised or lowered within the hollow shaft to increase or decrease flexibility or rigidity of the golf shaft, thereby shifting the kick point or maximum point of flexure up or down the hollow section of the shaft.

Thus, the player or user may select a shaft flex or rigidity range that matches the player's specific swing type, strength and ability.

The 360 degree symmetrical geometry provides a solution for an adjustable golf club and would be fully compliant with the existing USGA (United States Golf Association) rules of golf.

Figure 9:
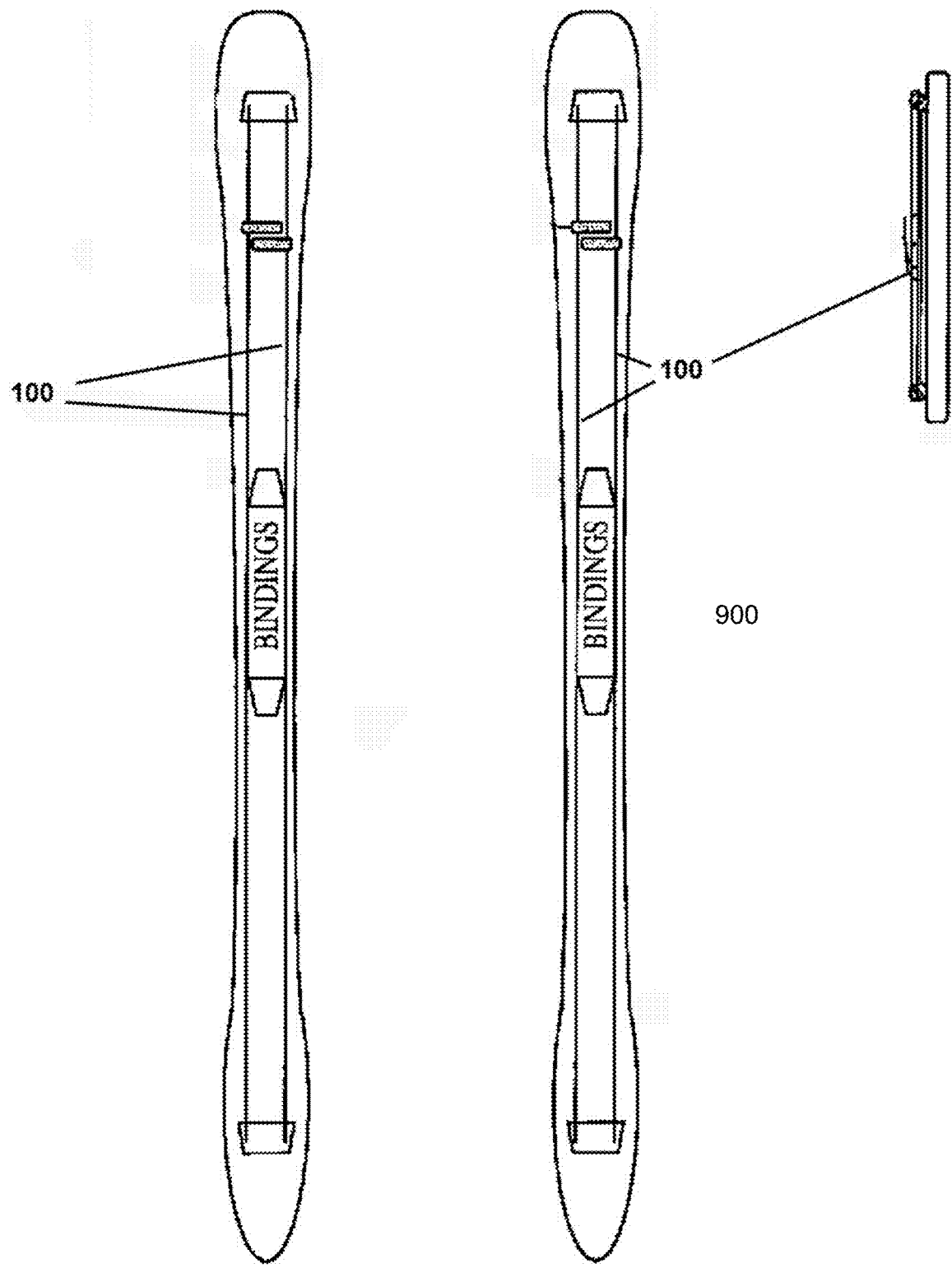
FIG. 9 illustrates an exemplary ski sports equipment configuration with an adjustable resistance beam that imparts a resistance range along the length of the body of the ski in accordance with the principles of the invention.

FIG. 9 illustrates an exemplary ski sports equipment configuration 900 with an adjustable resistance beam VRB 100 that imparts a resistance range along a length of the body of the ski in accordance with the principles of the invention.

The adjustable resistance beam VRB 100 imparts a range of performance characteristics into the ski to match the skier's skill and terrain requirements.

In one application of the VRB described herein, downhill skiing requires a very rigid ski. By adjusting the resistance beam to the highest rigidity setting, the ski will become more rigid with a faster dynamic response when carving turns. A more rigid ski is desirable for icy conditions due to the ability to hold its shape and maintain maximum edge contact with the snow and ice surface.

In another application, mogul skiing over bumps requires a flexible ski. By adjusting the resistance beam to its most flexible setting, the ski will become more conformal to bumps and bend and flex over them.

Thus a terrain adaptable ski is created from a mechanically joined adjustable resistance beam.

The means for positioning the VRB 100 may be similar to that described with regard to FIG. 8.

Figure 10A:
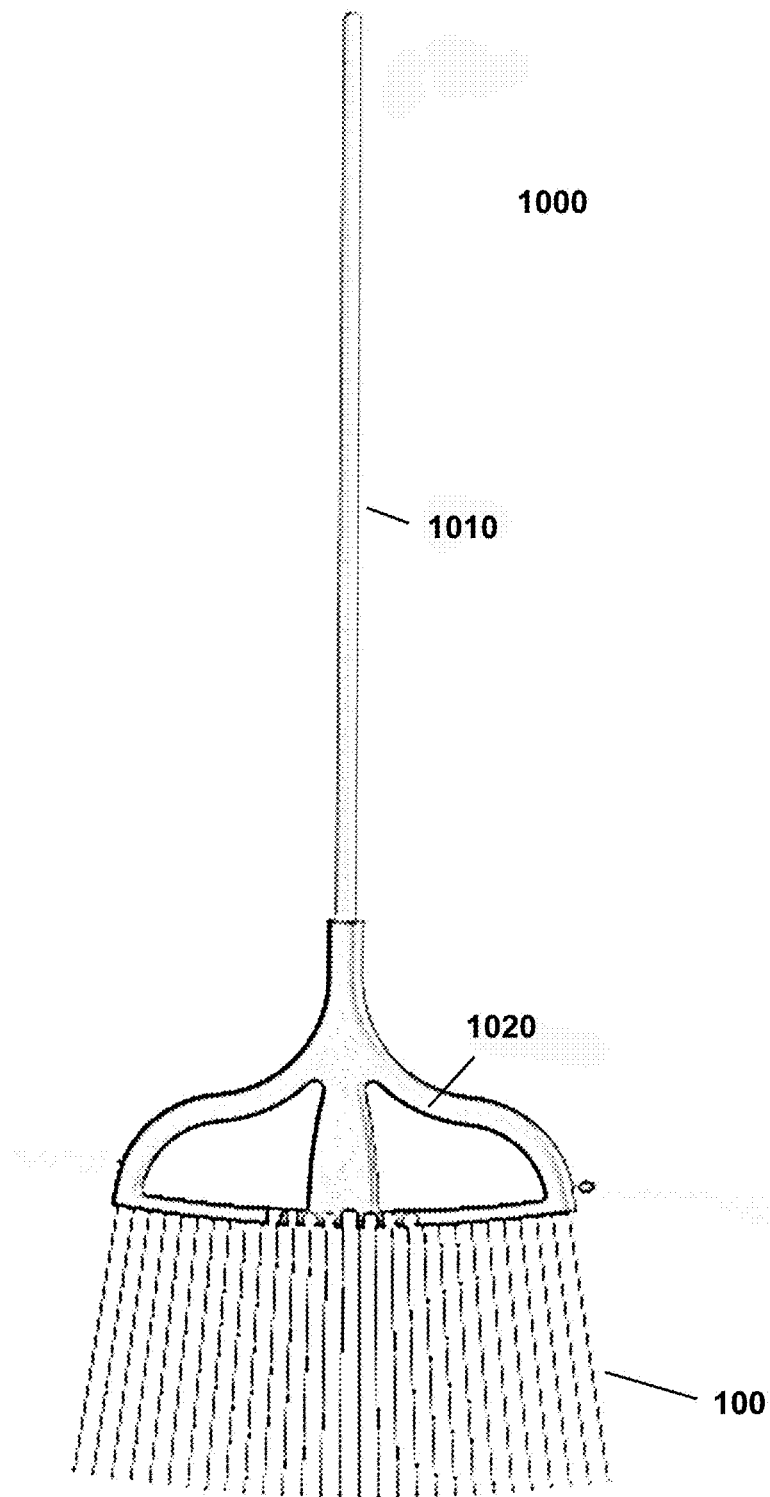
FIG. 10A-FIG. 10B illustrate exemplary configurations of a lawn device configured in accordance with the principles of the invention. The tines of this adjustable flex rake are individual resistance beams that are simultaneously rotated.

FIG. 10A illustrates a view of an exemplary embodiment of a lawn equipment 1000 in accordance with the principles of the invention. In this illustrative embodiment, tines are individual VRBs 100, and can be simultaneously adjusted to create equal flex in each tine.

Figure 10B:
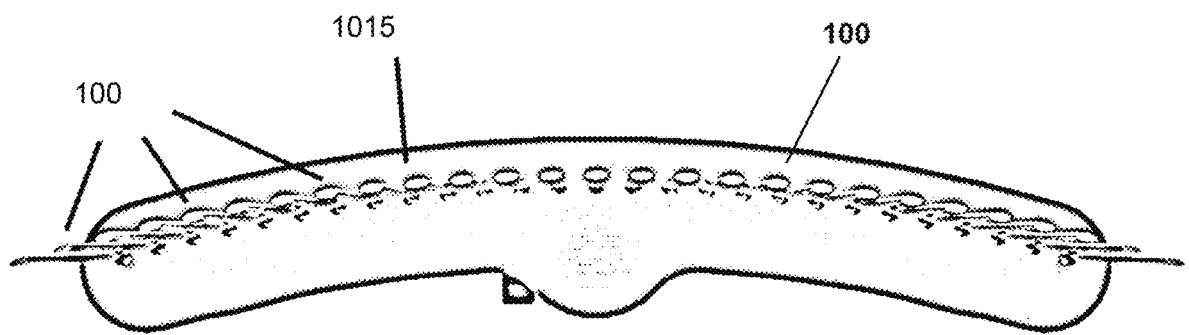

FIG. 10B illustrates a bottom view of an exemplary embodiment of a lawn equipment 1000 in accordance with the principles of the invention. In this illustrative embodiment, the tines VRB 100 may be simultaneously rotated equally to create variable flex.

The rotated tines are locked into an incremental range of resistance positions that are either the most flexible for raking leaves or the most rigid to raking gravel. At the end of each tine is an ellipse that acts a hook dependent upon its rotated orientation.

Figure 11:
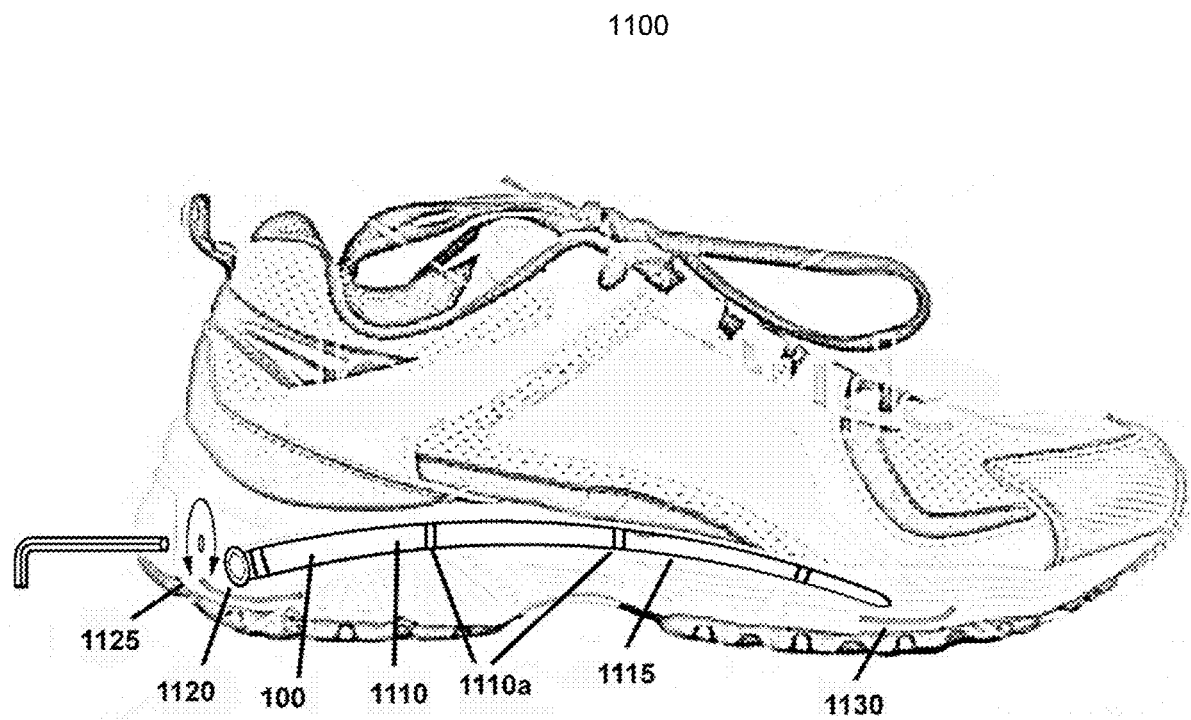
FIG. 11 illustrates an exemplary adjustable active suspension system configuration for sports footwear in accordance with the principles of the invention.

FIG. 11 illustrates a view of an exemplary embodiment of an equipment 1100 in accordance with the principles of the invention. In this illustrative embodiment, internal VRBs 100 are adjusted to create a variable flex. Equipment 1100, which represents an athletic shoe, includes a rubber shoe sole 1115. The athletic shoe 1100 further includes a heel fulcrum 1125 and a toe fulcrum 1130. Between the heel fulcrum 1125 and the toe fulcrum 1130 is an internal cavity 1110. Within cavity 1110 is positioned at least one VRB 100. The VRB 100 includes anti-rollover collars 1110a, which prevent the VRB beam deflection or distortion and are spaced along the VRB 100. The at least one VRB 100 located within the internal cavity 1110 may be adjusted by an adjustment means 1120 that rotates the VRB within cavity 1100. The VRB 100 is further locked in position. The means for positioning the VRB may be similar to that described with regard to FIG. 8.

The transmission of the shoe wearer's strength (power) from their legs into the ground is directly affected by the sole stiffness of the shoe. By employing an adjustable resistance beam as described herein, runners may gain more leverage and, thus more speed, by using a responsive shoe sole customized to their specific requirements.

An adjustable pair of resistance beams within the shoe sole may be insertable, insert molded or structurally connected to the shoe sole in lateral and/or longitudinal positions within the sole and are rotatable to a fixed and mechanically locked position to effect custom flexural resistance range that matches the wearer's optimum performance requirement.

Thus, the resistance beam technology described herein is designed to be a dynamic, adjustable, in-sole suspension system that can absorb the weight of the wearer and release it per each step.

In accordance with the principles of the invention, a VRB orthotic support system to provide selectable arch support may be incorporated as in-sole orthotic device to provide adjustable and dynamic geometry to support the structures and or additional quadrant zones of the foot is disclosed.

The orthotic arch platform supports the zones of the foot from the VRBs dynamic, reactive, selective resistance to loading, resulting in dynamic suspension per one or more zones, e.g. mid arch, et al., providing vertical lift from the VRB cantilever to maintain physiologic support with bio-mechanic balance and comfort.

The orthotic platform effectively maps the differential loading points with resistance or suspension levels of the foot per zone and compensates with reactive support that can be selectively increased or decreased to match any podiatry foot condition or performance enhancement for sports or extreme physical activity, e.g. military, where the wearer's loads are often variable.

The orthotic platform acts as a type of selectable leaf spring suspension or in multiple zones, a cat's paw or multi-zone cantilever in the shape of an 'X' to combine variable resistance settings and/or height geometry from VRB dynamic suspension. This reactive system vertically 'reacts' or lifts body weight loads placed upon its surface per zone, to maintain and respond to proportionate bio-mechanical foot balance loading and therefore comfort or pain relief, with athletic enhancement.

In conjunction with a 'dedicated mid arch zone or individual VRB arch structure is integrated with the footwear cat's paw or X platform with up to 4 VRBs to create a completely multi-zone adjustable and dynamically supportive orthotic foot device. The orthotic device may take a product form of a stand-alone shoe insert, integrated (i.e., overloaded or insert molded into the sole of the shoe or boot) and/or be partially captured or molded into the shoe or boot sole.

The reactive, dynamic and selective support levels of the orthotic zones with VRBs are a function of the VRBs inclination angle, length and width, material tensile strength or fulcrum position in relation to the underside of the foot loading, and/or extension from within shoe sole. Additionally, selectable resistance in conjunction with different variable orthotic shell geometries provides a wider prescriptive resistance range to match heavier bodyweights, severe infield operating requirements, and/or corrective foot conditions.

In accordance with the principles of the invention, at least one VRB is attached, typically inclined, to the underside of the mid arch to impart dynamic suspension or to reactively support the compressive loads of the foot. The orthotic platform and mid arch flex with the VRB so as to provide responsive dynamic and zoned suspension support with conformal geometry mapped to foot loading. The arch platform maximizes surface area by distributing loads over a greater area, with a responsive and dynamic conformal surface to support the loads in real time and proportion.

Additionally, by extending the length of one or more VRBs, the VRBs become extendable into one or more of the 4 quadrant zones of the shoe to impart selectable dynamic responsive support to the bio-mechanic loads placed upon the arch platform. A single VRB may act as a dual cantilever to support two different support zones or structures, e.g. a VRB may support the foot arch and rearward heel zone by one or more fulcrums or 'stops' placed along the VRB length to impart calculated, and therefore, selectable cantilevered suspension to dual zones.

In accordance with the principles of the invention, a VRB acting as a cantilever provides dynamic arch support over a selectable range to match a wearer's biomechanics corrective requirement with comfort. If a prescriptive setting is initially too stiff, hard or uncomfortable for the wearer, a lower VRB setting may be used to allow the wearer 'break-in' time for re-alignment processes of the foot structures to correct, thus maximizing comfort with prescriptive benefit and enhanced customized athletic performance.

Additionally, one or more VRBs are extendable into each of the 4 quadrant zones of the shoe to impart selectable dynamic responsive support to reduce the 'break-in' period for the shoe, increasing comfort.

The VRB selectable support range provides for a range of loads that controls the supportive flexure of an orthotic shell or footwear, specifically the mid arch geometry. This in turn provides reactive arch geometry that will flex in proportion to the VRB setting and therefore impart dynamic arch support proportional to loading.

In accordance with the principles of the invention, the zone loading and/or mid arch loading and, therefore, the VRB loading curve[s] or the quantified in vertical lift force in pounds (Lbs) of response to weight loads placed on the VRB extending into each shoe zone or mid arch shell structure are bell curved. The bio-mechanic effect of a cantilever absorbing and releasing proportional loads in a Bell Curve results in maximal comfort throughout the entire gait cycle and at each VRB resistance setting. This is an important and intended integral design engineered bio-mechanic effect of using cantilevers to dynamically support body joints, e.g. foot et al., to provide a smooth bell curve response for maximal comfort throughout the flexural VRB range.

The mechanical resistance or support of the VRB can be design engineered to correspond to any required loading curve, e.g. rehabilitative, post-surgical, prophylactic, extreme sports, performance enhancement and the military for high rucksack equipment loading in pounds (Lbs.). Equally, more robust VRBs can be easily incorporated into an orthotic device to support the arch from heavy equipment loads carried via rucksack, e.g. 100 Lbs. or more.

In accordance with the principles of the invention, responsive, proportioned and dynamic zone(s) of support create a self-levelling structural orthotic shell for the foot, enhancing the wearer's athletic ability or dynamically correcting imbalances. This provides a real time, proportionately customizing orthotic to support the load requirements of the foot.

The greater the load upon the foot, the greater VRB vertical suspension or resistance to compression by immediate vertical (dynamic height) lifting support. The self-leveling platform matches the dynamic loads placed upon the zones of the foot/arch in proportion to load. The VRB compression and release of load results in proportional, vertical lifting support to the arch of the foot or per zone.

The arch and zones are supported by one or more VRBs that dynamically react in direct proportion to the loads placed upon them. The orthotic shell is 'pre-loaded' or at a higher height geometry to allow the foot to engage and proportionally compress and engage the VRB zones (mid arch, et al.) of support levels to ensure a mapping of supported structure with cantilevered resistance ranges. Each individual zone is selectable with customizable suspension range.

In accordance with the principles of the invention, the VRB technology, disclosed, herein, dynamically supports the loads of the mid arch, to stabilize pronation and supination mechanics, by providing customizable, dynamic, cantilever based suspension ranges with one VRB under the mid arch area or up to four or more cantilevered VRB zones of selectable resistance, to further support and correct bio-mechanical imbalances of the foot.

The orthotic platform, disclosed herein, combines dynamic vertical mid-arch support with variable geometry through a flexible orthotic shell that adjusts to each height and resistance or suspension setting from a single VRB or up to four or more zones with selectable resistance cantilever. The shell acts as a dynamic suspension surface to vertically react or lift body weight loads placed upon its surface and to maintain proportionate bio-mechanical foot balance and therefore comfort and pain relief.

The mid-arch support variable geometry levels are a function of VRB inclination or other mechanical methods of providing selectable height to adjust the mid arch position of the orthotic blade, to lift or support the bodyweight proportionate to foot loading. Additionally, selectable resistance in conjunction with variable shell geometry to provide prescriptive resistance ranges to match bodyweight and corrective foot conditions.

The orthotic system disclosed herein provides a lightweight, variable resistance of support to proportionally counter act body weight placed upon the foot to dynamically maintain bio-mechanical balance.

The unique cantilevers configuration of variable resistance beams produces a significant range of selectable performance resistance levels to match a body weight or specifically foot condition.

Additionally, the orthotic platform disclosed, herein, provides selectable flex that represents an integrated anti-pronation/supination mechanisms that responds to increasing medial loads by dynamic stiffening in proportioned response to body weight loading. The VRB resistance to compression or suspension is designed to be selectively increased or decreased prescriptively to maximize therapeutic benefit with comfort.

The cantilever system disclosed herein provides selectable incremental resistance to pronation/supination "on demand" to meet the needs of a wide range of patient foot imbalances, comfort requirements and podiatry conditions.

The adjustable or selective VRB orthotic technology enhances the user's bio-mechanical performance and therefore comfort by offering the Podiatrist a prescriptive incremental range of selectable resistances, per each customized zone of the foot to treat each patient's bio-mechanical, comfort and or specific sport performance requirements.

Figure 13A:
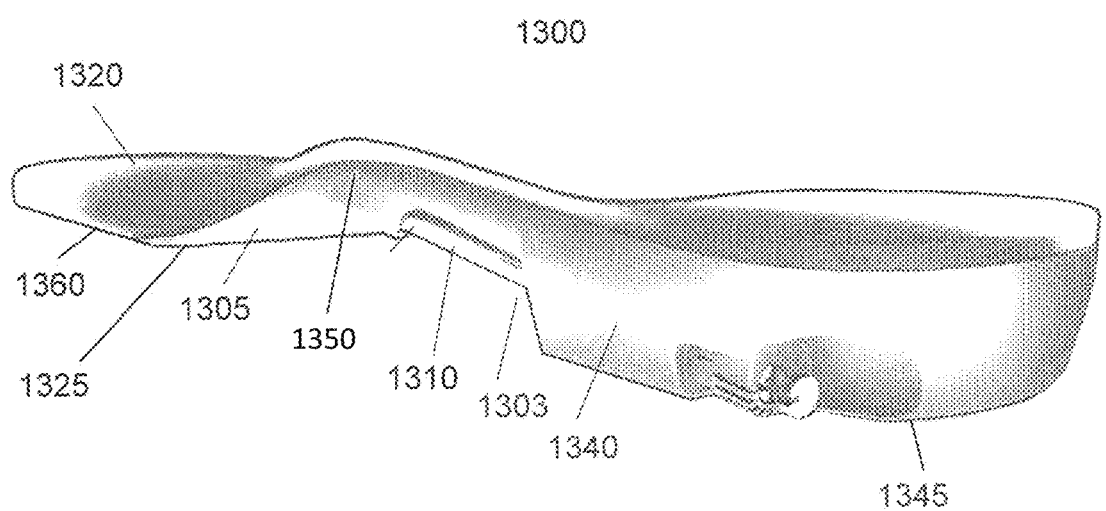
FIG. 13A-FIG. 13B illustrate perspective views of an exemplary configuration of an orthotic footwear incorporating a variable resistance (VRB) and suspension system in accordance with the principles of the invention.

FIG. 13A illustrates a perspective view of an exemplary embodiment of an orthotic 1300 including a VRB suspension support system 1303 in accordance with the principles of the invention.

As shown in FIG. 13A, the VRB orthotic variable resistance and suspension system 1303 includes a VRB 100 (hereinafter referred to as 1310), which is inserted through heel 1340 and extends to the mid-arch section 1350, positioned below an insole or force plate or platform 1305 of footwear 1300. As shown insole or force plate or platform 1305 includes an upper surface 1320 and a lower surface 1325.

Further illustrated is heel section 1340 having a flat surface 1345 and force plate 1305 having a front section 1360. Flat surface 1345 and front section 1360 rest on a same plane.

As will be discussed, the VRB 1310 comprises a generally elongated cylindrical beam or bar that includes a major axis greater than a minor axis. The orientation of the VRB 1310 with respect to the mid-arch section determines a degree of flexibility (or rigidity) that supports a foot load impacting or applied to the mid-arch section 1350. The VRB 1310 may be inserted and oriented at different degrees of orientation with regard to its major axis in order to adjust the degree of flexibility (or rigidity) of mid-arch section 1350. The degree of rotated orientation imparts a selectable resistance range per increment of rotation. For example, using an elliptical VRB, as is described with regard to FIG. 22D, in a 90° vertical or long axis position, the VRB 1310 is most rigid, while in the 0° horizontal (flat) position, VRB 1310 is most flexible. VRB 1310 operates as a cantilever to dynamically support and suspend the mid arch section 1350 with selectable resistance. In one aspect of the invention for selecting resistance, tensile strength of the material comprising VRB 1310 may be selected to affect flex performance, e.g., 1,000, 5,000, 10,000 or higher PSI Polymer tensile modulus.

As shown, VRB 1310 extends at an angle from heel section 1340 to mid-arch section 1350 to form a cantilever upon which mid-arch section 1350 rests. As a load is applied to the mid-arch section 1350, the mid-arch section 1350 engages and depresses VRB 1310. Based on the orientation of VRB 1310 with respect to mid-arch section 1350, VRB 1310 applies different levels of resistance to the force or load applied to mid-arch section 1350.

Each VRB selected resistance or suspension level provides and imparts a zone of tailored bio-mechanical support to dynamically correct imbalances, e.g. Pronation/Supination/Posting of the foot, by redistributing ground reaction forces, as well as realigning foot joints while standing, walking or running The biomechanics from each zone reacts by providing a smooth bell curve of support to dynamically and proportionally correct foot imbalance[s] to enhance foot performance per specific activity, e.g., weight dynamics, energy return from loading and unloading, cornering, sprinting, running, walking or to ease of locomotion.

Figure 13B:
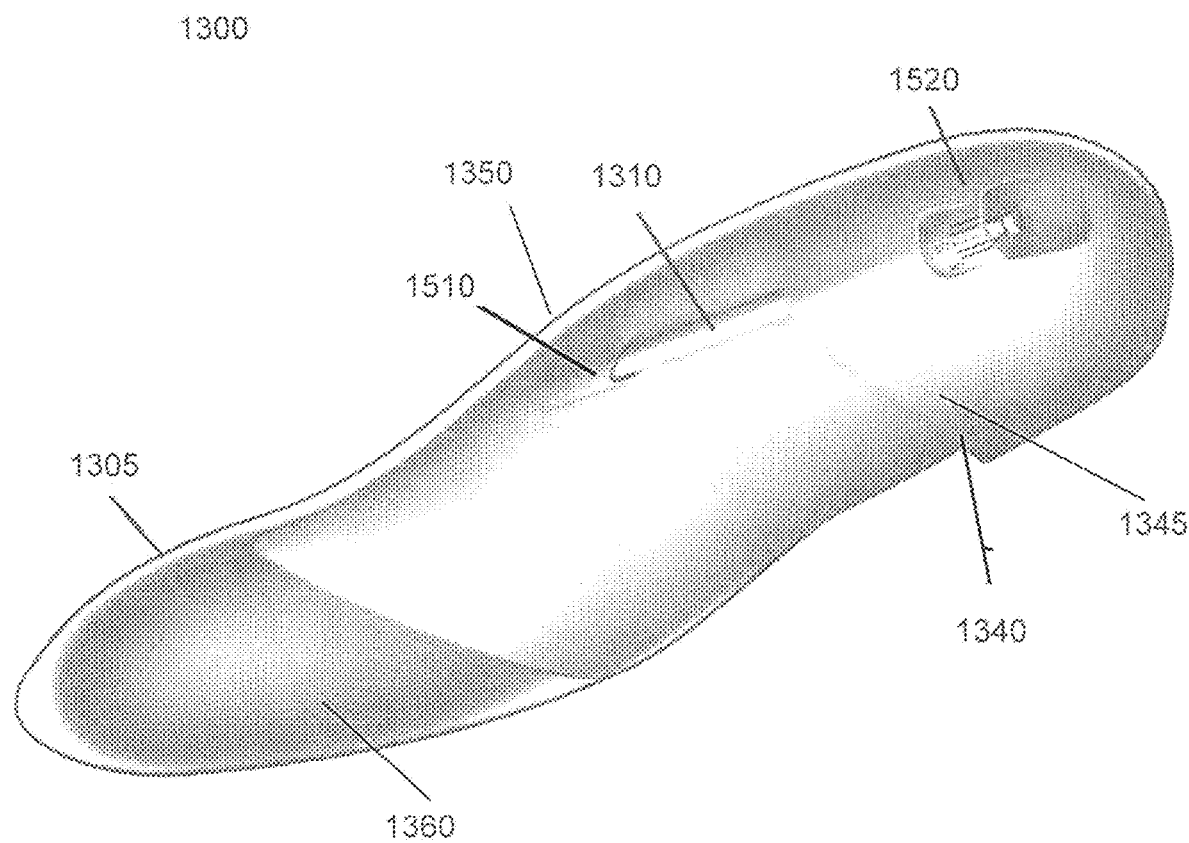

FIG. 13B illustrates a perspective, underview, of an orthotic 1300 including a VRB orthotic support system 1303 in accordance with the principles of the invention.

As illustrated, VRB 1310 extends from heel section 1340 to mid-arch section 1350, wherein VRB 1310 terminates in pocket 1510. Pocket 1510 captures a free end of VRB 1310, while allowing the VRB 1310 to rotate from a minimum resistive position to a maximum resistive position. As VRB 1310 rotates from a minimum resistive position to a maximum resistive position, the height of mid-section 1350 is changed, while simultaneously altering the degree of support or rigidity applied to the mid-section 1350.

Also illustrated is an exemplary selection or adjustment mechanism 1520 incorporated into heel section 1340. Adjustment mechanism 1520 enables a user to adjust VRB 1310 from a first (e.g. minimum resistive) position to a second (e.g., maximum resistive) position. In this exemplary embodiment, the adjustment mechanism 1520 represents a socket type adjustment, which will be described in further detail.

Although the VRB orthotic variable resistance and suspension system 1303 discussed herein is shown in FIG. 13A as being beneath the force plate or platform 1305 of footwear 1300, it would be appreciated that the VRB orthotic variable resistance system 1303 may be included within the footwear 1300 wherein force plate 1305 comprises one layer in contact with a user's foot (i.e., upper surface 1320) and a second lower layer (not shown) in contact with the external environment. This second lower layer connects front surface 1360 and heel section 1340 in a manner similar to that of a sneaker, for example.

Figure 14A:
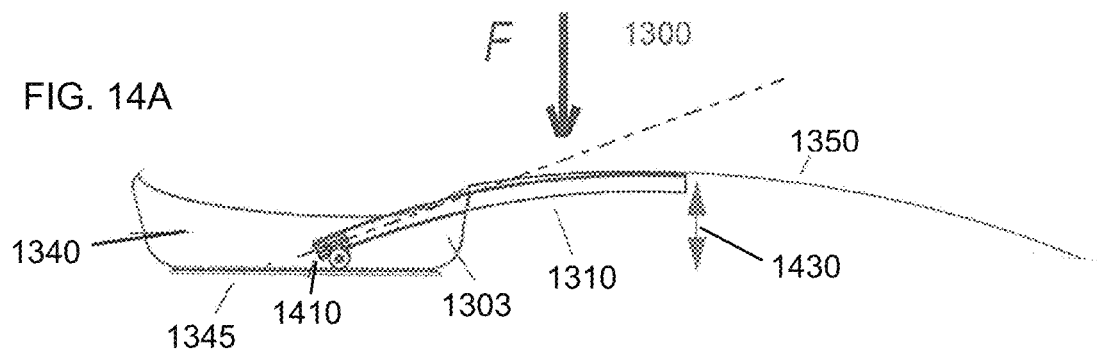
FIG. 14A-FIG. 14C illustrate side views of an exemplary first embodiment of an orthotic footwear incorporating a variable resistance (VRB) and suspension system in accordance with the principles of the invention.
Figure 14B:
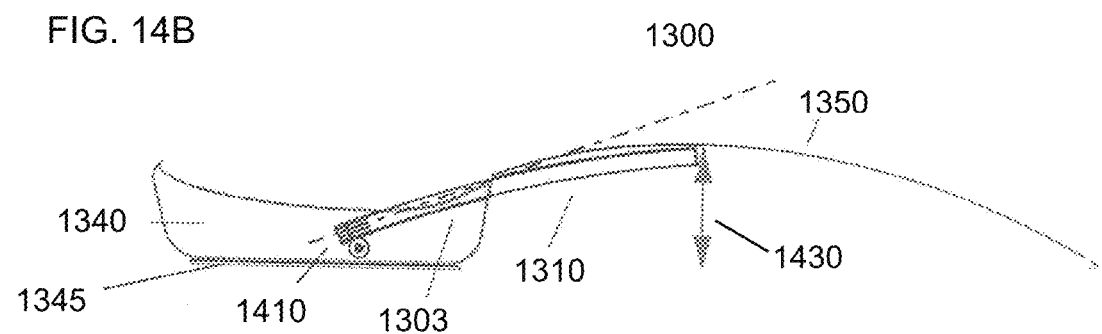
Figure 14C:
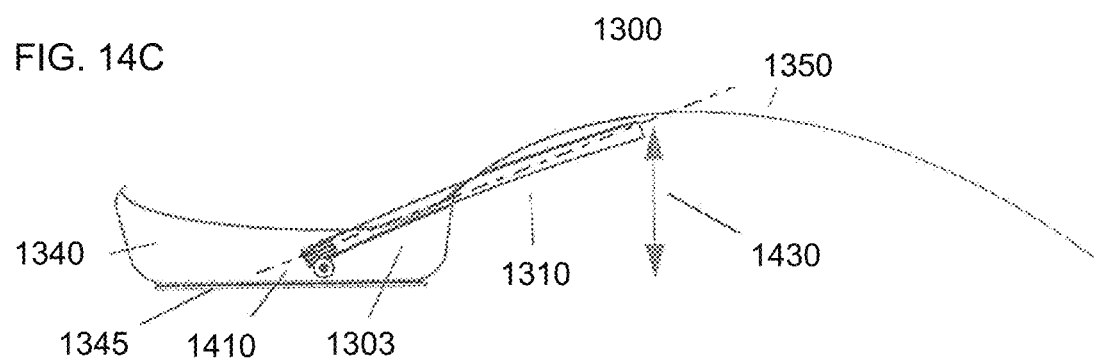

FIGS. 14A-14C illustrate different degrees of support for a mid-arch section 1350 based on an orientation of VRB 1310 with regard to a same level of force (F) applied to the mid-arch section 1350.

FIG. 14A illustrates a degree of support for mid-arch section 1350 when VRB 1310 is in a minimum resistive position. In this case, VRB 1310 provides a minimum resistance to force F applied to mid-arch section 1350, such that VRB 1310 may have a maximum deviation from an angle of inclination 1410 of VRB 1310 measured with respect to heel surface 1345.

FIG. 14B illustrates a degree of support for mid-arch section 1350 when VRB 1310 is in a position between a minimum resistive position and a maximum resistive position. In this case, VRB 1310 provides a mid-level resistance to force F applied to mid-arch section 1350, such that VRB 1310 may have a mid-range deviation from an angle of inclination 1410 of VRB 1310 measured with respect to heel surface 1345.

FIG. 14C illustrates a degree of support for mid-arch section 1350 when VRB 1310 is in a maximum resistive position. In this case, VRB 1310 provides a maximum resistance to force F applied to mid-arch section 1350, such that VRB 1310 has a minimum deviation from an angle of inclination 1410 of VRB 1310 measured with respect to heel surface 1345.

As shown in FIGS. 14A-14C, a height of mid-arch section 1350 may be altered based on the orientation of VRB 1310 with respect to the mid-arch section 1350 and heel section 1340.

In another aspect of the invention, a height 1430 of mid-arch section 1350 may be determined based the angle of inclination 1410 of VRB 1310 with respect to surface 1345. In a preferred embodiment, the angle of inclination 1410 of VRB 1310 with respect to a surface 1345 is in the range of 1 degree to 45 degrees. As would be recognized, the angle of inclination of VRB 1310 contributes to the height of mid-arch section 1350 and to the resistance of VRB 1310 to a force applied to mid-arch section 1350.

Figure 15:
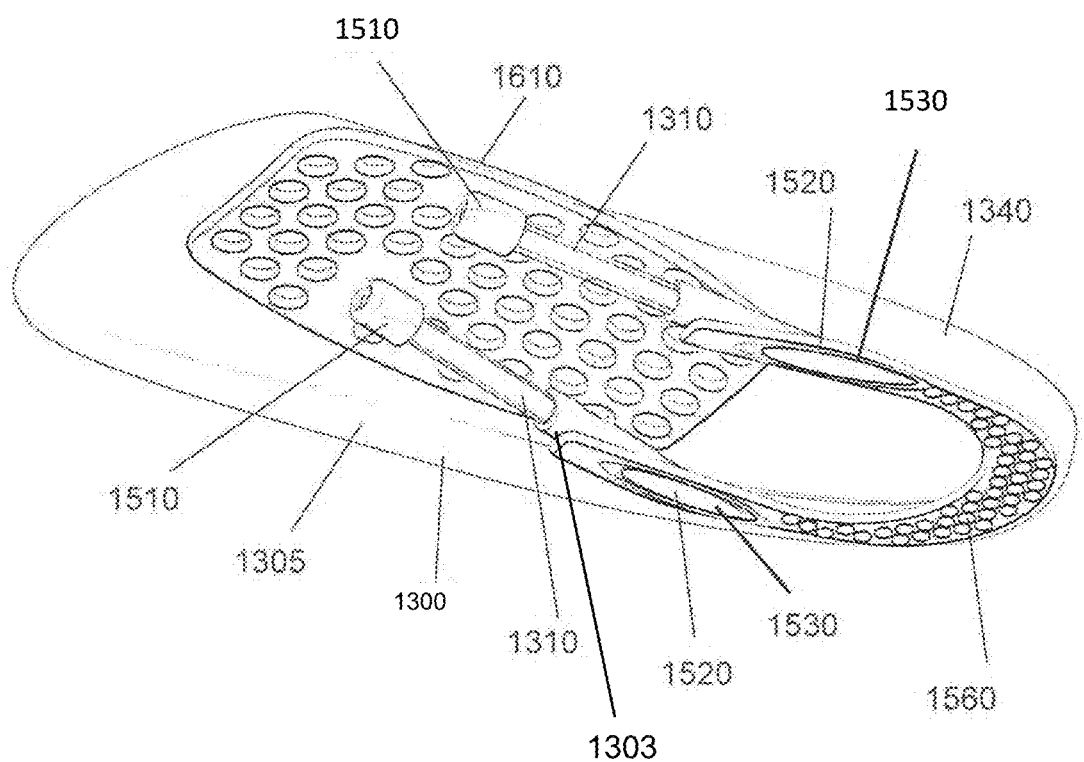
FIG. 15 illustrates a perspective view of an exemplary second embodiment of an orthotic footwear incorporating a variable resistance (VRB) and suspension system in accordance with the principles of the invention.

FIG. 15 illustrates a perspective view of an exemplary second embodiment of a VRB orthotic variable resistance and suspension system 1303 in accordance with the principles of the invention.

In this illustrated embodiment, two VRBs 1310 are shown supporting an optional attachment plate 1610 under force plate 1305. In this illustrated embodiment, two VRBs 1310 are positioned on a left side and a right side of attachment plate 1610. Application of multiple VRBs 1310 provides for symmetric or asymmetric support of a force applied to mid-section arch 1350. Although two VRBs 1310 are shown, it would be appreciated that additional VRBs 1310, extending toward the front of force plate 1305 may be incorporated without altering the scope of the invention. While attachment plate 1610 provides a base onto which pockets 1510 may be attached, it would be recognized that pockets 1510 may be directly attached to, or conformally configured into, force plate or platform 1305, in a manner shown in FIG. 13A, for example.

Also shown are corresponding entry points 1530 that allow access to adjustment mechanisms 1520, which provide individual control of a corresponding VRB 1310. In this illustrative example, adjustment mechanism 1520 alters the orientation of VRB 1310 with respect to mid-arch section 1350 through the rotation of a gear assembly, as will be discussed with regard to FIG. 17A-FIG. 17C, for example.

In the configuration shown, support provided by the VRB 1310 under the mid-arch section 1350 may be adjusted to be firmer on one side than support provided by the VRB 1310 on the other side to provide a customized level of support.

Also illustrated is heel plate 1560 that may be incorporated into VRB orthotic variable resistance and suspension system 1303. Heel plate 1560 provides additional support for heel section 1340 and an angle of inclination of VRB 1310.

Figure 16:
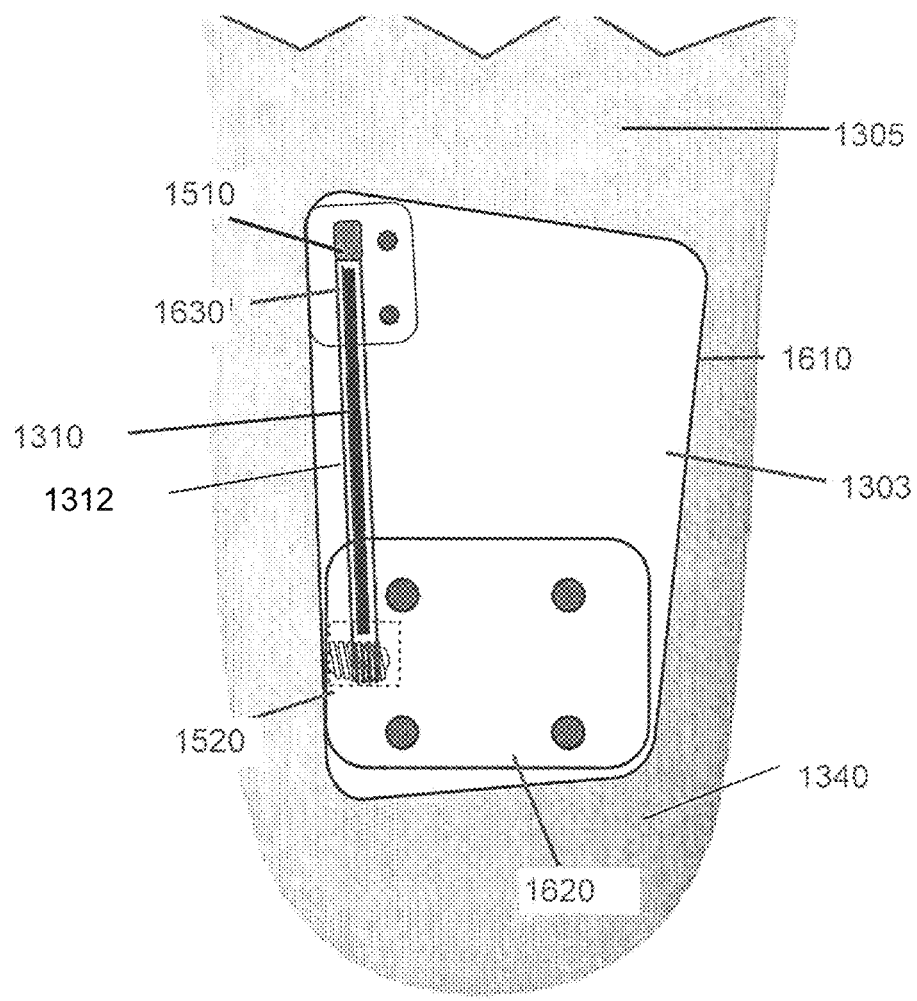
FIG. 16 illustrates a planar view of an exemplary second embodiment of an orthotic footwear incorporating a variable resistance (VRB) and suspension system in accordance with the principles of the invention.

FIG. 16 illustrates a planar view of an aspect of exemplary embodiment of a VRB orthotic configuration 1303 in accordance with the principles of the invention.

As illustrated, optional attachment plate 1610 extends from the heel portion 1340 to the mid-arch section 1350 of force plate or platform 1305. Attachment plate 1610, incorporated into sole-plate 1305 provides a surface over which a load or force applied to mid-arch section 1350 may be distributed. Attachment plate 1610 includes a heel plate section 1620 that is attached to sole plate 1305 in the heel section 1340. Also shown is a mid-arch section 1630 of plate 1610, which includes pocket 1510. Plate 1610 may be attached to sole plate 1305 using an adhesive, screws or rivets.

As would be recognized FIG. 16 illustrates a configuration applicable to a right side orthotic 1300 as VRB 1310 is positioned on a left side of orthotic 1300 so as to be positioned below the corresponding arch. As would be appreciated, the orientation of plate 1610 and VRB 1310 may be altered to be positioned on a right side of orthotic 1300, so as to be applicable to a left side orthotic. Incorporation of the VRB orthotic variable resistance and suspension system 1303 in a right side orthotic and a left side orthotic is contemplated and considered within the scope of the invention claimed.

Further illustrated is VRB 1310 extending from pocket 1510 to plate 1620, which incorporates another aspect of an adjustment mechanism 1520 in accordance with the principles of the invention. In this illustrative example, adjustment mechanism 1520 alters the orientation of VRB 1310 with respect to mid-arch section 1350 through the rotation of a gear assembly, as will be discussed with regard to FIG. 18A-FIG. 18F.

In one aspect of the invention, plate 1610 may be conformed to mid-arch section 1350 to provide a customized support for mid-arch section 1350. As would be appreciated, plate 1610 may be flat, conformed and/or customized without altering the scope of the invention.

As is further shown, VRB 1310 may be contained within a substantially circular housing, sleeve or sheathing 1312. Housing 1312 enables VRB 1310 to rotate substantially uniformly from a minimum resistance position to a maximum resistance (or support) position. In one aspect of the invention, the VRB 1310 may rotate within sheathing 1312, wherein sheathing 1312 is fixed. In another aspect of the invention, VRB 1310 may be attached to sheathing 1312 and as sheathing 1312 rotates, the contained VRB 1310 rotates.

As will be discussed with regard to FIG. 22A-FIG. 22F, VRB 1310 may possess an elongated shape having a major axis greater than a minor axis, which is substantially perpendicular to the major axis.

Figure 17A:
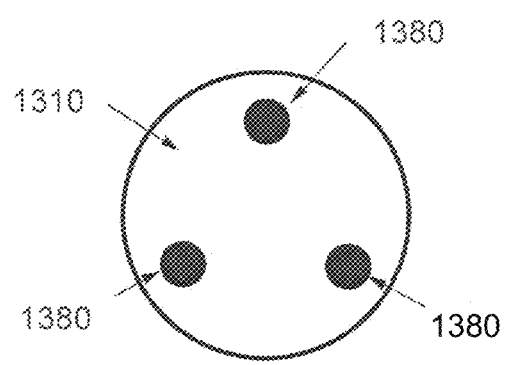
FIG. 17A-FIG. 17C illustrate aspects of a first exemplary embodiment of an adjustment mechanism for controlling rotation of a VRB configuration in accordance with the principles of the invention.
Figure 17B:
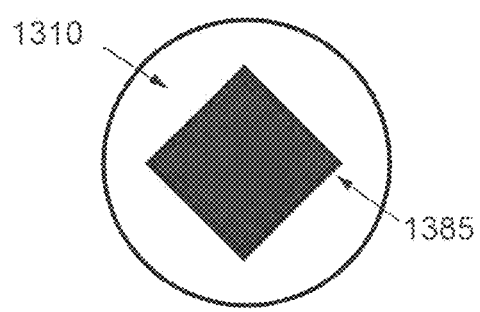
Figure 17C:
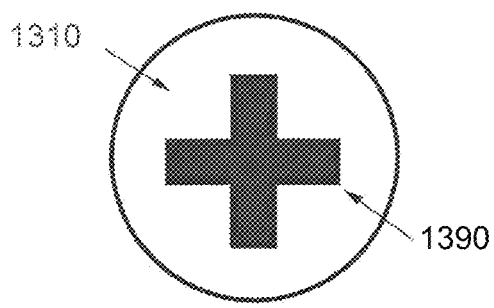

FIG. 17A-FIG. 17C illustrate end views of VRB 1310 including aspects of a first embodiment of an adjustment mechanism for altering the orientation of the VRB 1310.

FIG. 17A illustrates an example of an end of VRB 1310, which is accessible through heel section 1340, for example, that includes three circular cut-outs or indentations 1380 formed in a triangular pattern. Insertion of a tool (e.g., a screw driver) matching the indentation pattern 1380 allows for the rotation of VRB 1310.

Although indentations 1380 are shown in a triangular pattern, it would be recognized that the indentations 1380 may be arranged in any pattern that allows rotation of VRB 1310 to change the orientation of its major axis with respect to heel surface 1345.

FIG. 17B illustrates a second example of an end of VRB 1310 that includes a diamond shaped indentation 1385. In this case insertion of a tool (e.g., a screw driver) matching the diamond shaped indentation pattern 1385 allows for the rotation of VRB 1310 to change the orientation of its major axis with respect to heel surface 1345.

FIG. 17C illustrates a third example of an end of VRB 1310 that includes a Philips (or cross) pattern. In this case Insertion of a tool (e.g., a screw driver) matching the Philips (or cross) indentation pattern 1390 that allows for the rotation of VRB 1310 to change the orientation of its major axis with respect to heel surface 1345.

FIG. 18A-FIG. 18F illustrate exemplary aspects of a second exemplary embodiment of an adjustment mechanism in accordance with the principles of the invention.

Figure 18A:
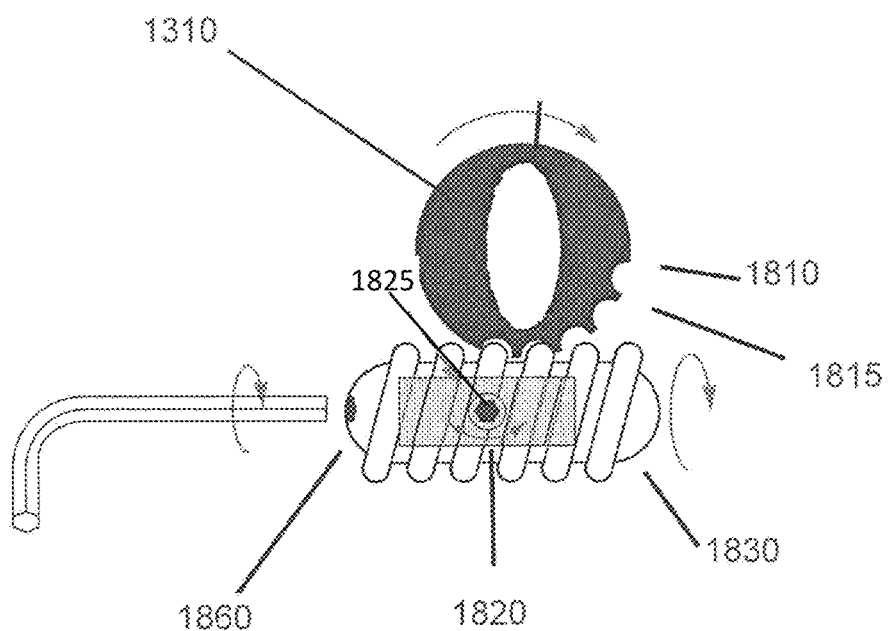

FIG. 18A illustrates an exemplary adjustment mechanism represented by a worm gear 1830, which engages a gear 1815 that is incorporated on a substantially circular gear head 1810 to which VRB 1310 is attached. Worm gear 1830 may include an adjustment means (such as an indentation 1860, which may capture an Allen key, Torx key, a Philips tip, for example, as shown in FIG. 17A-FIG. 17C). Insertion of the Allen key into indentation 1860 and rotation of Allen key causes rotation of worm gear 1830. As worm gear 1830 rotates, the rotation of worm gear 1830 is transferred to the gear 1815 of head 1810 causing the rotation of VRB 1310.

FIG. 18A further illustrates a locking plate 1820. Locking plate 1820 retains worm gear 1830 (and consequentially VRB 1310) in a locked position, as will be discussed.

As would be appreciated as VRB 1310 rotates from a minimum resistance position, corresponding to minor axis position, to a maximum resistance position, corresponding to major axis position, support to mid-arch 1350 increases from a minimum to a maximum.

Figure 18B:
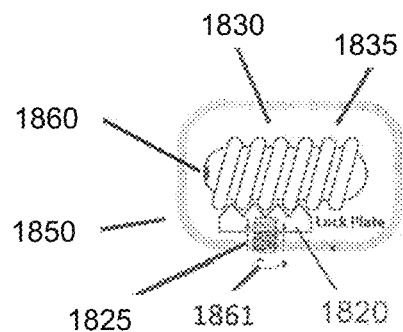

FIG. 18B illustrates a top view of worm gear assembly 1850 including worm gear 1830 and locking plate 1820. Further illustrated is screw (e.g. a set screw) 1825 that alters the position of locking plate 1820 with respect to worm gear 1830.

In one aspect of the invention, as shown in FIG. 18B, assembly 1850 includes a threaded opening 1861, through which passes set screw 1825 to engage locking plate 1820. As set screw 1825 is rotated in a first direction, locking plate 1820 is moved toward worm gear 1830. Locking plate 1820 further includes a toothed surface opposite screw threads 1835 of worm gear 1830. As locking plate 1820 advances towards worm gear 1830, the toothed surface of plate 1820 engages screw threads 1835 of worm gear 1830. In this position, worm gear 1830 is locked in position. Thus, the position of the VRB 1310 is fixed at that position to which VRB 1310 has been rotated by the rotation of worm gear 1830.

Figure 18C:
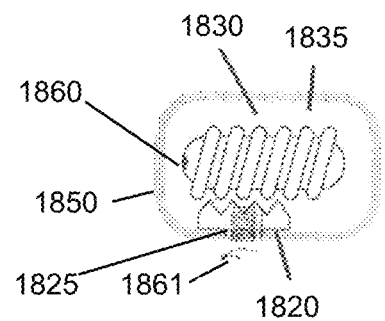

In another aspect of the invention shown in FIG. 18C, as screw 1825 is rotated in an opposite direction, the toothed surface of locking plate 1820 is withdrawn from screw threads 1835 and worm gear 1830 is free to rotate. In this manner, locking plate 1820 moves inward or outward along screw 1825 as screw 1825 is rotated. The position of locking plate 1820 may be altered by the insertion of an adjusting means, such as an Allen Key, a Philips screwdriver, etc., in screw hole 1861 to engage screw 1825.

Figure 18D:
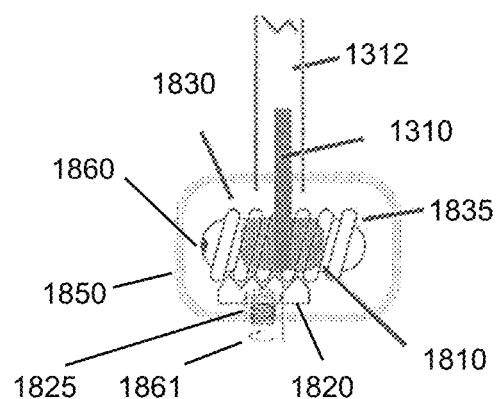

FIG. 18D illustrates a planar view of exemplary embodiment of the worm gear assembly 1850 in accordance with the principles of the invention. In this exemplary embodiment, locking plate 1820 engages screw threads 1835 of worm gear 1830.

Also illustrated is gear head 1810 engaging screw threads 1835. Gear head 1810 may be attached to VRB 1310, which enables VRB 1310 to rotate within sheathing or sleeve 1312. Alternatively, gear head 1810 may be attached to sheathing 1312 to allow rotation of VRB 1310.

FIG. 18E illustrates a planar view of orthotic 1300 including force plate 1305 incorporating the gear assembly 1850 shown in FIG. 18A-FIG. 18D. Assembly 1850 includes gear 1830, which engages gear head 1810 attached to VRB 1310. VRB 1310 is captured in pocket 1510, as previously described.

Further illustrated is a conventional Philips tip screw driver 1890 that may be used to rotate gear 1830 by insertion of the Philips tip into indentation 1860, which is shaped in a manner similar to that shown in FIG. 17C.

Although a conventional Philips tip screw driver 1890 is illustrated, it would be appreciated that indentation 1860 may comprise a proprietary shape requiring a corresponding proprietary tip similar to those shown with regard to FIG. 17A-FIG. 17B.

FIG. 18F illustrates a side view of orthotic 1300 including force plate 1305 wherein indentation 1860 is shown having a cross shape that engages the tip of Philips screw driver 1890.

As previously discussed, as gear 1830 is rotated, VRB 1310 is rotated through the engagement of gear head 1810 with gear 1830.

FIG. 19A-FIG. 19D illustrate aspects of a third exemplary adjustment mechanism for controlling rotation of a VRB utilized in the orthotic 1300 shown in FIG. 13A and FIG. 13B, for example.

Figure 19A:
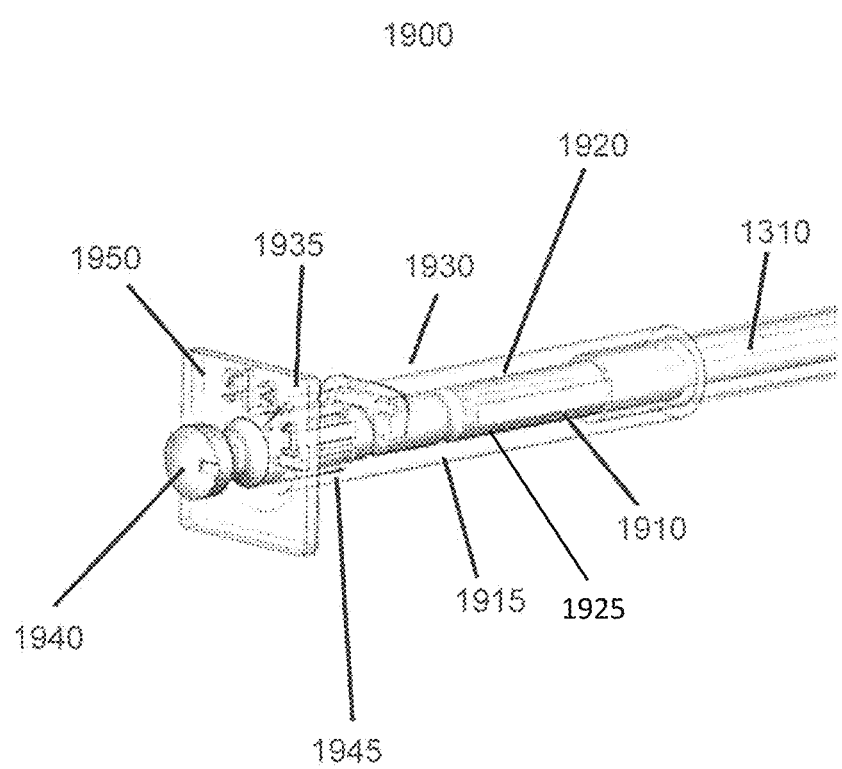
FIG. 19A-FIG. 19D illustrate a third exemplary embodiment of an adjustment mechanism for controlling rotation of a VRB configuration in accordance with the principles of the invention.

FIG. 19A illustrates a perspective view 1900 of a third exemplary configuration of a control or adjustment means in accordance with the principles of the invention.

In this exemplary configuration, referred to herein after as "spline/socket", a manual, geared, mechanism selectively rotates VRB 1310 in controlled increments ranging from 0° to 90° while simultaneously controlling torque.

As shown, the socket/spline 1900 provides an adjustable locking system that secures a VRB 1310 from rotation and therefore mechanically maintains a constant resistance or suspension.

VRB 1310 further includes a fork or tongue 1910 that is insertable into spline 1920. Spline 1920 is a substantially round, solid, rod including tongue or fork 1925. Tongue or fork 1925 engages (and matches) tongue or fork 1910 of VRB 1310.

Also shown is socket 1930 into which spline 1920 is inserted. Socket 1930 contains fork 1925 and tongue 1910 in a manner such that as spline 1920 is rotated, VRB 1310 is similarly rotated.

At a proximal end of socket 1930 is shown grooves 1935 and spline elements 1945 formed between adjacent ones of grooves 1935. In one aspect of the invention, the spacing of spline elements 1945 (grooves 1935), provides for a desired locking rotation. For example, 16 spline elements 1945 provide for 22.5° of incremental VRB 1310 rotation. (360°/16=22.5°).

In accordance with the principles of the invention, VRB 1310 plus spline 1920 form an adjustable assembly, wherein the spline element 1920 may be pulled out by grasping spline head 1940, rotating the spline element 1920 and re-inserting the spline 1920 into socket 1930, to provide a higher or lower resistance or suspension level. This level of resistance is dependent upon the rotation VRB 1310.

Also illustrated is faceplate 750. Faceplate 1950 includes an indicia of the degree of rotation of VRB 1310.

As would be appreciated, tongues or forks 1925 and 1910 are sized so that they remain engaged, even when spline 1920 is pulled out, turned and re-inserted into socket 1930.

Figure 19B:
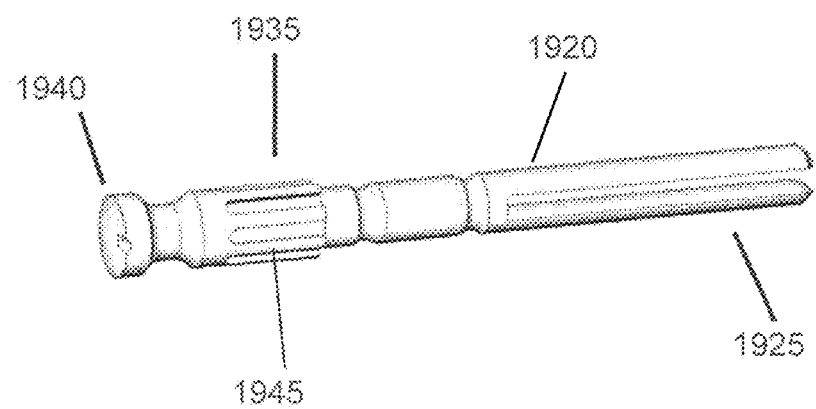

FIG. 19B illustrates a perspective view of spline 1920. In this illustrative embodiment, spline 1920 is a substantially cylindrical rod including at a first end fork 1925 and a spline head 1940 on a second end. Further illustrated are spline elements 1945 positioned about a circumference of spline 1920 between adjacent ones of grooves 1935.

As shown, a length of fork 1925 is sufficiently greater than a length of spline elements 1945 in order to prevent spline 1920 from disengaging VRB 1310 (not shown) when spline 1920 is pulled from socket 1930

Figure 19C:
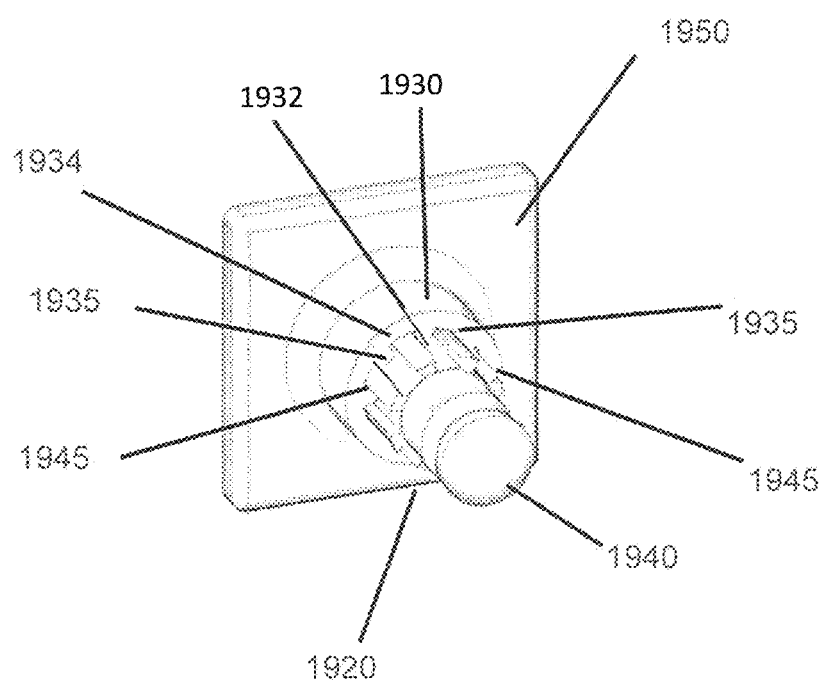

FIG. 19C illustrates a perspective view of a spline element 1945 of spline 1920 engaging grooves 1932 of socket 1930. In this illustrative example, socket 1930 includes a plurality of grooves 1932 and spline elements 1934 between adjacent ones of grooves 1932. Grooves 1932 and spline elements 1934 of socket 1930 match in number and width with spline element 1945 and grooves 1935.

As discussed, spline 1920 may be withdrawn from socket 1930, rotated and reinserted into socket 1930. The rotated and reinserted spline 1920 alters the position of the VRB 1310 (not shown) such that a different level of rigidity of VRB 1310 may be achieved (see FIG. 13A-FIG. 13C). The engagement of spline elements 1945 with grooves 1932 lock and retain VRB 1310 (not shown) in a desired position.

Figure 19D:
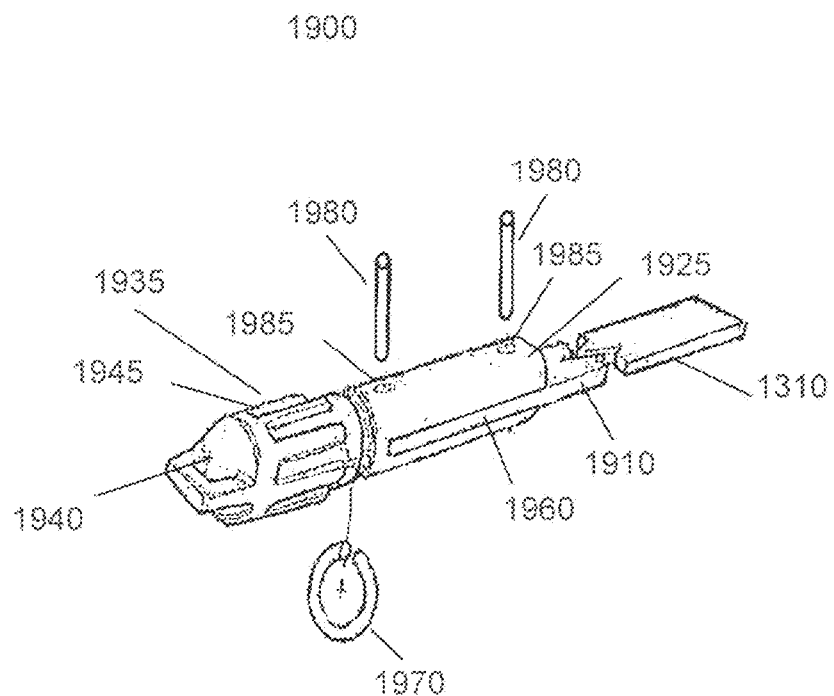

FIG. 19D illustrates a perspective view of a control mechanism 1900 illustrating VRB 1310 engaging fork 1925 in spline 1920 in accordance with the principles of the invention.

In this illustrative embodiment, VRB 1310, which is shown having a rectangular cross-section, includes tongue 1910 that may be inserting into fork 1925 in order to provide a secure connection between tongue 1910 and fork 1925, as previously discussed.

Further illustrated is retaining ring 1970. Retaining ring 1970 represents a spring loaded mechanism that enables spline head 1940 to be withdrawn from socket 1930 by pushing spline head 1940 into socket 1930. The act of pushing spline head 1940 into socket 1930 disengages retaining ring 1970 and the spring loaded mechanism forces spline head 1940 to withdraw from socket 1930. In one aspect of the invention, retaining ring 1970 may be constructed of a spring-able material and shaped to operate as the spring mechanism.

Further illustrated are pins 1980, which when inserted into holes 1985 provide a secure connection between fork 1925 and tongue 1910.

As would be appreciated holes 1985 may be elongated in order to allow spline head 1940 to be withdrawn from socket 1930 a limited distance. In this case, spline head 1920 may not be totally withdrawn from socket 1930 (not shown) even if spline head 1940 is inadvertently pushed in.

Figure 20A:
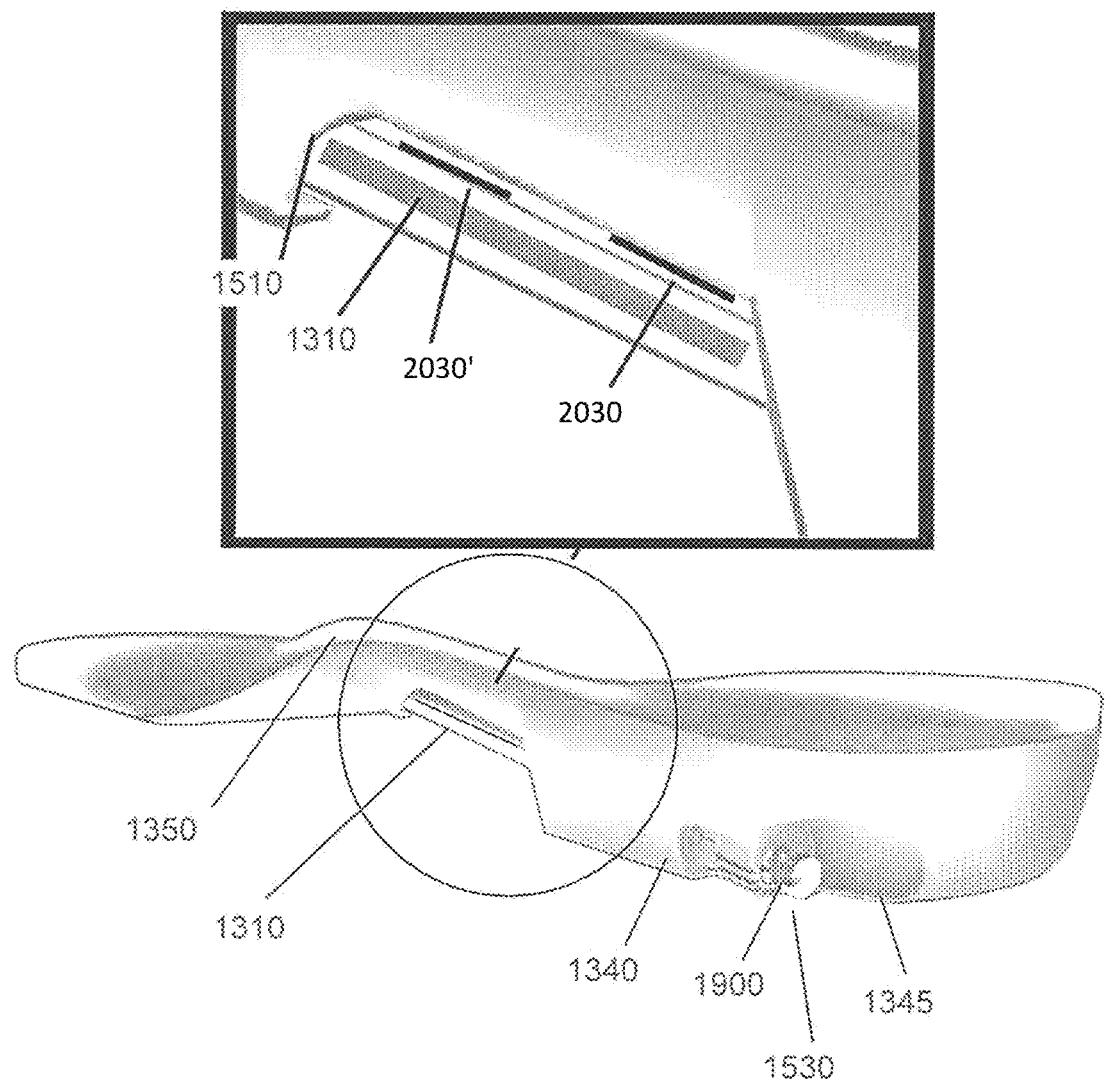
FIG. 20A illustrates a perspective view of an exemplary embodiment of a footwear incorporating VRB and sensing technology in accordance with the principles of the invention.

FIG. 20A illustrates a perspective view of an exemplary variable resistance and suspension system 1303, similar to that shown in FIG. 13A. In this illustrative embodiment, the VRB configuration includes an adjustment mechanism similar to that shown in FIG. 19A, wherein the VRB 1310 may be rotated in discrete intervals. It would, however, be appreciated, that the adjustment mechanism shown in FIG. 17A-FIG. 17C or FIG. 18A-FIG. 18F may similarly be utilized without altering the scope of the invention.

As shown in the enlarged section of FIG. 20A, bio-sensor 2030 may be incorporated onto the force plate 1305 of orthotic 1300. Incorporation of bio-sensor 2030 provides for a prognostic and injury avoidance capability to measure a mechanical deflection of dynamic loads being exerted on a body joint or structure. This is principally achieved through the monitoring of the flexing shape of a VRB (Variable Resistance Beam) or multiple VRBs as loads are dynamically applied, quantified and recorded with the wearer notified of loading conditions that would exceed the joints physical ability sustain normal operation without damage, e.g. repetitive strain. Thus, measurement of dynamic joint loading over time provides a real time health monitoring and predictive system to prevent or treat injury.

A few examples of physical sensors 2030 to measure and quantify joint stress, strain loading cycles, and/or changing suspension support requirements are Thin Films, Wheatstone Bridges (metal foil sensor structures), potentiometers, temperature gauges, pressure gauges, foils, piezo-resistors, semiconductors, nano-particulates, conductive nanolayers, silver nanowire, Graphene, e.g. graphene imbued rubber bands: flexible, low-cost body sensors, such as nanoelectromechanical devices, piezoresistive devices, conductive electroplating, diffraction grating, optical fiber, optical grid (Non-Intrusive Stress Measurement System—NSMS), wire, micro tubes, miniature Wi-Fi transmitters, accelerometers, load cells and or other means to detect VRB flexure or movement of any kind.

Physical sensing of the application of a force or strain occurs when one or more VRBs 1310 is deflected or flexed. As the physical shape of the VRB is deformed, an electrical resistance changes. Similarly, other measurement quality (ies) or physical parameter(s), e.g. optical, physical location or acceleration, are similar effected.

For example, the Wheatstone bridge illustrates the concept of a difference measurement, which can be extremely accurate. Variations on the Wheatstone bridge can be used to measure capacitance, inductance, impedance and other quantities to calculate total potential movement over time.

Figure 20B:
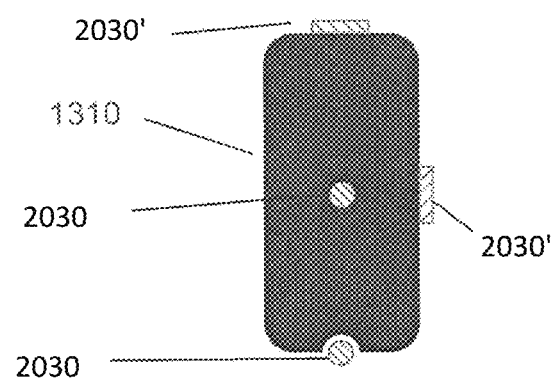
FIG. 20B illustrates exemplary placements of sensing technology in accordance with the principles of the invention.

Although FIG. 20A illustrates the placement of bio-sensor 2030 on force plate 1305, placement and locations of the bio-mechanic sensors 2030 may be bonded onto or along the surface length of VRB 1310 into a side channel and/or internally through an interior diameter hole, bore and or extruded geometry to accept and hold the sensor. (see for example, element 2030'). FIG. 20B illustrates exemplary placement of sensors 2030 on or within VRB 1310.

In another aspect a strain gauge may be incorporated in which advantage is taken of the physical property of electrical conductance and its dependence on the conductor's geometry. For example, when an electrical conductor is stretched within the limits of its elasticity without permanent deformation, the sensor will become narrower and longer. This changes or increases the electrical resistance along the sensors length or end to end. Silver nanowire is an excellent example of an electrical conductor with a 150% stretch limit while measuring conductivity with fidelity.

When measuring electrical resistance of a strain gauge bonded to a VRB 1310, the amount of applied stress may be inferred. As an example, another typical strain gauge arranges a long, thin conductive strip in a zig-zag pattern of parallel lines such that a small amount of stress in the direction of the orientation of the parallel lines results in a multiplicatively larger strain measurement over the effective length of the conductor surfaces in the array of conductive lines—and hence a multiplicatively larger change in resistance—than would be observed with a single straight-line conductive wire.

Other methods of sensing VRB deflection range from temperature (kinetic heating), piezo (milli-voltage generation), electromagnetic sensing, optical sensing (diffraction grating), to miniature Wi-Fi signaling physical location and or accelerometer chips.

As would be recognized one or more of the described sensors, herein, may be incorporated into the illustrative sensor 2030 (or 2030'). All sensors may directly wired and connected to a physical circuit. Or by means of a wireless signal to an embedded printed circuit board (PCB) with processing algorithm, battery and transmitter information regarding the flex and/or stress detected may be processed (using one or more algorithms) on the PCB and the results forwarded to a remote receiver (i.e., handheld or worn) to alert the wearer to potential injury or current physical condition. Similarly, the measured parameters (i.e., raw data) may be provided to a remote receiver for subsequent processing.

In another aspect of the invention, with the addition of accelerometer microchips, e.g. similar to ones used in smartphones/tablets/watches or such devices, 360° X Y Z axial data is produced and therefore a more informative and prescriptive biomechanical measurements may be captured to warn of impending injury and inform the wearer whether the feet are increasingly pronating or supinating mechanics.

An accelerometer chip interfaced with one or more biosensors 2030 may provide further prescriptively diagnose of the body joint condition, i.e. foot, by using quadrant data of the foot to compare and contrast body weight loading (history) and changing weighting dynamics per zone. Specifically, this quadrant data of weight loading combined with an accelerometer chip detecting movement in 360° X Y Z axes may determine whether an injury or foot condition is worsening, progressing to injury, failure, as well as monitor and quantify podiatry foot conditions, e.g. heel posting.

This data would be central to the diagnosis, treatment and physical therapy. Measurement of the parameters associated with the application a force to the variable resistance and suspension system 1303 shown in FIG. 13A, for example, may be customized and tailored to each individual's support requirement and notably reduce atrophy by allowing the wearer degrees of movement.

Figure 21:
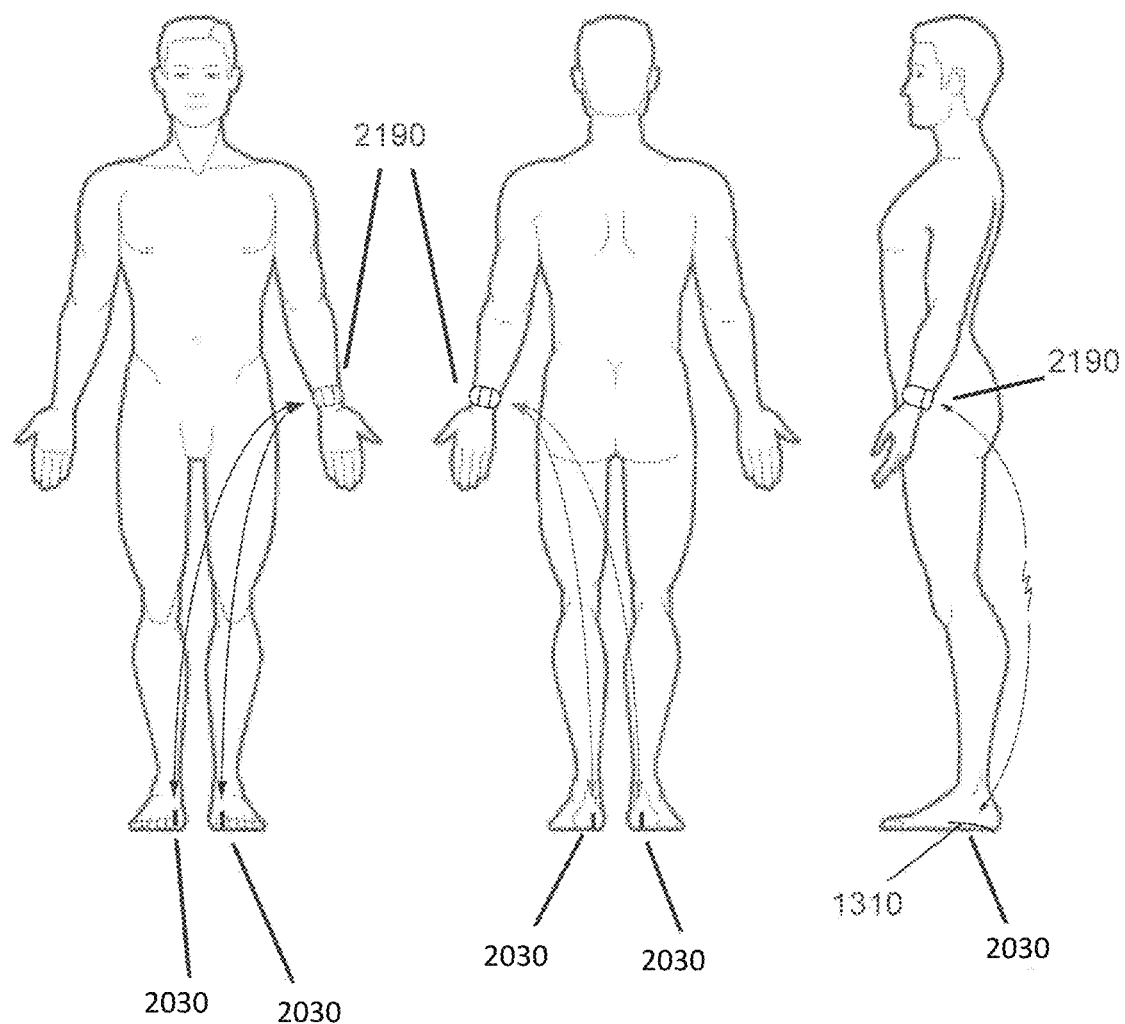
FIG. 21 illustrates an application of the aspect of the configuration shown in FIG. 20A.

FIG. 21 illustrates an exemplary configuration of a handheld device 2190 communicating with one or more sensors 2030 (2030') incorporated into the variable resistance and suspension system 1303 shown in FIG. 13A, for example.

As would be appreciated communication between sensors 1530 (1530') may be through a short range communication protocol, such as BLUETOOTH, NFC, etc.

In one aspect of the invention, the VRB 1310 mechanical movement may be captured by piezo, dynamo (polyphase AC/DC electric motor), hydraulic or other mechanism to capture and store mechanical energy from the VRB flexing or orthotic shell cyclical compression during walking. This system may be used as a battery recharging system using a device capable of capturing mechanical movement and converting the mechanical movement into electrical energy. For example, piezo-material or PvF2 (PolyVinylidene Fluoride 2) may be incorporated into the VRB assembly to create a battery recharging system and/or a heel cushion to absorb bodyweight impacts via shock absorbing diaphragm. Additionally, part of the energy generated would be used to transmit the bio-sensor data to a wearable device (2190, FIG. 21) to inform the wearer in real time of the condition of their body joint condition, i.e. left or right foot.

In another aspect of the invention, the recharging system may also be connected to and provide energy to drive a worm gear servo to change the VRB resistance setting to prescriptively support the body joint condition in response to the bio-sensor data. This closed looped system provides a prescriptively corrective, rehabilitative, prophylactic or preventative support system for a body joint or extremity, e.g. foot, by increasing and/or decreasing the support imparted. The closed data loop system consists of a flexing VRB 1310 to biomechanically support a body structure or joint bonded to a Biosensor whose data stream is connected to an 'onboard PCB' (printed circuit board). The biosensor data signal is received, transmitted and stored onto the PCB to produce an algorithm output. The closed data loop system is sustained by a mechanism to continually charge a battery and/or supply electricity to charge the system. An advanced version of this charging system could be employed to automatically instruct a worm gear servo to change the VRB support levels (lower or higher) per biosensor diagnostic algorithm data stream.

In another aspect of the invention additional means of creating self-adjusting orthotic shell geometry may incorporate the use of programmable smart materials, such as carbon fiber, nitinol wire mesh, smart, self-morphing filaments, e.g. wood, or composite materials designed to become highly dynamic in form and function, specifically when an electric charge is applied or other shaping factors.

FIG. 22A-FIG. 22F illustrate cross-sectional views of exemplary embodiments of a VRB in accordance with the principles of the invention. The VRBs, presented as resilient rods, beams or shafts, may be composed of solid, semi-solid or hollow construction in accordance with embodiment the principles of the invention. The VRB technology comprises a major and minor axis, which produces variable resistances when orientated in a direction of x, y, z plane or combination of planes in 360 degrees of rotation, bending movement.

Figures 22A, 22B, 22C, 22D, 22E, 22F:
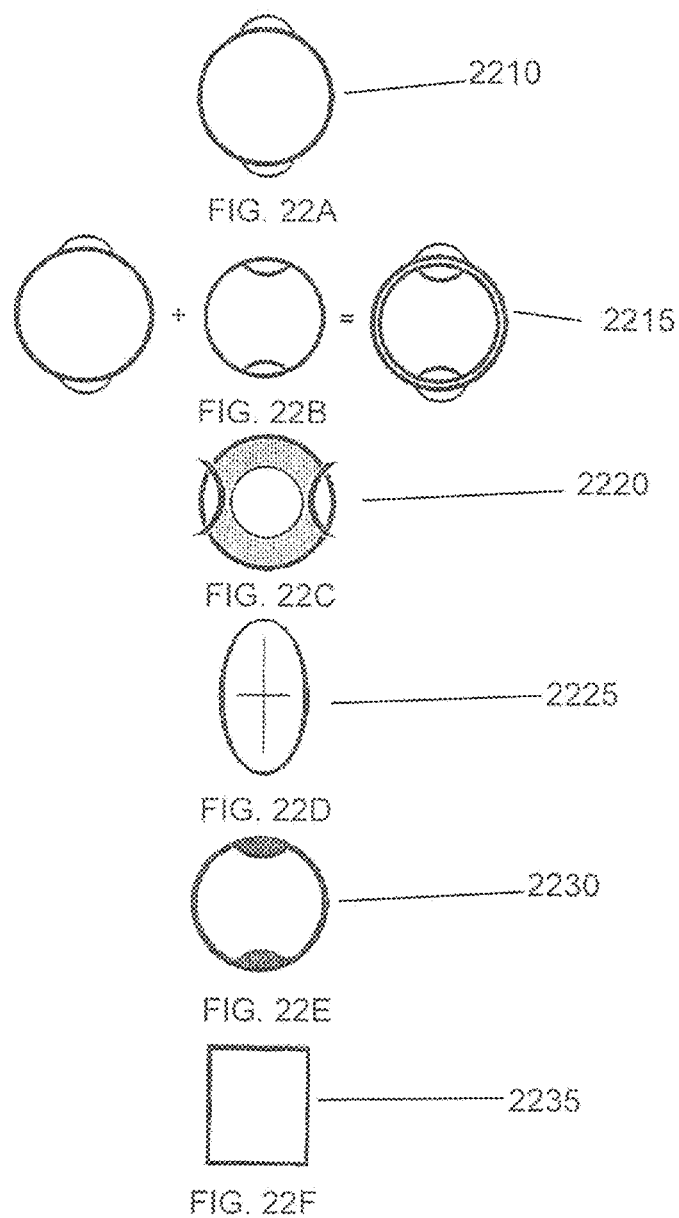

FIG. 22A represents a Type II I-Beam configuration 2210 that includes one of: a static outside and internal diameter geometry or combination, thereof. The Type II I-Beam cross section geometry produces proportional adjustable resistance according to a rotated orientation creating a relationship between an orientation and a resistance.

FIG. 22B represents a Type III Dual I-Beam configuration 2215 that includes inner and outer I-Beam tubes with inner and/or outer geometry or combination thereof to create variable I-beam resistance.

FIG. 22C represents a Type IV Conical beam configuration 2220 that includes hollow, additive or subtractive wall geometry. Conical Beam cross section geometry produces proportional adjustable resistance according to a rotated orientation.

FIG. 22D represents a Type V Ellipsoidal beam configuration 2225 that may be a solid, a semi-solid or a hollow beam with or without outside and/or internal diameter geometry or a combination, thereof along its major axis, thus, generating additional I-beam mechanics and/or subtractive, e.g., conical hollow, geometry along its minor axis. Ellipsoidal beam with a major axis that is wider than the minor axis with or without internal or external geometry along the major axis.

FIG. 22E represents a Type VI Internal 'I-beam' configuration 2230 that includes one or more spines within a hollow cylindrical or conical shaft.

FIG. 22F represents a Type VII Rectangular beam configuration 2235 that includes two sides wider than the remaining two sides.

FIGS. 23A-23E illustrate end views of VRB 1310 including additional aspects of indentations for altering the orientation of the VRB 1310, in accordance with the principles of the invention.

Figure 23A:
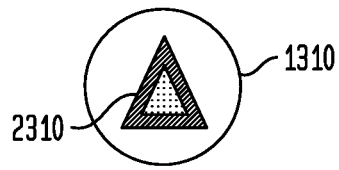
Figure 23B:
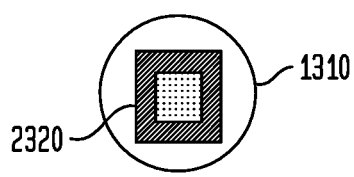
Figure 23C:
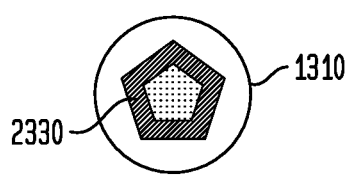
Figure 23D:
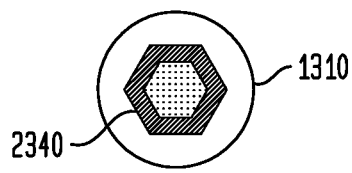
Figure 23E:
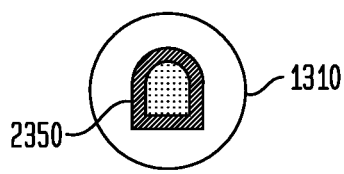

FIG. 23A illustrates an indentation 2310 shaped in a triangular form. FIG. 23B illustrates an indentation 2320 shaped as a square, similar to that shown in FIG. 17B. FIG. 23C illustrates an indentation 2330 shaped as a pentagon and FIG. 23D illustrates an indentation 2340 shaped as a hexagon. As would be recognized any multi-surfaced polygon may be utilized as an indentation without altering the scope of the invention. FIG. 23E illustrates an indentation 2350 shaped as an extended semi-circular form (a "D" shape). Although not shown, it would be recognized that the extended semi-circular form shown in FIG. 23E may be limited such that the indentation may be a semi-circle.

As would be understood in the art, a special shape tool is needed to engage the indentations in FIGS. 17A-17C and FIGS. 23A-23E, in order to change the orientation of the VRB 1310 to achieve a desired degree of stiffness or flexibility. Utilization of special purpose tools to engage the specific forms of, exemplary indentations, as shown herein, is advantageous as the unique head of the special purpose tools provides maximum contact to the indentation to alter or change the orientation of the corresponding VRB 1310.

Figure 24:
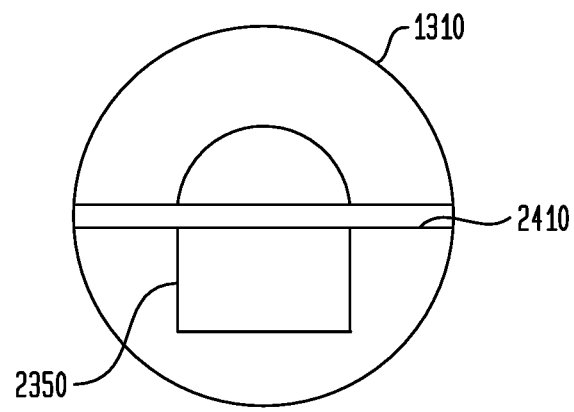
FIG. 24 illustrates another aspect of the indentations shown in FIG. 23E.

FIG. 24 illustrates another aspect of an indentation 2410 incorporated into an end of VRB 1310, wherein a slot 2410 passes substantially through the illustrated indentation. Slot 2410 provides a second means for changing the orientation of the VRB 1310 with the insertion of a commercially available flat-head screw driver in cases where the corresponding tool is not available.

Figure 25A:
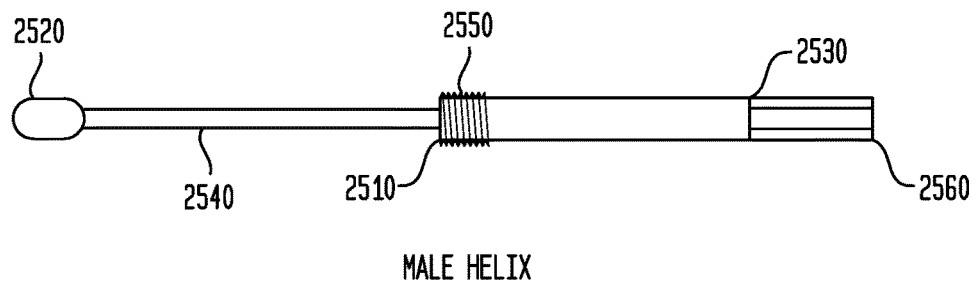
FIGS. 25A, 25B, 25C illustrate component parts of a VRB structure in accordance with principles of the invention.

FIG. 25A illustrates a side-view of another embodiment of a VRB 2510 in accordance with the principles of the invention. VRB 2510 comprises a variable resistance beam section (VRBS) 2540, which is comparable to VRB 1310 previously described with regard to FIGS. 1A-1G. VRBS 2540 operates in a manner similar to that described with regard to VRB 1310 in that the orientation of VRBS 2540 determines a stiffness of the VRB 2510 to a downward force, as previously discussed.

Further illustrated is position head 2520 attached on a first end of VRBS 2540. Position head 2520 may be of a substantially cylindrical shape with, as illustrated rounded ends. Position head 2520 smoothly rotates within a pocket in an orthotic platform as VRBS 2540 rotates. Alternatively, position head 2520 may be fixed to an orthotic platform and VRBS 2540 rotates within position head 2520. VRBS 2540 further includes a substantially cylindrical shank section 2530 attached to a second end of VRBS 2540. Shank section 2530, which is substantially circular, provides for control of the rotation of VRB 2510 and the orientation of the non-circular section VRBS 2540. Shank section 2530 includes a screw thread (or helix) 2550, which in a preferred embodiment is a male thread, positioned adjacent to the second end of VRBS 2540. Shank section 2530 further includes on a second end 2560, an adjustment means, such as the indentation shown in FIGS. 17A-17C and FIGS. 23A-23E. To further describe the VRB 2510, the embodiment of the indentation shown in FIG. 23E, (i.e., the "D-shape') is discussed. However, it would be understood that the discussion of the invention described, is not limited to the D-shape indentation but is applicable other indentation shapes without altering the scope of the invention.

Figure 25B:
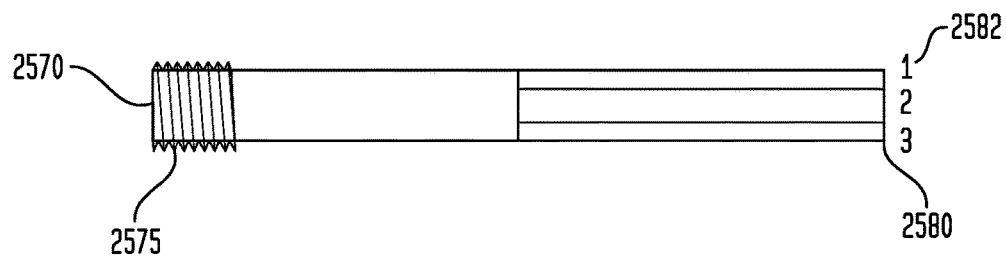

FIG. 25B illustrates a hollow cylindrical bushing shank 2570, comprising a screw thread or helix on a first end 2575 and an indicia 2582 on a second end 2580. The indicia 2582 provides a reference of the orientation of VRBS 2540.

Figure 25C:
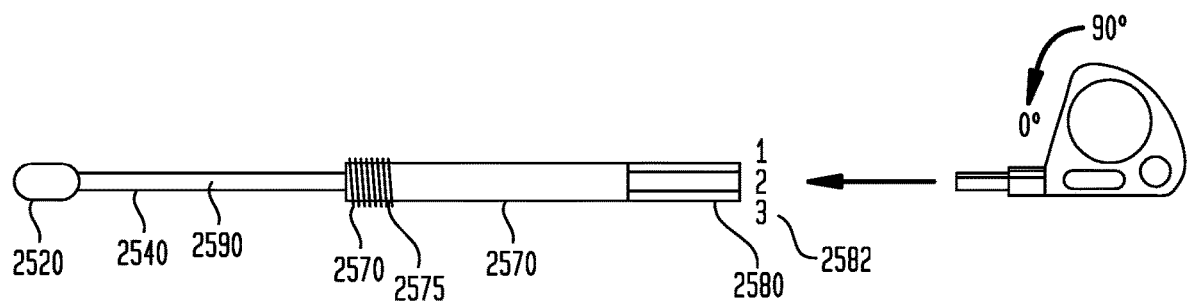

FIG. 25C illustrates a completed VRB assembly 2590 wherein the VRB 2510 is inserted into bushing shank 2570. The screw thread or helix 2550 on VRB 2510 engages the screw thread 2575 on bushing shank 2570 to retain VRB 2510 in shank 2570.

Figure 26:
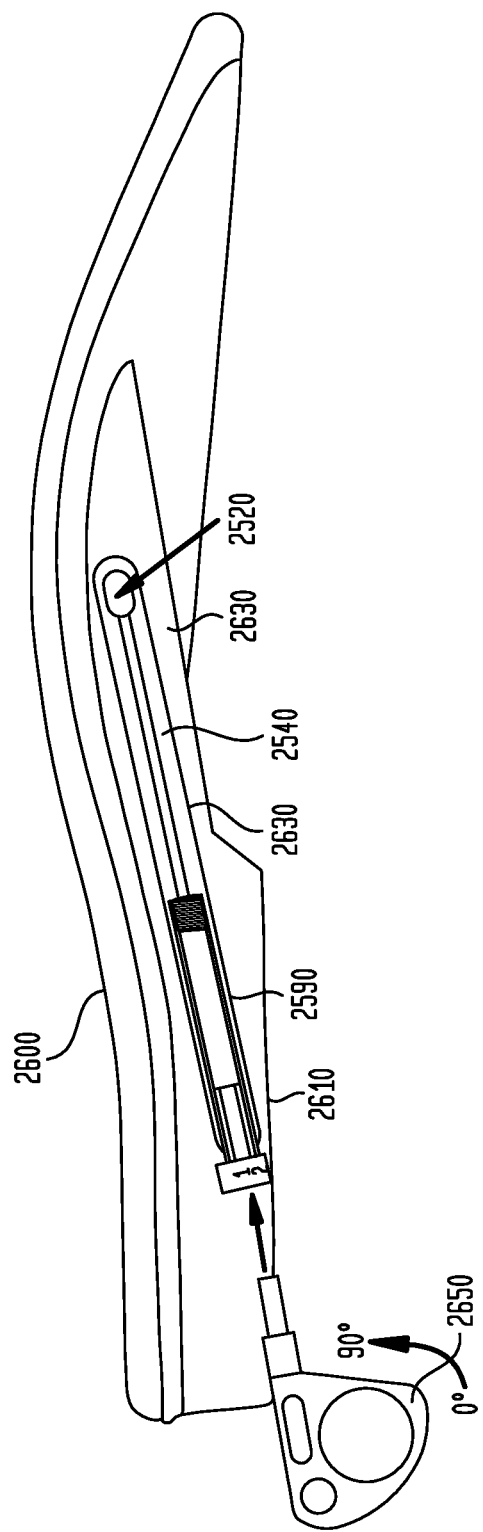
FIG. 26 illustrates a side view of an exemplary orthotic platform in accordance with the principles of the invention.

FIG. 26 illustrates a side view of an orthotic platform 2600 in accordance with the principles of the invention. In the illustrated embodiment, VRB assembly 2590 is inserted through a heel section 2610 and extends towards a mid-arch section 2620 at an angle, as previous discussed.

Further illustrated is sleeve 2630 in platform 2600 into which VRB assembly 2590 is inserted, wherein the position head 2520 is positioned under mid-arch section 2620. Further illustrated is an adjusting tool 2650, which is insertable into an indentation (e.g., FIG. 23A-23E) on an exposed end of VRB assembly 2590. Adjusting tool 2650 allows for the changing of the orientation of VRB assembly 2590 to adjust the flexibility or stiffness of VRB assembly 2590 to a downward pressure applied to platform 2600.

As would be recognized, and in accordance with another aspect of the invention, the configuration shown in FIG. 26 is similar to the configuration shown in FIGS. 13A and 13B, wherein VRB assembly 2590 extends from a heel section 2610 to a pocket (similar to 1510, FIG. 13B) wherein the positional head 2520 rotates within a pocket similar to 1510 shown in FIG. 13B.

FIG. 27A illustrates a side view of an orthotic platform 2700 in accordance with a second aspect of the invention.

In this illustrated embodiment, platform 2700, similar to platform 2600, includes a heel section 2610 and a mid-arch section 2620, wherein VRB assembly 2590 extends through heel section 2610 toward mid-arch section 2620. Further illustrated is pocket 2710 attached to an underside of platform 2700 positioned below the mid-arch section 2620. In accordance with the principles of the invention, the positional head 2520 of VRB assembly 2590 engages pocket 2710 such that position head 2520 rotates within pocket 2710 as the orientation of VRB section 2510 within VRB assembly 2590 is changed.

Further illustrated is selector 2720, which is positionable between the heel section 2610 and pocket 2710. Selector 2720 includes a passthrough though which VRB assembly 2590 passes as it proceeds from the heel section 2610 to the pocket 2710.

FIG. 27B illustrates a side view of platform 2700 wherein VRB assembly 2590 is extended from the heel section 2610, through selector 2720, to engage pocket 2710.

The use of selector 2720 is advantageous as it allows for the rotation of VRB assembly 2590 without the use of tools. Rather, rotation of selector 2720 causes VRB section 2510 to rotate in a similar manner.

Figure 28:
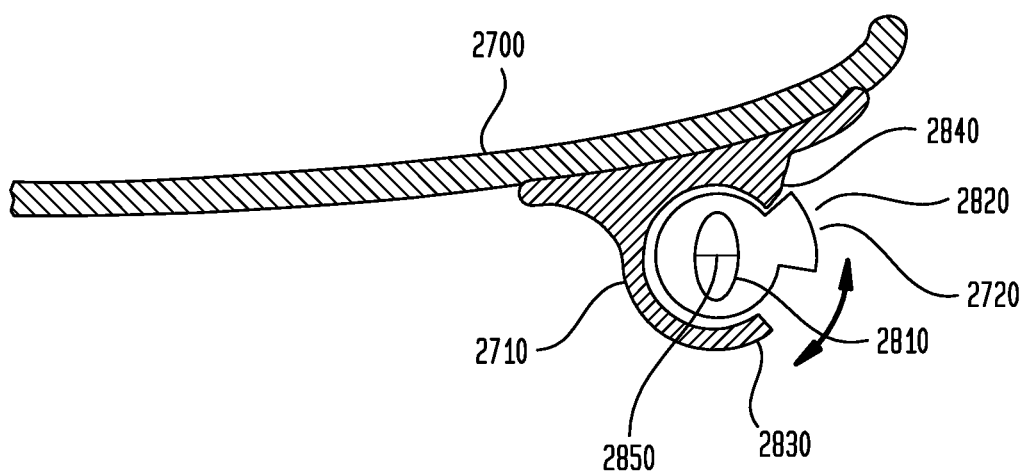
FIG. 28 illustrates a cross-sectional view, through line A-A, of the orthotic platform shown in FIG. 27B.

FIG. 28 illustrates a cross-sectional view, through line A-A, of platform 2700 shown in FIG. 27B. In this cross-sectional view, selector 2720 is shown as including a level 2820, extending along a longitudinal axis of selector 2720 (into the paper) used to change the orientation of selector 2720. Further illustrated is elliptical opening 2810 through which VRB assembly 2590 passes through. Elliptical opening 2810 is sized to capture and retain VRBS 2540 of VRB assembly 2590 such that as the orientation of selector 2720 is changed, the orientation of VRBS 2540 of VRB assembly 2590 also changes.

Although opening 2810 is shown as an elliptical opening it would be recognized that opening may be structured to accommodate any of the VRB configurates shown in FIGS. 1A-1G, without altering the scope of the invention.

Further shown, is lever 2820 being rotatable between two "stops" 2830 and 2840. Stops 2830 and 2840 define a range of motion of VRBS 2540 from a minimum deflection configuration, as shown, and a maximum deflection configuration, not shown. As has been discussed, the maximum deflection configuration occurs when the minor axis 2850 is substantially perpendicular to platform 2700.

Stops 2830 and 2840 may, in one aspect of the invention, represent ends of an opening along a longitudinal axis of pocket 2710

Figure 29A:
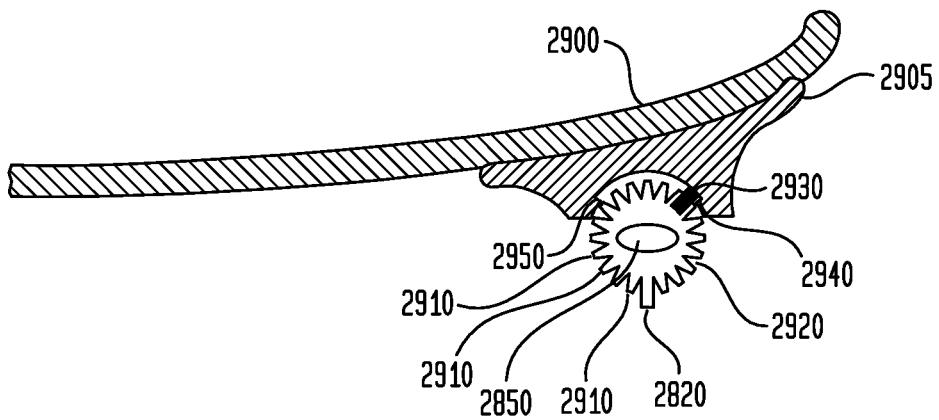
FIGS. 29A, 29B, 29C illustrate a cross-sectional view, through line A-A, of the orthotic platform shown in FIG. 27B in accordance with another aspect of the invention.
Figure 29B:
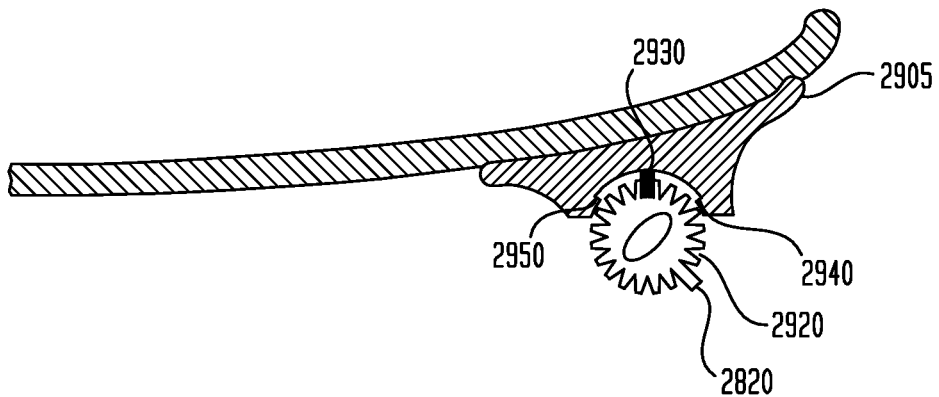

FIGS. 29A-29B illustrate cross-sectional views, through line A-A of FIG. 27B, of alternative positioning of a second exemplary embodiment of selector 2720 in accordance with the principles of the invention.

FIG. 29A illustrates a first positioning of a second exemplary embodiment of selector 2720 (hereinafter referred to as 2920) on a platform 2900 similar to platform 2700 shown in FIG. 27A. In this illustrated embodiment, platform 2900 includes pocket 2905, into which the positional head 2520 of VRB assembly 2590 is inserted. Further illustrated is selector 2920, which includes a lever 2820, as previously discussed, and a plurality of vanes 2910 extending along a longitudinal axis of selector 2920 (i.e., extending into the page). Further illustrated is stop lever 2930, within pocket 2905, which is configured to contact detents 2940 and 2950 on pocket 2905 as selector 2920 rotates from one position to a next position. In the illustrated embodiment shown in FIG. 29A, stop lever 2930 contacts detent 2940 to place VRBS 2540 in a maximum deflection configuration.

FIG. 29B illustrates a second position of second exemplary embodiment of selector 2920, wherein VRBS 2540 is positioned within a mid-deflection configuration.

Figure 29C:
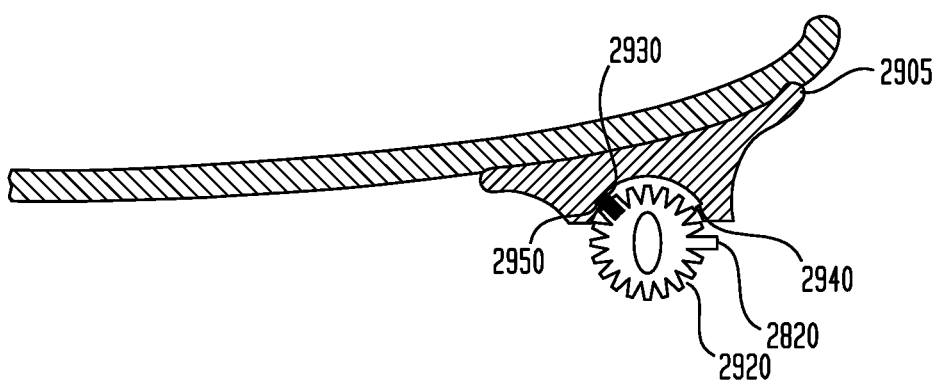

FIG. 29C illustrates a third position of second exemplary embodiment of selector 2920, wherein stop lever 2930 contacts detent 2950 to place VRBS 2510 in a minimum deflection configuration.

Figure 30:
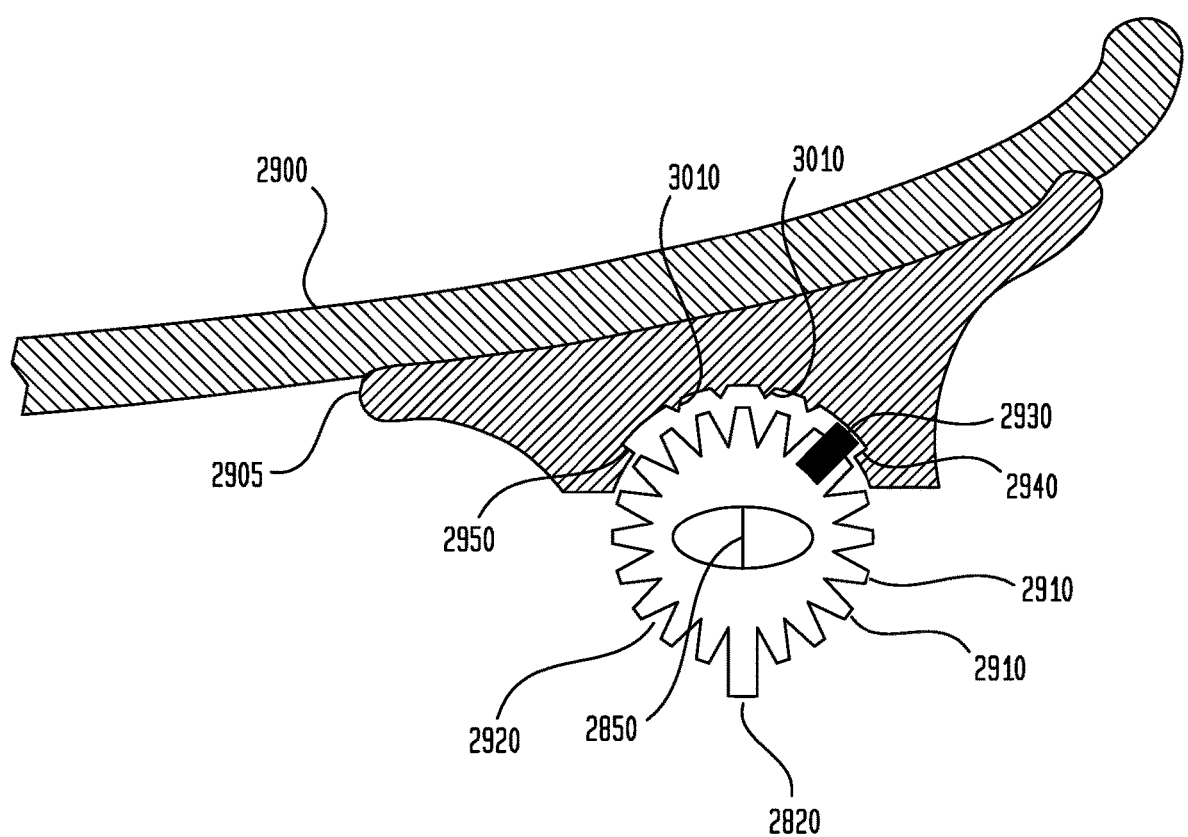
FIG. 30 illustrates an expanded view of the configuration shown in FIG. 29A.

FIG. 30 illustrates an expanded view of the configuration shown in FIG. 29A. In this illustrated configuration, pocket 2905 includes a plurality of vanes 3010 extending into pocket 2905. Vanes 3010 are configured to engage vanes 2910 to provide a means for retaining VRBS 2540 in a selected position. In this illustrated case, VRBS 2540 is retained in a maximum deflection position, as minor axis 2850 of VRBS 2540 is subjected to a downward force applied to platform 2900.

Figure 31A:
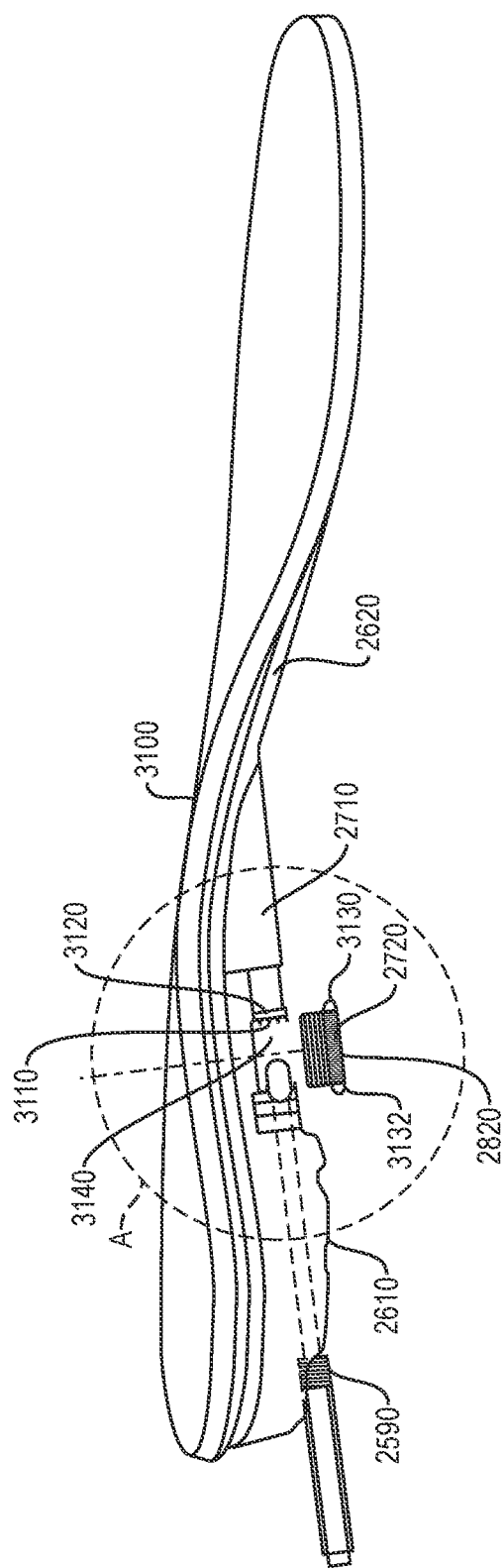
FIGS. 31A and 31B illustrate sides view of a third exemplary orthotic platform in accordance with the principles of the invention.

FIG. 31A illustrates a side view of an orthotic platform 3100 in accordance with a third aspect of the invention.

In this illustrated embodiment, platform 3100, similar to platforms 2600, 2700, includes a heel section 2610 and a mid-arch section 2620, wherein VRB assembly 2590 extends through heel section 2610 toward mid-arch section 2620. Further illustrated is pocket 2710 attached to an underside of platform 2700 positioned below the mid-arch section 2620. In accordance with the principles of the invention, the positional head 2520 of VRB assembly 2590 engages pocket 2710 such that position head 2520 rotates within pocket 2710 as the orientation of VRB section 2510 within VRB assembly 2590 is changed.

Further illustrated is selector 2720, which is positionable between the heel section 2610 and pocket 2710 in a second pocket, referred to as selector insert pocket, 3140. Selector 2720 includes a passthrough though which VRB assembly 2590 passes as it proceeds from the heel section 2610 to the pocket 2710.

In this exemplary embodiment, selector 2720 includes lever 2820, as previously discussed, and further includes lever extensions 3130 and 3132 extending from lever 2820.

In addition, a front wall 3110 of selector insert pocket 3140 includes a plurality of dents 3120, which are configured to engage lever extension 3130 as selector 2820 is rotated. Lever extensions 3130 and 3132 operate as stop levers, which allow for the retention of selector 2820 in a desired position.

Figure 31B:
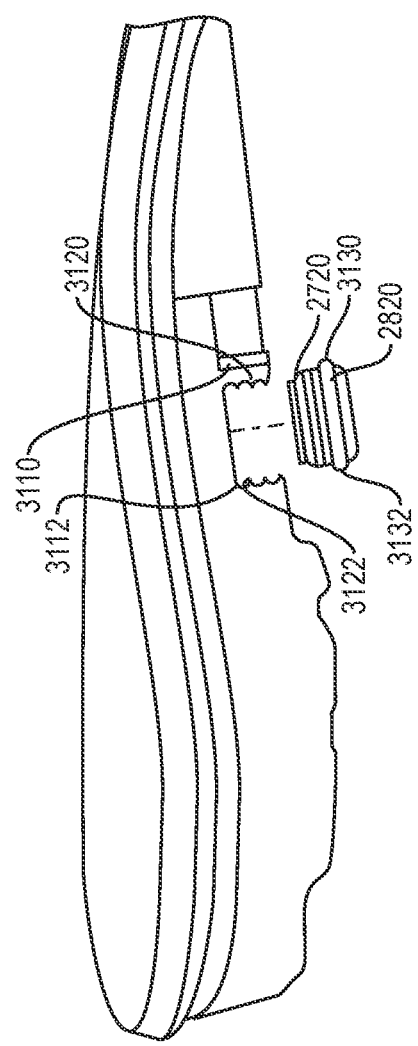

FIG. 31B illustrates an expanded view of the selector insert pocket 3140, identified as section A of FIG. 31A.

In this expanded view, selector insert pocket 3140 is shown comprising a front wall 3110 and a rear wall 3112. Front wall 3110 includes a plurality of detents 3120 and rear wall 3112 includes a similar plurality of detents 3122.

Further illustrated are lever extension 3130 extending from a forward edge of lever 2820 and lever extension 3132 extending from a rear edge of lever 2820. Lever extensions 3130 and 1332, extending external to lever 2820, are configured to engage detents 3120 and 3122, respectively, to retain selector 2720 in a known position with respect to platform 3100.

In accordance with the principles of the invention, as selector 2720 is rotated through the use of lever 2820, extension 3130 and 3132 engage different ones of detents 3120 and 3122, respectfully.

As discussed previously, the change in position of selector 2720 alters the orientation of a Variable Resistance Beam captured within selector 2720 to provide different degrees of resistance to a force applied to platform 3100.

Further illustrated are indicia (numerals 1, 2, 3), which indicate a degree of resistance to a force applied to the platform 3100. Each of the indicia correspond to a position of selector 2820 (and the corresponding VRB) with respect to platform 3100.

VRB 1310, which may be solid, semi-hollow or hollow, with or without geometrically created I-beam effect (i.e., asymmetric geometry, spines) on the outside or interior diameter generates resistance depending on the axis of orientation and/or a fulcrum position has been described herein. A VRB 1310, with incorporated I-beam geometry on the outside diameter, may allow for the dynamic adjustment of resistance of the device. An advantage of a device including VRBs described herein may be compact, lightweight and offer the ability to more easily and quickly change a desired level of resistance than is typically found in units using weights, rubber bands, bows or springs. By simple reposition or rotation of a VRB incorporated into the device, a desired selectable range of resistance level may be achieved. The VRBs 1310 disclosed, herein, can provide resistance, depending on the orientation of the beam, to a bending direction. In addition, an exemplary device incorporating the VRB technology may vary the resistance provided to the user during rehabilitative exercise, without interrupting the exercise cycle. Additional beam resistance is achieved depending upon the relative orientation of the beam within a 180° degree hemisphere of movement relative to the user.

Hence, according to the principles of the invention, a progressive dynamic resistance may be achieved with a variation of the orientation of the beam or shaft shown herein.

In one aspect of the invention, rods with symmetrical cross sections vary their bending resistance by shortening and lengthening the arc length, from fulcrum to anchor point by hand position per indicia.

In another aspect of the invention, rods with asymmetrical cross sections may increase or decrease their bending resistance by rotation of the elongated orientation with respect to a bending force, while maintaining the same hand adjusted position or fulcrum length.

In one aspect of the invention, the VRBs 1310 may be composed of thermoplastic polymers, especially high tenacity polymers, include the polyamide resins such as nylon; polyolefin, such as polyethylene, polypropylene, as well as their copolymers such as ethylene-propylene; polyesters, such as polyethylene terephthalate and the like; vinyl chloride polymers and the like, and polycarbonate resins, and other engineering thermoplastics such as ABS class or any composites using these resins or polymers. The thermoset resins include acrylic polymers, resole resins, epoxy polymers and the like.

Polymeric or composite materials may contain reinforcements that enhance the stiffness or flexure of the flexure resistance spine. Some reinforcements include fibers, such as fiberglass, metal, polymeric fibers, graphite fibers, carbon fibers, boron fibers and Nano-composite additives, e.g., carbon nano-tubes, et al., to fill the molecular gaps, therefore strengthening the material.

Additional materials that the resistance rods or VRBs 1310 may also be composed of include high tensile aircraft aluminum and high carbon spring steel and/or high tensile strength to weight materials.

Figure 12:
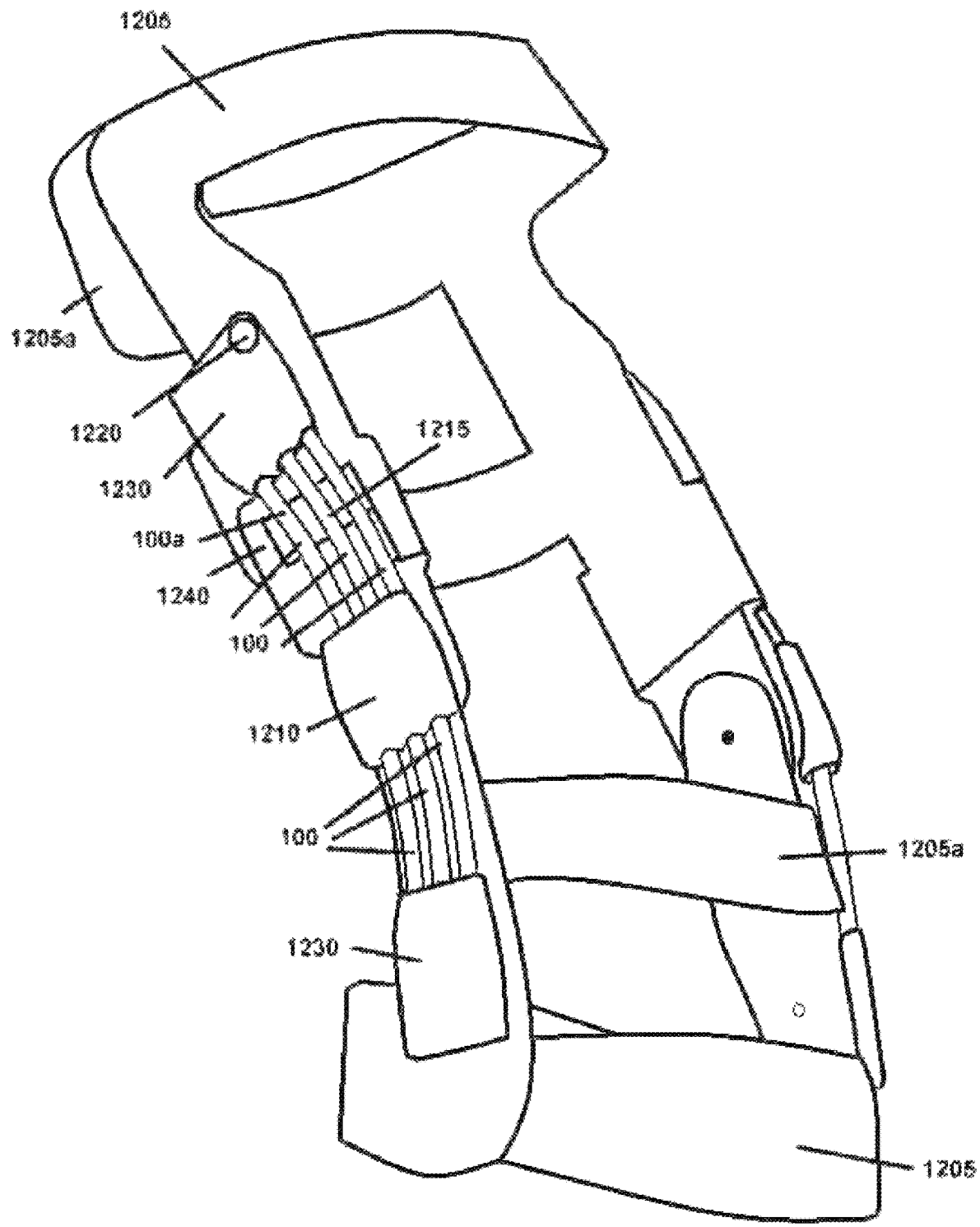
FIG. 12 illustrates an exemplary medical device configured in accordance with the principles of the invention. The resistance beams are employed into mobility assistance and rehabilitative braces that provide dynamic support and suspension via a fulcrum mechanism.

FIG. 12 illustrates an exemplary medical brace in accordance with the principles of the invention. In this illustrative example, at least one VRB 100 is incorporated into a VRB assembly 1215 into an anchor 1230, an adjuster 1220, and a fulcrum 1210. The bracing system in FIG. 12 is comprised of a thigh leg strap collar 1205 attached to a frame with a fulcrum 1210 connected to a hinge 1225 with an upper arm 1240 with a bushing piston acting as a second cartilage.

In this illustrative embodiment, VRBs 100 are adjusted to create a variable flex. Element 1205 illustrates leg strap or collar (thigh). Element 1205a illustrates leg strap or collar (calf). Element 1210 illustrates fulcrum for VRB 100 to maintain controlled bending. Element 1215 illustrates a VRB assembly (one or more VRB's) that acts as a leaf-spring/unloader; i.e., a first suspension point. Element 1220 illustrates VRB assembly adjuster to customize flexibility or resistance. The assembly adjuster 1220 may be a worm gear as previously described. Element 1225 illustrates a hinge that mimics the bio-mechanical movement or range of an anatomical joint (e.g. knee). Element 1230 illustrates VRB assembly anchor with spring/bushings: i.e., a secondary suspension point. Element 1240 illustrates a telescoping upper hinge arm with a bushing piston, a second cartilage: i.e., a third dampening or cushioning point. VRB assemblies 100a or 1215 provides a dynamic supportive structure designed to act as an artificial or second knee to support a damaged or injured one.

An additional benefit of incorporating the VRB 100 technology into medical devices is that the resistance rods, under compression, create a proportioned constant vertical lift to unload 1215 and dynamically support the joint (e.g., a knee) during post op, rehabilitation, arthritis or during extreme sports. Hence, the VRB 100 technology described herein provides a truly functional and adjustable brace that provides for Shock Absorbing 1215, 1230, 1240, Active Suspension 1215, Adjustable Comfort DST Unloader Knee Brace.

As previously described, resistance ranges are generated by rotating the beams over a fulcrum positioned adjacent to a body joint.

Dynamic support is also beneficial for the recuperative period following operation, rehabilitation, arthritis or during extreme sports. Additionally, resistance beam assemblies may also contribute to shock absorption via a bushing and piston arm mechanically connected to the beam assembly. Furthermore, beam assemblies positioned on each side of a joint act as lateral stabilizers.

In one aspect of the invention, the VRB's 100 may be composed of thermoplastic polymers, especially high tenacity polymers, include the polyamide resins such as nylon; polyolefin, such as polyethylene, polypropylene, as well as their copolymers such as ethylene-propylene; polyesters, such as polyethylene terephthalate and the like; vinyl chloride polymers and the like, and polycarbonate resins, and other engineering thermoplastics such as ABS class or any composites using these resins or polymers. The thermoset resins include acrylic polymers, resole resins, epoxy polymers, and the like.

Polymeric materials may contain reinforcements that enhance the stiffness or flexure of the flexure resistance spine. Some reinforcements include fibers, such as fiberglass, metal, polymeric fibers, graphite fibers, carbon fibers, boron fibers and Nano-composite additives, e.g. carbon nano-tubes, et al, to fill the molecular gaps, therefore strengthening the material.

Additional materials that the resistance rods or VRB's may also be composed of include high tensile aircraft aluminum and high carbon spring steel and/or high tensile strength to weight materials.

Although the different applications of the VRBs shown herein refer to VRB 100 (type I), it would be recognized that each of the applications may incorporate one or more of the other type of VRBs (i.e., type II through type VII) without altering the scope of the invention.

The resilient VRB's shown in herein may be used with or in conjunction with sports equipment and exercise apparatus to create meaningful exercise and or other useful mechanisms. For example, devices suitable for exercise equipment, sports equipment, home improvement and medical mobility may be created to selectable control bending strength or resistance ranges to impart performance benefits. VRB's may be secured at one or more fixed points with the appropriate device may be used to provide appropriate variable resistance. In addition, the VRBs may be handheld at various points along the beam length to affect fulcrum resistance and or rotated to different incremental orientations to affect resistance with discrete geometric cross sections. In one aspect of the invention, VRB's may be perpendicularly mounted to a variety of mechanical apparatus to affect resistance and may additionally be handheld in the air to expand the exercise envelop.

The VRB's described herein may be manufactured based on a method selected from a group consisting of: rapid prototyping, stereolithography, molding, casting, extrusion and other known in the art.

VRBs, which may be solid, semi-hollow or hollow, with or without geometrically created I-beam effect (i.e., spines) on the outside or interior diameter generates resistance depending on the axis of orientation and/or a fulcrum position has been described herein. VRBs 100, with incorporated I-beam geometry on the outside diameter, can allow for the dynamic adjustment of resistance of the device. An advantage of a device including a VRBs described herein may be compact, lightweight and offer the ability to more easily and quickly change a desired level of resistance than is typically found in units using weights, rubber bands, bows or springs. By simple hand reposition, as shown in FIG. 3, or rotation of beam of the incorporated into the device a desired resistance level may be achieved. VRBs 100 disclosed, herein, can provide resistance, depending on the orientation of the beam, to the user. In addition, the device can vary the resistance provided to the user during an exercise, without interrupting the exercise cycle. Additional beam resistance is achieved depending upon the relative orientation of the beam within a 180° degree hemisphere of movement relative to the user. Hence, according to the principles of the invention, a progressive dynamic resistance may be achieved with a variation of the orientation of the beam or shaft shown herein.

The principle of Progressive Dynamic Resistance (PDR) are:

controlled and rotatable (variable) resistance beam with ergonomic work zones:

Multiple, sequential, mechanical resistances are achieved for the purpose of rehabilitation and exercising of endo-skeletal musculature.

Increased/decreased incremental mechanical resistance and exercise adjustability is achieved through beam rotation and or fulcrum hand position relative to the beam or arc length/distance along the resistance beam to impart desired work load.

PDR's 180° or 360° degree range of dynamic arcing motion provides an exercise resistance program for every male or female body type with variability in muscle size and strength to provide gain after unilateral resistance training of progressive resistance exercise (PRE).

PDR's incremental mechanical resistance capability (i.e., resistance adjustability through rotation and or fulcrum hand position) facilitates and customizes the user's strength curve and exercise requirements from simply moving hand/leg position to tailor the optimum resistance to maximize the workout of the targeted muscle group.

PDR resistance beam technology does not have mechanical flat spots or dead spots and provides continuous resistance curve to maximize workout loading on the targeted muscle groups, thus creating a more effective work out.

PDR's bend/arc/range of motion means that as the resistance beam is bent farther away from a plane of minimum resistance, the sustained mechanical resistance incrementally increases, creating a progressively more intense and effective work out/work load on the target muscle group.

Continuous Progressive Dynamic Resistance loading from the bending of VRBs 100 is a highly effective biomechanical exercise.

In other aspects of the invention, different types of sport equipment and apparatus may incorporate the VRBs 100 technology described herein. Examples in which VRB 100 technology may be applied are:

FlexGym & FlexTrax products represent an apparatus or structure to hold a plurality of rod holders into which VRB 100 resilient adjustable or non-adjustable solid or tubular rods and other exercise apparatus are inserted to allow users to perform a variety of exercises. FIGS. 3, 4 and 5 illustrate an exemplary system in accordance with the principles of the invention.

FlexBoard product represents an apparatus or structure wherein a transportable structural panel resting on the ground with rod holders into which VRB's 100 are inserted perpendicularly to allow users to perform a variety of exercises. FIG. 6 illustrates an exemplary FlexBoard system in accordance with the principles of the invention.

FlexGym represents an apparatus or structure wherein the VRB 100 technology of the present invention may be incorporated into a plurality of structural tracks with rod holders providing multiple positions into which the VRB 100 resilient adjustable or non-adjustable solid or tubular rods and other exercise apparatus are inserted to allow users to perform a variety of exercises in an I-formed structure, with a cantilevered bench that folds down or may be a free form bench. In addition, the floor tracks, which also comprise the lower structure of the unit, can be optionally retracted to the vertical tracks when not in use.

In one aspect of the invention a means to track and record exercise cycles per set of the user may be incorporated. For example, biometric data of the user may be recorded on a smart card, a smart phone, a computer, etc. so exercise cycles can be recorded. In addition, biometric data of the user may be conveyed by magnet, reflector, RFID, Wi-Fi or other means to measure or quantify exercise cycle.

In another aspect of the invention, the exercise apparatus may include sensors (e.g., Wi-Fi) to sense proximity of the user as the user approaches the exercise apparatus. The sensors may also be in communication with a user's smart phone transmitter or other technical means and the exercise apparatus respond may be setup to correspond to a user's particular exercise regime.

Another embodiment of the exercise apparatus sensors would recognize a user via sensor or Wi-Fi or iPhone transmitter that would initiate servo-mechanisms to proactively set a customized workout cycle. This would mean that the track holder along the track, be it vertical or horizontal, and would be matched to the user's ergonomic body size and requirements.

In another aspect of the invention a video display or monitor may be incorporated to enable a user to receive instructions regarding a particular exercise or to watch one or more programs of interest during the exercise session.

Returning to FIG. 3, FIG. 3 represents a method for incorporating the VRB 100 technology into an apparatus for exercise with one or more anchor point which is represented by the product FlexToner. More specifically, the present invention related to a resilient adjustable or non-adjustable solid or tubular rod exercise apparatus handheld at one or more places and flexed.

Other VRB 100 exercise apparatus applications are, but not limited to, upper and or lower body exercise machines: (e.g. treadmills, stair climbers, elliptical trainers, stationary bikes, mobility, medical, rehabilitative systems that create and control selectable bending strength or resistance ranges with fixed rotation to impart PDR) isolating the upper and or lower body for exercise.

The present invention may be incorporated into devices that provide for low impact/low resistance exercises (e.g., Rehabilitative and Geriatric exercisers) to strengthen and rehabilitate post-surgical, bed-ridden, sport injury and or geriatric benefit. Typically, these devices may employ VRBs 100 that are matched to the strength of the user. For example, VRB 100 may be adjusted to provide rigid support during an initial healing phase of a sports injury and then adjusted to provide lesser amount of support to compensate for progress during the healing of the sport injury.

Although, the present invention is described with regard to a plurality of different equipment, it would be recognized that the described equipment are merely examples to which the VRB technology described herein may be applied. The examples provided herein are merely illustrative of the application of the claimed technology and the examples are not intended to limit the subject matter claimed.

In other aspects of the invention, other types of sports equipment and apparatus may incorporate the VRB 100 technology described herein. Examples in which VRB 100 technology may be applied are, but not limited to:

Golf Clubs

Golf clubs may be formed of graphite, wood, titanium, glass fiber or various types of composites or metal alloys. Each varies to some degree with respect to stiffness and flexibility. However, golfers generally carry onto the golf course only a predetermined number of golf clubs.

Varying the stiffness or flexibility of the golf club is not possible, unless the golfer brings another set of clubs of a different construction. Even in that case, however, the selection is still somewhat limited.

Nevertheless, it is impractical to carry a huge number of golf clubs onto the course, each club having a slight nuance of difference in flexibility and stiffness than another. Golf players prefer taking onto the course a set of clubs that are suited to the player's specific swing type, strength and ability.

Returning to FIG. 8, which illustrates an exemplary embodiment of an internal VRB 100 in a hollow shaft (e.g., a golf shaft). As previously discussed, the VRB 100 is centrally raised or lowered within the golf shaft, the fulcrum or kick point is raised or lowered, thereby changing the shaft flex. The 360 degree symmetrical geometry provides a solution for an adjustable golf club and would be fully compliant with the existing USGA rules of golf and assorted international golf associations.

Running Shoes, Training Shoes, Basketball Shoes

The transmission of the shoe wearer's strength (power) from their legs into the ground is directly affected by the sole stiffness of the shoe. Runners may gain more leverage and, thus more speed, by using a stiffer sole. Basketball players may also affect the height of their jumps through the leverage transmitted by the sole of their shoes. If the sole is too stiff, however, the toe-heel flex of the foot is hindered.

It is advantageous that the shoe wearer have the ability to tailor the sole stiffness to his/her individual weight, strength, height, running style, and ground conditions. Preferably, the shoe wearer may tailor the stiffness of the shoe sole to affect the degree of power and leverage that is to be transmitted from the wearer into the ground.

In this example, VRBs 100 are insertable, insert molded or structurally connected to the shoe sole in lateral and/or longitudinal positions within the sole and are all rotatable to a fixed and mechanically locked position to effect custom flexural resistance range. Additionally, zones of resistance are customizable, e.g. the right pad of the foot can be made more rigid than the left pad side through the beam's rotated orientation. Thus, the degree of flexibility may be customized to accommodate a user's desired preferences.

Incorporation of the VRB 100 technology into running shoes, as shown in FIG. 11, provides a dynamic adjustable in-sole suspension system that can absorb the weight of the wearer and release it per each step.

Hockey Sticks

Hockey includes, but is not limited to, ice hockey, street hockey, roller hockey, field hockey and floor hockey.

Hockey players may require that the flexure of the hockey stick be changed to better assist in the wrist shot or slap shot needed at that particular junction of a game or which the player was better at making. Players may not usually leave the field to switch to a different piece of equipment during play.

Younger players may require more flex in the hockey stick due to lack of strength and such flex may mean the difference between the younger player being able to lift the puck or not when making a shot since a stiffer flex in the stick may not allow the player to achieve such lift.

In addition, as the younger players ages and increases in strength, the player may desire a stiffer hockey stick, which in accordance with convention means the hockey player would need to purchase additional hockey stick shafts with the desired stiffness and flexibility characteristics. Indeed, to cover a full range of nuances of differing stiffness and flexibility characteristics, hockey players would have available many different types of hockey sticks.

Even so, the hockey player may merely want to make a slight adjustment to the stiffness or flexibility of a given hockey stick to improve the nuances of the play. Thus, the incorporation of the VRB technology into hockey sticks (shaft and/or blade) provides for variations in the stiffness and flexibility that may be adjusted as the user progresses in their ability.

Incorporation of the VRB technology into hockey sticks is similar to that shown in FIG. 7.

In other aspects of the invention, different type of Do-it-Yourself (DIY) and Home Improvement products and devices may incorporate the VRB technology described herein. Examples in which VRB technology may be applied are:

Lawn Equipment:

Adjustable Lawn Rake with VRB 100 Tines:

The VRB 100 technology described by the present invention may be incorporated into a lawn rake. In this case, an adjustable rake with a rotatable VRB 100 down the shaft of the rake may be created. The VRB 100 facilitates the adjustment of the lawn rake, with the ability to adjust stiffness of the shaft relative to the load (e.g., light grass clippings, heavy grass clipping, wet grass clippings).

Incorporation of the VRB 100 technology into lawn rake (or other similar handled devices) is similar to that shown in FIG. 10A and FIG. 10B.

In another embodiment, the VRB 100 technology described by the present invention may be incorporated into tines of a lawn rake creating an adjustable rake. Thus, the VRB 100 facilitates the adjustment of a lawn/utility rake by providing the ability to create variable shaft resistance for light or heavy duty gravel raking due to its rotated orientation. The VRB 100 adjustment setting may simultaneously rotate the rake's tines from 0° to 90°, thus affecting a stiffer tine orientation. The tines may be elliptical or oval in shape in an embodiment of an elliptical VRB 100. When the tines are in a 0° orientation, they are the most flexible and suitable for raking leaves or light duty yard work. When the tines are in a 90° orientation, they are the most rigid and suitable for raking heavy duty gravel. The flexural change of tines can be further impacted by means of adjusting where the center point of a fulcrum of the flex of tines is located.

FIG. 10A illustrates an exemplary lawn rake incorporating the VRB 100 technology disclosed herein. FIG. 10A and FIG. 10B illustrates a rake assembly 1000 including a handle 1010 and a tine assembly 1015 including a plurality of VRB 100 tines that are simultaneously adjusted through rotation. FIG. 10B illustrates a bottom view of rake 1000 showing the orientation of the tines 100 at a maximum resistance level (90 degree orientation).

Thus, the incorporation of the VRB 100 technology in the tines creates a flexible lawn rake to alter the flex characteristics of the rake.

Although, the present invention is described with regard to a plurality of different lawn equipment, it would be recognized that the lawn equipment described herein are merely examples to which the VRB technology described herein may be applied. The examples provided herein are merely illustrative of the application of the claimed technology and the examples are not intended to limit the subject matter claimed.

In other aspects of the invention, different type of medical products and devices may incorporate the VRB technology described herein. Additional examples in which VRB technology may be applied are: Mobility assistance and Rehabilitative Braces that provide dynamic support and suspension for joints and orthotic braces: Foot, ankle, knee, hip, back, shoulder, elbow, wrist, neck (i.e., Prophylactic, Functional Support, Post-operative, Unloader and or Extreme Sports, acting as a second compression driven reactive joint, et al.).

In this aspect of the invention, the VRBs 100 may be used to create a medical brace or orthotic device that by provides a dynamic support and suspension system with variable and adjustable resistance settings to achieve an adjustable performance range so as to customize the brace or device during the recuperation stage of the wearer, acting as external supporting spring ligament or adjustable box spring structure and/or further supported by a conformal brace framework. For example the conformal brace framework may be a mechanical joint and/or a flexible webbing, e.g., Ballistic nylon/Neoprene et al.

In one aspect of the invention, the medical brace or orthotic device may be used to:

1. control, guide, limit and/or immobilize an extremity, joint or body segment for a particular reason;
2. To restrict movement in a given direction;
3. To assist movement generally;
4. To reduce weight bearing forces for a particular purpose;
5. To aid rehabilitation from fractures after the removal of a cast; and
6. To otherwise correct the shape and/or function of the body, to provide easier movement capability or reduce pain.

Although, the present invention is described with regard to knee brace, FIG. 12, it would be recognized that the described braces are merely examples to which the VRB technology described herein may be applied. The examples provided herein are merely illustrative of the application of the claimed technology and the examples are not intended to limit the subject matter claimed. For example, the VRB technology described herein may be applied to braces that are used for the back, arm, elbow, neck, and legs, without altering the scope of the invention.

In another aspect of the VRB technology described herein, braces or devices may be constructed wherein the VRB beams are equipped with attached sensors [e.g. Electrogoniometer] to provide continuous bio-mechanic feedback or other biomechanical sensor means of medical or injury diagnostic. For example, compression, extension, articulation, Range and/or twisting measurements may be made and provided to a network (e.g., a WIFI, wireless) to monitor the movement of the user.

In another aspect of the invention, the braces including the VRB technology described herein may include sensors, such as impedance wire sensors, accelerometer, stressors, etc., to measure flexural strength, cycle counts per day to measure Joint performance, injury, damage assessment, etc., so that an appropriate monitoring of the healing of the effected joint may be monitored. Such monitoring is valuable in the field of professional sports medicine, for example.

In still another embodiment of the VRB technology described herein provides further benefits in the medical profession, wherein a VRB may be made from a BIO-Degradable Polymer that may be incorporated into an Internal Fixation brace. In this case, the internal VRB may be rotatable using outside setting pins connected to an internal worm gear at the head of the internal VRB. The main benefit of bio-degradable VRB fixation beams is that they require no post-operative surgery to remove. The biopolymers may be of a non-toxic material capable of maintaining strong mechanical integrity until engineered to degrade, wherein controlled rates of degradation (typically a function of crystallinity) are predetermined. An additional benefit is to not create an immune response and or the products of degradation must also be non-toxic.

Controlled degradation rates may be affected by a percentage of polymer crystallinity, molecular weight, hydrophobicity and location within the body.

Examples of promising biodegradable polymers to be made into VRBs through extrusion and or injection molding are, but not limited to, 3-hydroxypropionic acid, the suture polymer Polyglycolide and or Poly(lactic acid) or polylactide (PLA). A thermoplastic aliphatic polyester that degrades into lactic acid, a natural waste product of the body.

Although the different applications of the VRB shown herein refer to VRB 100 (type I), it would be recognized that each of the applications may incorporate one or more of the other type of VRBs (i.e., type II through type VII) without altering the scope of the invention.

The specification is to be regarded in an illustrative manner, rather than with a restrictive view, and all such modifications are intended to be included within the scope of the invention.

Benefits, advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

While there has been shown, described, and pointed out fundamental novel features of the present invention as applied to preferred embodiments thereof, it will be understood that various omissions and substitutions and changes in the apparatus described, in the form and details of the devices disclosed, and in their operation, may be made by those skilled in the art without departing from the spirit of the present invention. It is expressly intended that all combinations of those elements that perform substantially the same function in substantially the same way to achieve the same results are within the scope of the invention. Substitutions of elements from one described embodiment to another are also fully intended and contemplated. For example, any numerical values presented herein are considered only exemplary and are presented to provide examples of the subject matter claimed as the invention. Hence, the invention, as recited in the appended claims, is not limited by the numerical examples provided herein.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

The term "comprises", "comprising", "includes", "including", "as", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "or" refers to an inclusive "or" and not to an exclusive "or". For example, a condition A or B is satisfied by any one of the following: A is true (or present) and B is false (or not present); A is false (or not present) and B is true (or present); and both A and B are true (or present).

Any reference signs in the claims should not be construed as limiting the scope of the claims or the invention described by the subject matter claimed.

What is claimed is:

1. An orthotic platform comprising:
    a heel section;
    a front section; and
    a mid-arch section between the heel section and the front section:
        a rod extending from said heel section to said mid-arch section, said rod comprising:
            a cylindrical first section proximate to said mid arch-section; and a variable resistance beam section attached to said first section; and a second cylindrical section attached to said variable resistance beam section, said second cylindrical section extending through said heel section; and a selector insert positioned within a selector pocket, wherein said variable resistance beam section passes through said selector, said selector configured to:

rotate said variable resistance beam section to alter an orientation of said variable resistance beam section with respect to said mid arch section.

2. The orthotic platform of claim 1, wherein said selector comprising a lever, said lever indicating said orientation of said variable resistance beam with respect to said platform.

3. The orthotic platform of claim 1, wherein said in a selector insert pocket comprises:

at least one detent.

4. The orthotic platform of claim 3, wherein said at least one detent is positioned on an upper surface of said selector pocket, and said selector insert comprises:

a stop lever configured to engage one of said at least one detent.

5. The orthotic platform of claim 4, wherein said selector insert pocket comprising:

a first stop; and a second stop, wherein said stop lever is configured to:
be positioned between said first stop and said second stop.

6. The orthotic platform of claim 3, wherein said at least one detent is positioned on at least one: a front wall of said selector insert pocket and a rear wall of said selector insert pocket, and said selector comprises:

a lever comprises a stop lever, said stop lever configured to engage one of said at least one detent.

7. The orthotic platform of claim 1, wherein said mid arch section comprises:

a pocket, wherein a first section of said rod is rotatable within said pocket.

8. The orthotic platform of claim 7, wherein said first section of said rod further comprises:

a head, wherein said head rotates within said pocket.

9. The orthotic platform of claim 1, wherein said rod is composed of a material selected from a group consisting of: plastics, thermoplastic polymers, copolymers, polyesters, vinyl chloride polymers, polycarbonate resin, metal, re-enforced plastics and nano-reinforced plastics.

10. The orthotic platform of claim 1, wherein a cross section of said variable resistance beam section is selected from a group consisting of: rectangular, elliptical and cylindrical shaft comprising at least one external spline.

11. The orthotic platform of claim 1, wherein said rod is orientated at an angle with respect to a surface upon which said heel section rests, wherein said angle is within a range of 1 degree to 45 degrees.

12. The orthotic platform of claim 1, wherein the platform is selected from a material being at least one of: rigid, semi-rigid and flexible.

13. An orthotic platform comprising:

a mid-arch section;

a heel section; and a selector insert positioned within a selector pocket between said mid-arch section and said heel section, and a rod extending through said selector between the heel section and the mid-arch section, wherein said selector is configured to:

retain said rod; and rotate said rod within said selector insert pocket.

14. The orthotic platform of claim 13, wherein said selector comprises a lever; and a stop lever, wherein said selector insert pocket comprises:

at least one detent, wherein said lever is configured to:
rotate said selector to able said stop lever to engage one of said at least one detent.

15. The orthotic platform of claim 14, wherein said at least one detent is positioned on an upper surface of said selector insert pocket.

16. The orthotic platform of claim 14, wherein said at least one detent is positioned on at least one of: a front wall of said selector pocket and a rear wall of said selector insert pocket.

17. The orthotic platform of claim 13, wherein said rod comprises:

a first section comprising: a head section, wherein said head section is, configured to contact said mid-arch section;

a variable resistance beam section comprising a cross-sectional configuration selected from a group comprising; rectangular, and elliptical, and a second section.

18. The orthotic platform of claim 17, wherein said mid-arch section comprising:

a pocket, wherein said head section is configured to rotate within said pocket.

19. The orthotic platform of claim 13, wherein said rod is orientated at an upward angle with respect to said heel section.

* * * * *